(12) United States Patent
Caputo et al.

(10) Patent No.: US 6,448,008 B1
(45) Date of Patent: Sep. 10, 2002

(54) FLUORESCENT CYANINE LABELS CONTAINING A SULFAMIDO LINKER ARM

(75) Inventors: Giuseppe Caputo, Turin; Leopoldo Della Ciana, Lugo, both of (IT)

(73) Assignee: Innosense, S.r.l. (IT)

( * ) Notice: Subject to any disclaimer, the term of this patent is extended or adjusted under 35 U.S.C. 154(b) by 0 days.

(21) Appl. No.: 09/609,035

(22) Filed: Jun. 30, 2000

(30) Foreign Application Priority Data

Jul. 2, 1999 (EP) .............................. 99112696

(51) Int. Cl.[7] .................. C12Q 1/68; C07H 21/04; C07H 21/02; C07H 21/00; A01N 57/00
(52) U.S. Cl. .................. 435/6; 536/24.2; 536/23.1; 536/25.32; 514/112; 514/222.2; 514/224.2
(58) Field of Search .............. 536/24.2, 23.1, 536/25.32; 435/6, 24.2, 40.5; 514/112, 222.2, 224.2; 252/301.21, 301.16

(56) References Cited

U.S. PATENT DOCUMENTS 5,714,386 A * 2/1998 Roederer .................. 436/546
5,808,044 A   9/1998 Brush et al. .............. 536/22.1

OTHER PUBLICATIONS

Mujumdar et al., Bioconjugate Chemistry, vol. 4, No. 2, pp. 105–111, 1993.*

(List continued on next page.)

*Primary Examiner*—W. Gary Jones
*Assistant Examiner*—Jehanne Souaya
(74) *Attorney, Agent, or Firm*—Myers Bigel Sibley & Sajovec, PA

(57) ABSTRACT

A fluorescent cyanine dye of the following general formula is disclosed:

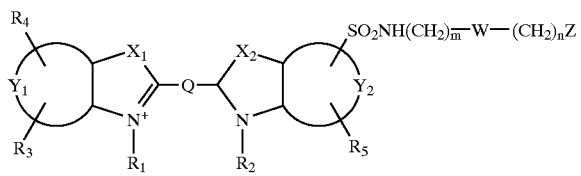

wherein:

$X_1$ and $X_2$ are independently selected from the group consisting of —O—, —S—, —C(CH$_3$)$_2$ or —C=CH$_2$;

$Y_1$ and $Y_2$ are nonmetal atoms required to form a benzo-condensed or naphtho-condensed ring; Q is a conjugated moiety that increases the fluorescent quantum yield and the stability of the compound;

$R_1$ and $R_2$ are independently selected from the group consisting of H, $C_1$–$C_4$, alkyl, alkylensulfonic group or alkylensulfonate group wherein the alkylene group has from 1 to 4 carbon atoms; R3, R4 and R5 are independently selected from the group consisting of H, a sulfonic group, a sulfonate group, alkylensulfonic, alkylensulfonate and —SO$_2$NH(CH$_2$)$_m$—W—(CH$_2$)$_n$Z, wherein alkylene has 1 to 4 carbon atoms, with the proviso that at least one of $R_1$ to $R_5$ contains a sulfonic or sulfonate group; W is absent or is a group selected from —SO$_2$NH, —O—, —COO—, or —CONH—; n=0–12 and m=0–12 with the provisos that m+n≦12 and at least one of m and n≠0; and Z is, or contains a N, O or S nucleophile functionality or is, or contains a functionality capable of reacting with N, O or S nucleophiles. Nucleophile functionalities include —NH$_2$, —OH, and —SH groups; groups capable of reacting with such functionalities include —COCl, —COOCOR, —CONHNH$_2$, N-hydroxysuccinimido esters, —NCS, —CHO, —COCH$_2$I, phosphoramidite and maleimido.

14 Claims, 57 Drawing Sheets

OTHER PUBLICATIONS

Ernst et al.; "Cyanine Dye Labeling Reagents for Sulfhydryl Groups," *Cytometry* 10:3–10 (1989).

Mank et al.; "Visible Diode Laser–Induced Fluorescence Detection In Liquid Chromatography After Precolumn Derivatization Of Amines," *Analytical. Chemistry* 67:10 1742–1748 (May 15, 1995).

Mujumdar et al.; "Cyanine Dye Labeling Reagents Containing Isothiocyanate Groups," *Cytometry* 10:11–19 (1989).

Mujumdar et al.; "Cyanine Dye Labeling Reagents: Sulfoindocyanine Succinimidyl Esters," *Bioconjugate Chemistry* 4:2 105–111 (Mar./Apr. 1993).

Strekowski et al.; "Substitution Reactions Of A Nucleofugal Group In Heptamethine Cyanine Dyes. Synthesis Of An Isothiocyanato Derivative For Labeling Of Proteins With A Near–Infrared Chromophore," *J. Org. Chem.* 57:17 4578–4580 (1992).

* cited by examiner 2 a 2 b 2 c 2 d 2 e 2 f (a)

(b)

(i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite (i-Pr$_2$N$_2$)POCE = bis-(N,N-diisopropyl)-cyanoethyl phosphoramidite
Pam = Phosphoramidite $R_1, R_2 = H, OH$ $R_1, R_2 = H, OH$ $R_1, R_2 = H, OH$ R = H, Cl
$R_1$, $R_2$ = H, OH R = H, Cl
R$_1$, R$_2$ = H, OH $R_1, R_2 = H, OH$

FLUORESCENT CYANINE LABELS CONTAINING A SULFAMIDO LINKER ARM

CROSS-REFERENCE TO RELATED APPLICATIONS

The present application claims priority to European Patent Application No. 99112696.2 filed Jul. 2,1999.

FIELD OF THE INVENTION

The present invention relates to a new class of fluorescent dyes belonging to the cyanine family. The new fluorescent dyes can be excited using powerful yet inexpensive light emitting diodes and diode lasers; they exhibit good water solubility and can be attached or conjugated to a wide variety of molecules or surfaces for labelling purposes.

BACKGROUND OF THE INVENTION

There has been, in recent years, an upsurge in research concerning the fluorescent labelling of biological compounds for the purpose of developing simpler, more sensitive assay methods. In particular, a class of fluorescent dyes has attracted much attention, namely the class of cyanine dyes. While in the past much work on these compounds was focused on obtaining lipophylic materials to be used in photographic processes, the current field of application in the biological sciences requires instead hydrophylic species. Moreover, a new requirement emerged, in the necessity of providing reactive spacer links to be used for the binding of the dyes to biomolecules.

With reference to the basic structure of the compounds such as shown in FIG. 1, it can be seen that such linker arms can be generally attached to either the aromatic portion of the molecule, or to the indolenine nitrogens, or to the polymethine bridge forming the Q moiety.

For example, Waggoner at al. described in Cytometry 10, 3–10 (1989) iodoacetamido groups bound to the aromatic frame, for the purpose of labelling thiol containing molecules, and isothiocyanide groups also bound to aromatic frame for labeling amine containing compounds (in Cytometry 10, 11–19 (1989).

Mank and coworkers in Anal. Chem. 67, 1742–1748 (1995) made N-hydroxysuccinimide (NHS) ester cyanine dyes derivatives from carboxyl groups or carboxymethyl groups attached to the aromatic frame, for precolumn derivatisation of amines in liquid chromatography. The labelled amines could then be detected with ultra high sensitivity by visible diode laser-induced fluorescence.

Waggoner and co-workers developed cyanine labels in which the reactive NHS function is connected to the indolenine nitrogen by an alkyl chain (Mujumdar et al., Bioconjugate Chem. 4, 105–111, 1993). This approach was also followed by Brush and Erie (U.S. Pat. No. 5,808,044) who disclosed a method for making cyanine phosphoramidites useful in nucleotide labelling.

Patonay and co-workers described a tricarbocyanine class of cyanine dye containing isothiocyanide groups attached to the polymethine bridge via a thiophenol linker for the binding of molecules with the amino functionality in J. Org. Chem, 57, 4578–4580 (1992).

While the previous approaches achieved various degrees of success, in many cases they introduced unwanted side effects in the dyes. For example, when the reactive group is directly attached to aromatic frame, the fluorescence efficiency of the dye is negatively affected as shown in Anal. Chem. 67, 1742–1748 (1995). In other cases, the existence of a flexible side chain directly attached to the indolenine N allows the labeled molecule to come into close contact with the chromophoric polymethine chain: this can also perturb or negatively affect the fluorescence of the dye by intermolecular quenching. Finally, some approaches (e.g. Organic Chem, 57, 4578–4580 (1992) can be used only for particular dyes.

SUMMARY OF THE INVENTION

Figure 1:
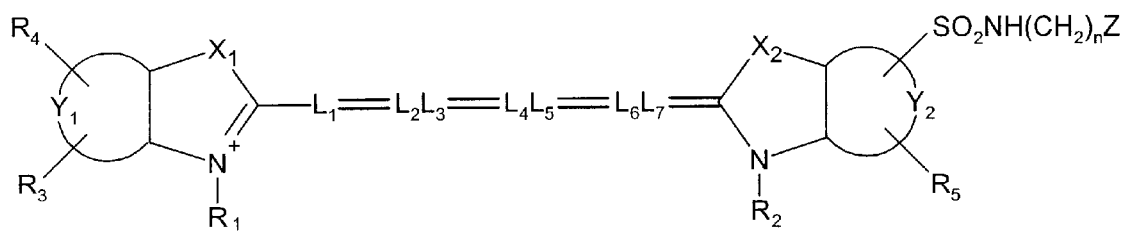
FIG. 1 depicts the general formula of fluorescent cyanine dyes according to the present invention.

According to the present invention fluorescent cyanine dyes have been developed with suitable reactive groups linked to the aromatic framework via a sulfamidoalkyl chain, as shown in FIG. 1.

A wide variety of fluorescent cyanine labels can be made by following this approach, useful for labelling molecules containing amino, thiol, hydroxyl functionalities. By the same general procedure, cyanine labels can also be made suitable for binding molecules containing aldehydes, carboxylic acid derivatives such as chlorides, anhydrides and active esters, or maleimido groups. The present invention offers considerable advantages over previously disclosed methods in terms of eliminating all possible interferences between the fluorescent cyanine labels and the labeled molecule. Its also of more general applicability.

These valuable properties are obtained by attaching a flexible alkylene spacer arm to the rigid aromatic frame of the dye via a very stable and easy to introduce sulfamido bond. Since the reactive portion of the labels is positioned at the very end of the aforementioned alkylene chain the labeled molecule is made incapable of coming into close contact with the chromophoric polymethine segment of the dye. However, the flexibility provided by the alkylene chain can often be advantageous in obtaining a good labelling yield, especially with hindered molecules.

The aryl sulfamido group was chosen because it does not interfere with the fluorescent behaviour of the dye and also because its precursor, the sulfonate group is commonly found in a very large number of arylamines, which are needed for the synthesis of the cyanine dyes. In contrast, the carboxyl group, which was chosen as a linker or for direct activation via NHS esters, not only causes a decrease in the fluorescence quantum yield of the dyes as shown by Mank and coworkers in Anal. Chem. 67, 1742–1748 (1995) but also the aminoaryl carboxyl precursors suitable for the dye synthesis are not as generally available as the corresponding aminoaryl sulfonic acids or sulfonates. The latter statement applies in particular to the naphthalene series. In this case the carboxyl and amino groups need to be located in different aromatic rings to allow the formation of the indolenine precursor. However, in all the commonly available amino naphtalene carboxylic acids both functional groups are attached to the same ring. In contrast, dozens of aminonaphthalene sulfonic acids are available due to their use as dye intermediates and in many such compounds the amino and sulfonic groups are found in separate rings as required by the present invention.

DETAILED DESCRIPTION OF THE INVENTION

The present invention is directed to fluorescent dyes of the formula:

(1)

$R_4$ ... $SO_2NH(CH_2)_{\overline{m}}W\text{—}(CH_2)_nZ$ wherein:
- $X_1$ and $X_2$ are independently selected from the group consisting of —O—, —S—, —C(CH$_3$)$_2$ or —C═CH$_2$;
- $Y_1$ and $Y_2$ are nonmetal atoms required to form a benzocondensed or naphtho-condensed ring;
- Q is a conjugated moiety that increases the fluorescent quantum yield and the stability of the compound;
- $R_1$ and $R_2$ are independently selected from the group consisting of H, $C_1$–$C_4$, alkyl, alkylensulfonic group or alkylensulfonate group wherein the alkylene group has from 1 to 4 carbon atoms;

$R_3$, $R_4$ and $R_5$ are independently selected from the group consisting of H, a sulfonic group, a sulfonate group, alkylensulfonic, alkylensulfonate and —SO$_2$NH(CH$_2$)$_m$—W—(CH$_2$)$_n$Z, wherein alkylene has 1 to 4 carbon atoms, with the proviso that at least one of $R_1$ to $R_5$ contains a sulfonic or sulfonate group;

W is absent or is a group selected from —SO$_2$NH, —O—, —COO—, or —CONH—; n=0–12 and m=0–12 with the provisos that m+n≦12 and at least one of m and n≠0;

and Z is, or contains a N, O or S nucleophile functionality or is, or contains a functionality capable of reacting with N, O or S nucleophiles.

Nucleophile functionalities include —NH$_2$, —OH, and —SH groups; groups capable of reacting with such functionalities include —COCl, —COOCOR, —CONHNH$_2$, N-hydroxysuccinimido esters, —NCS, —CHO, —COCH$_2$I, phosphoramidite and maleimido; R is a C1–C4 alkyl.

Preferably, at least two of the groups $R_1$ to $R_5$ contain a sulfonic acid or a sulfonate group.

Preferably, $R_3$, $R_4$, $R_5$ may all be a group of the type —SO$_2$NH(CH$_2$)$_m$—W—(CH$_2$)$_n$Z thus providing a dye with up to four reactive functionalities.

Q is preferably a polymethine chain having from 3 to 7 carbon atoms preferably selected from the group consisting of:

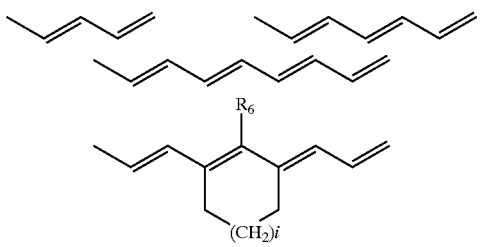

Wherein $R_6$ is H, a halogen atom or the group SO$_2$NH(CH$_2$)$_m$—W—(CH$_2$)$_n$Z and i is 0 or 1.

Also included within the scope of the invention are the valence tautomers of the compounds of formula (1) wherein the valence tautomerism is intended to mean the shifting of the conjugated bonds in the polymethine chain.

Figure 2:
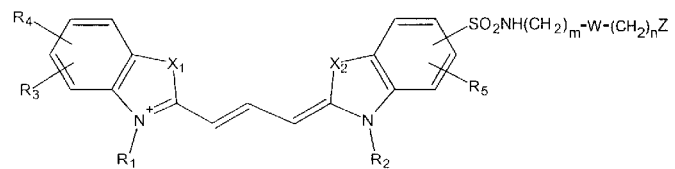
FIG. 2 depicts the general formulae of the fluorescent labeling dyes (2a–2f) of the present invention.
Figure 2:
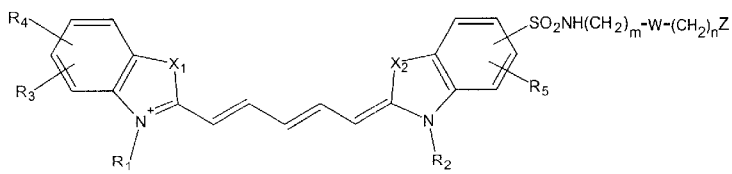
Figure 2:
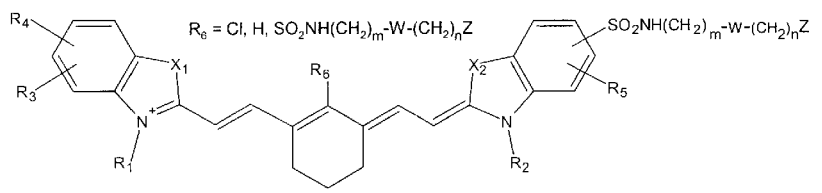
Figure 2:
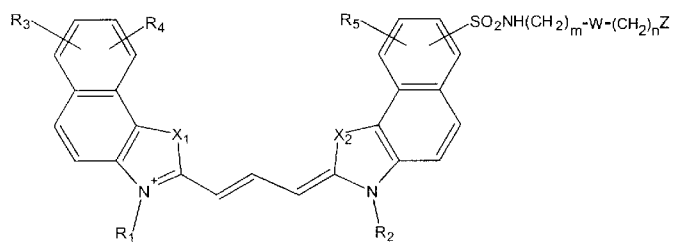
Figure 2:
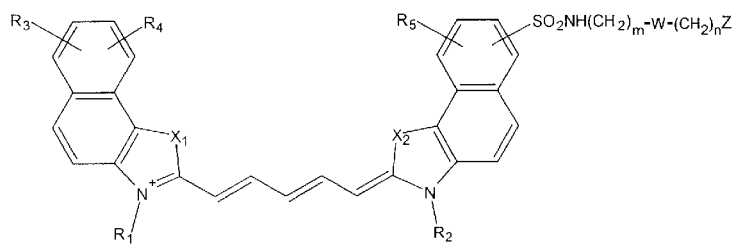
Figure 2:
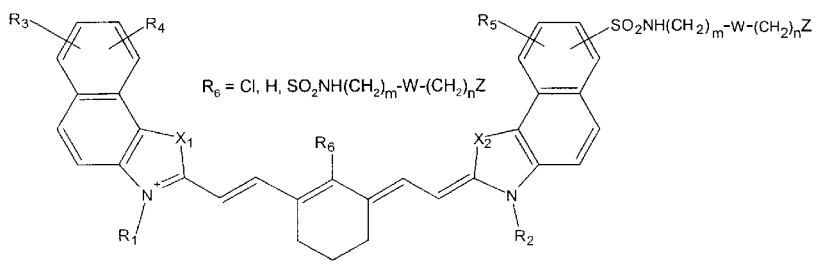
Figure 3:
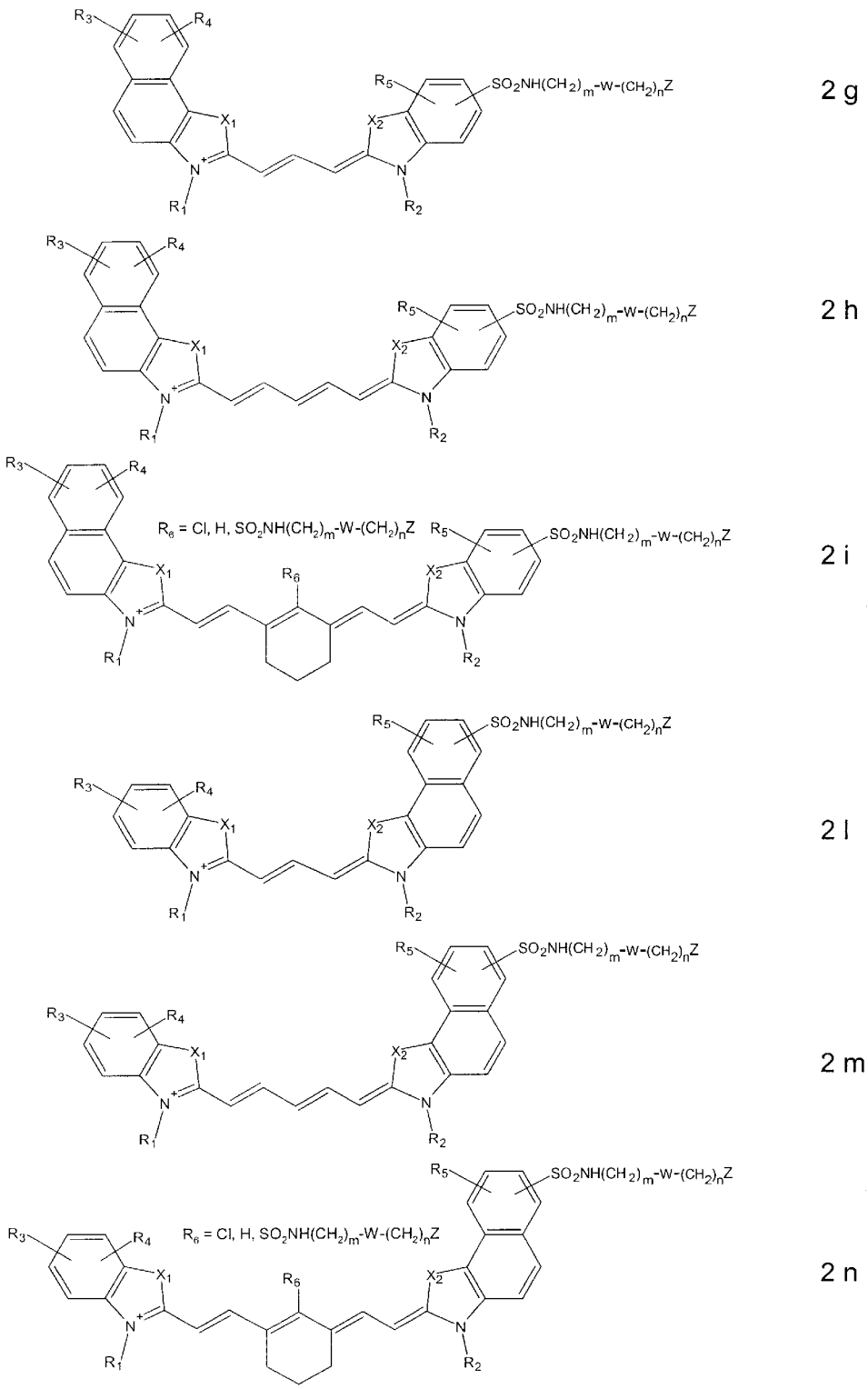
FIG. 3 depicts the general formulae of the fluorescent labeling dyes (2g–2n) of the present invention.
Figure 4:
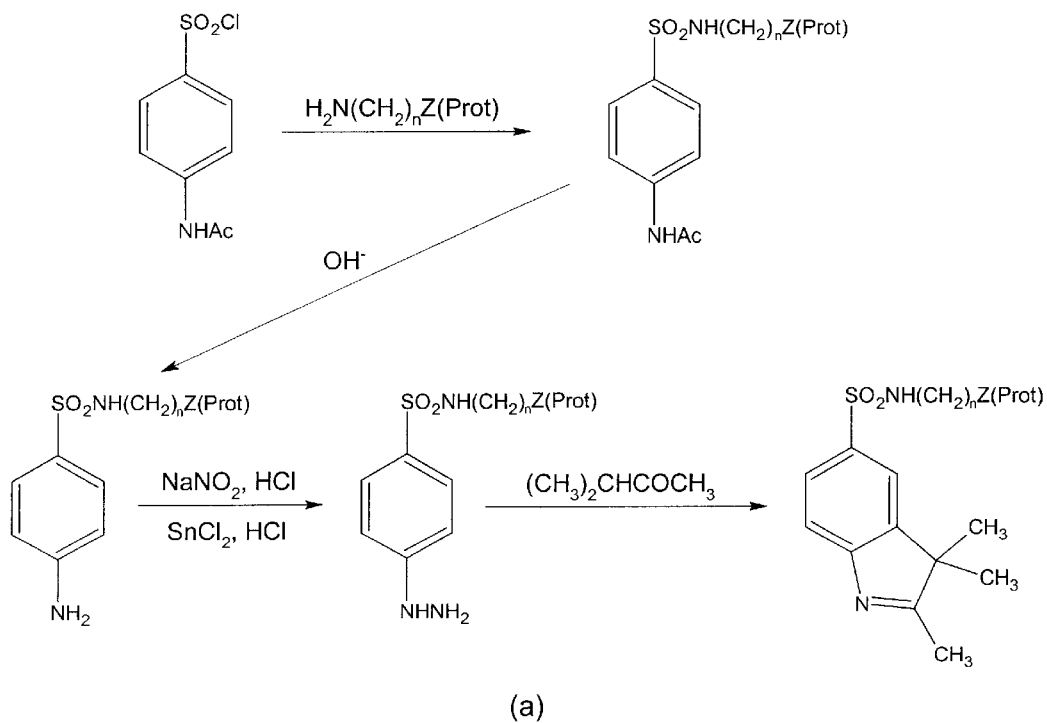
FIG. 4 depicts general methods for the preparation of 2,3,3-trimethyl-(3H)-indoles with sulfamidoalkyl linker arms used in the syntheses of cyanine dyes according to the present invention.
Figure 4:
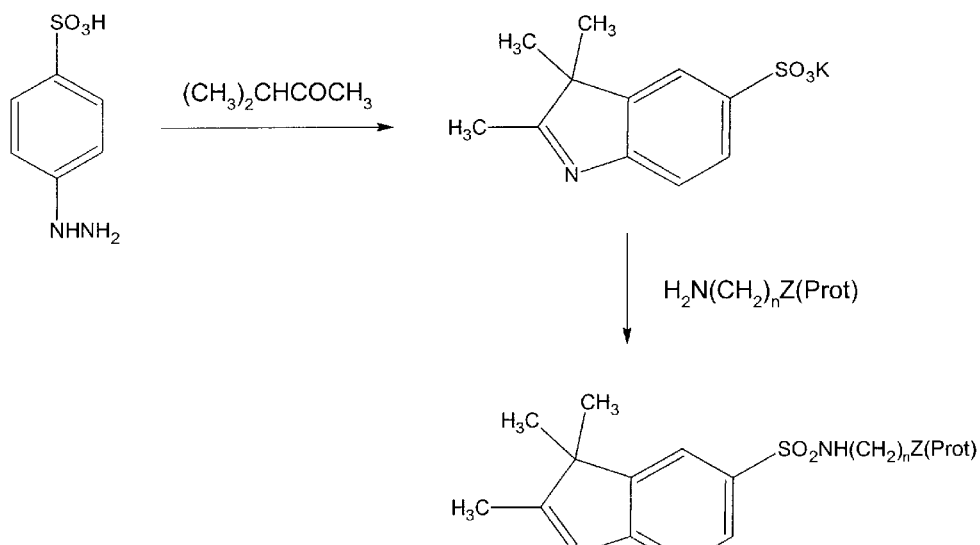
Figure 5:
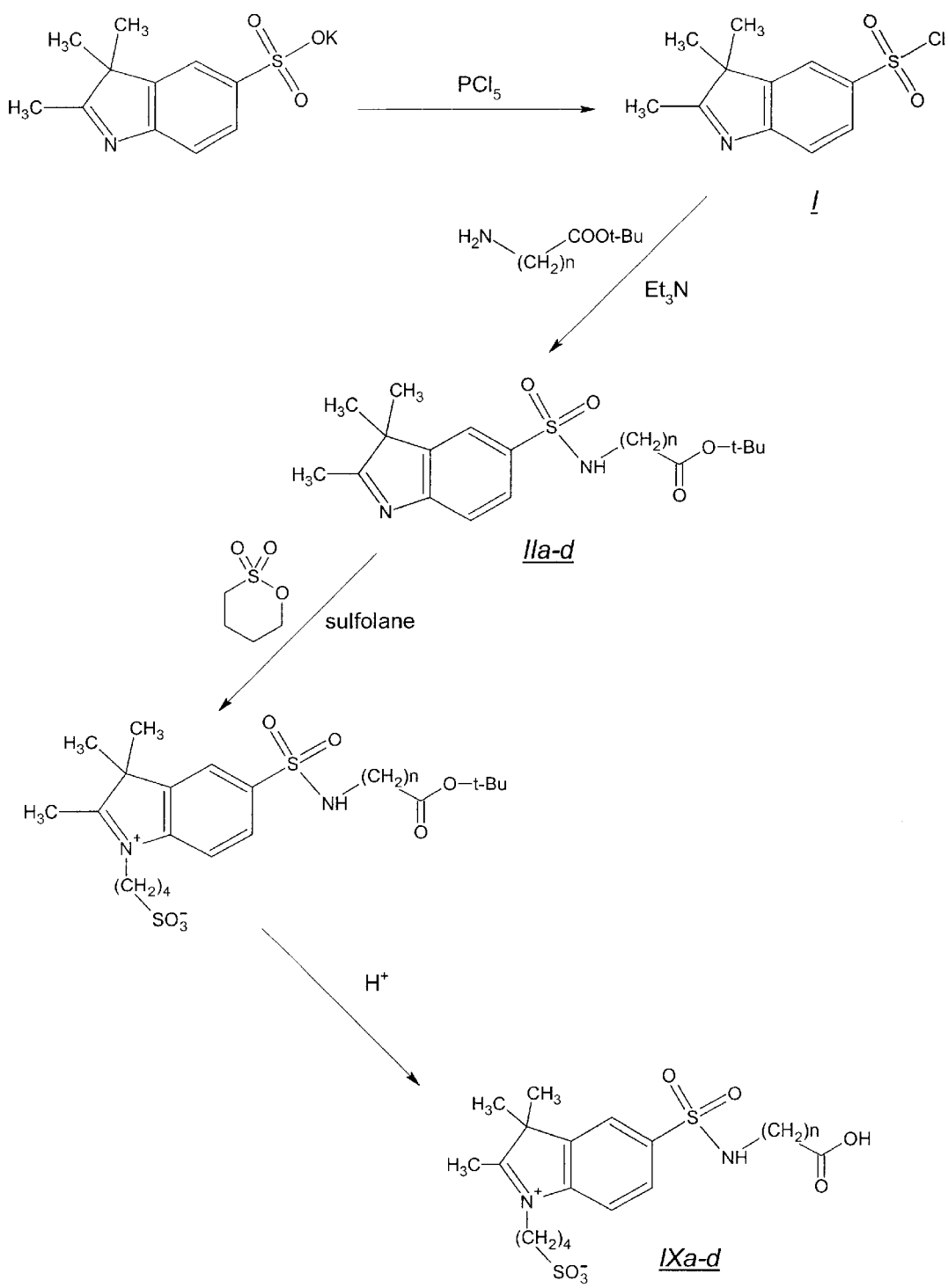
FIG. 5 outlines the preparation of IXa–d.
Figure 6:
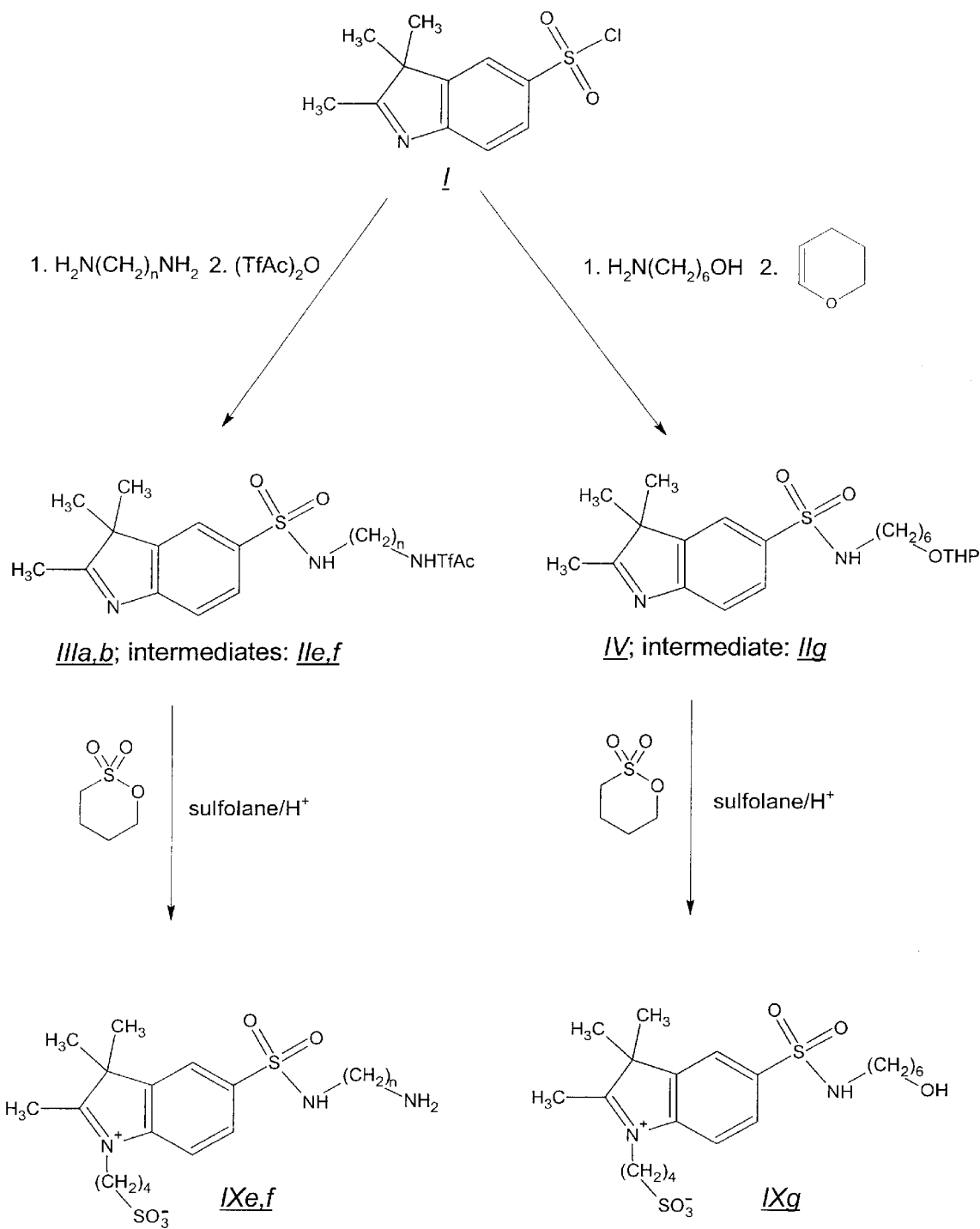
FIG. 6 outlines the preparation of IXe–g.
Figure 7:
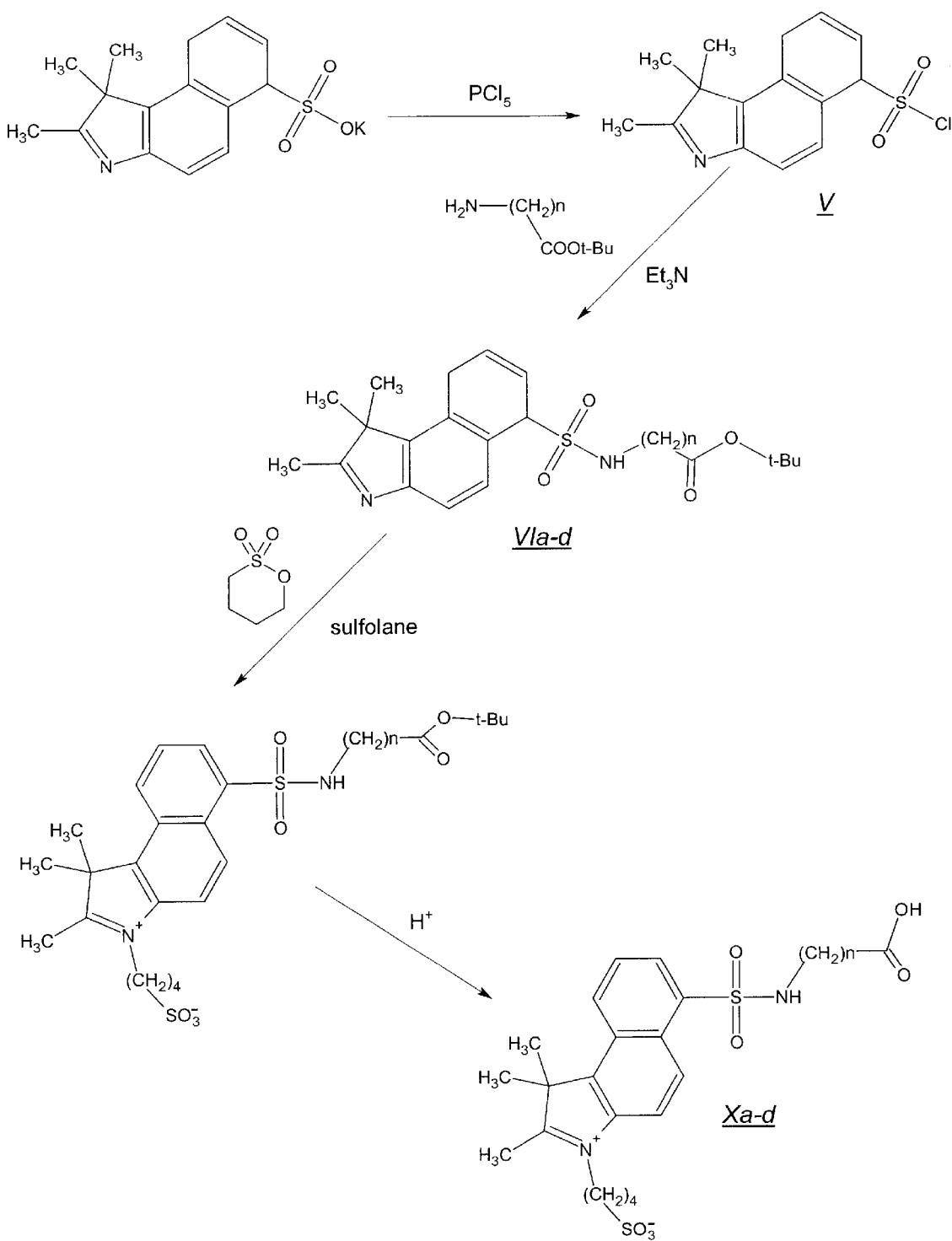
FIG. 7 outlines the preparation of Xa–d.
Figure 8:
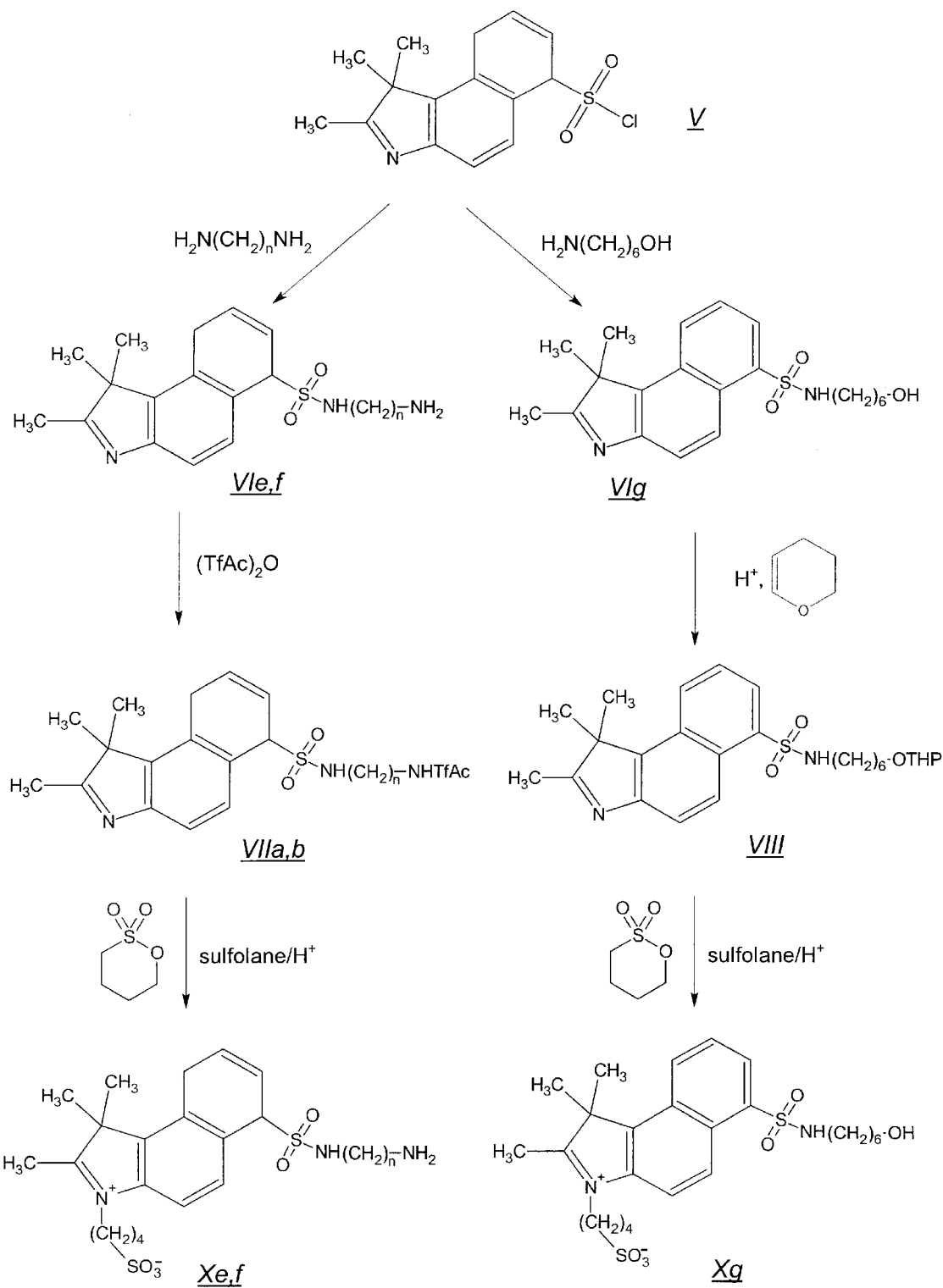
FIG. 8 outlines the preparation of Xe–g.
Figure 9:
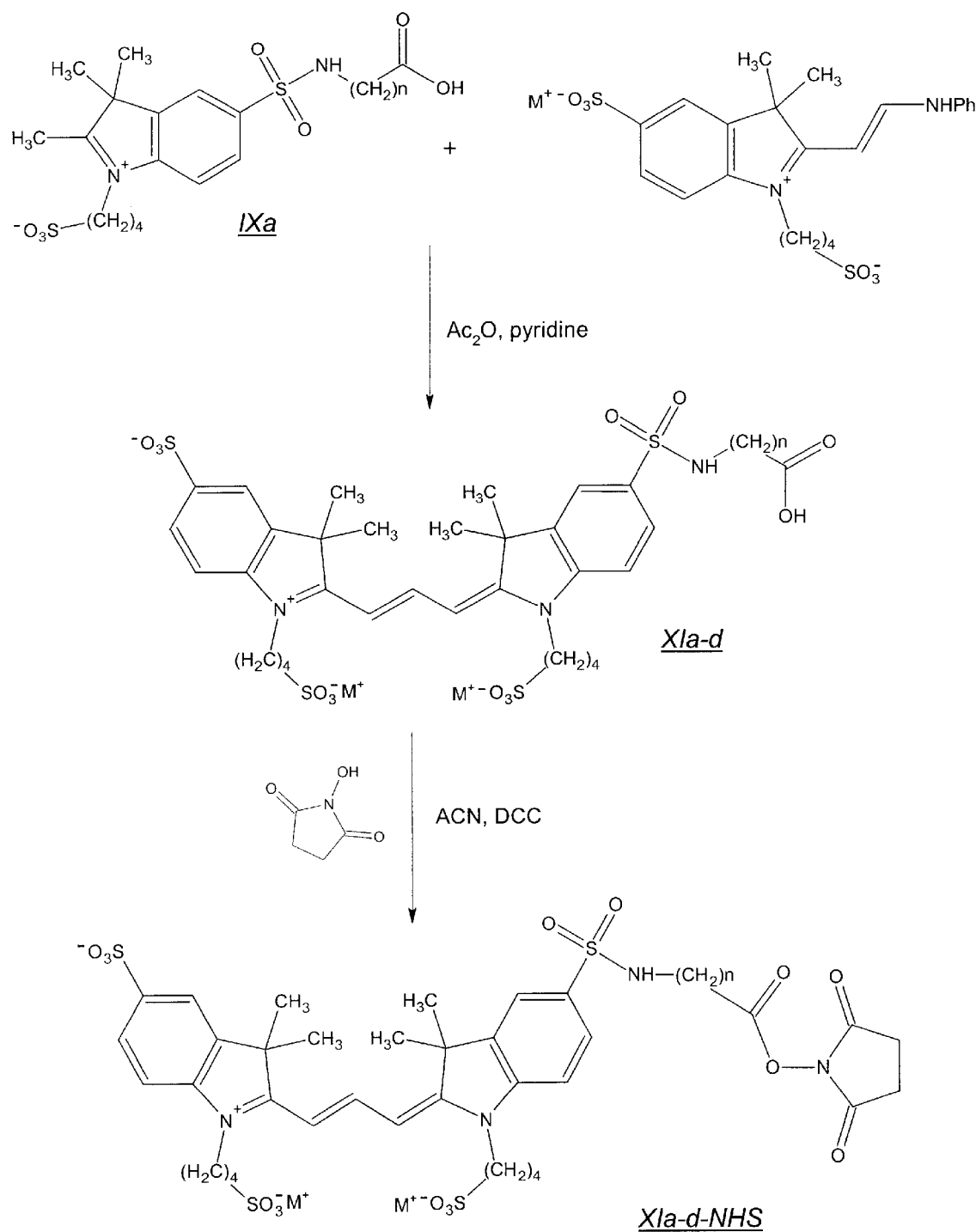
FIG. 9 outlines the preparation of XIa–d, and XIa–d-NHS.
Figure 10:
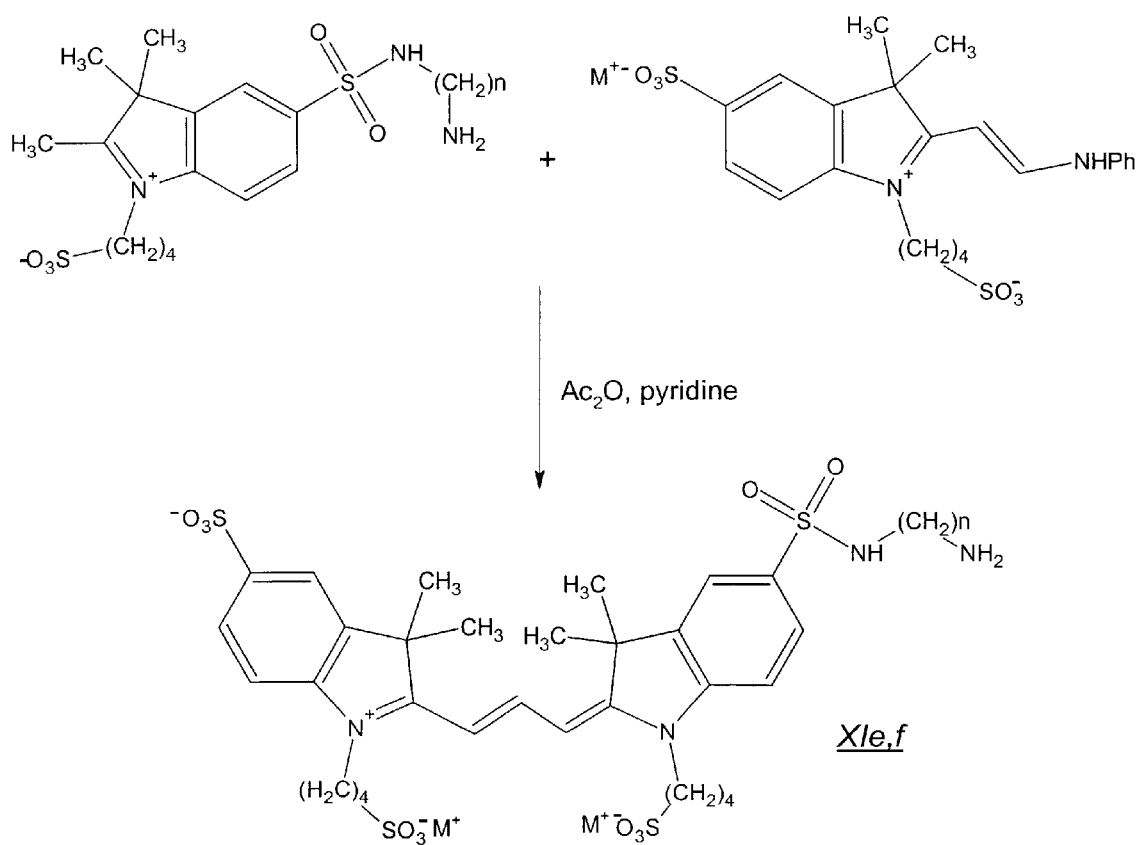
FIG. 10 outlines the preparation of XIe and XIf.
Figure 11:
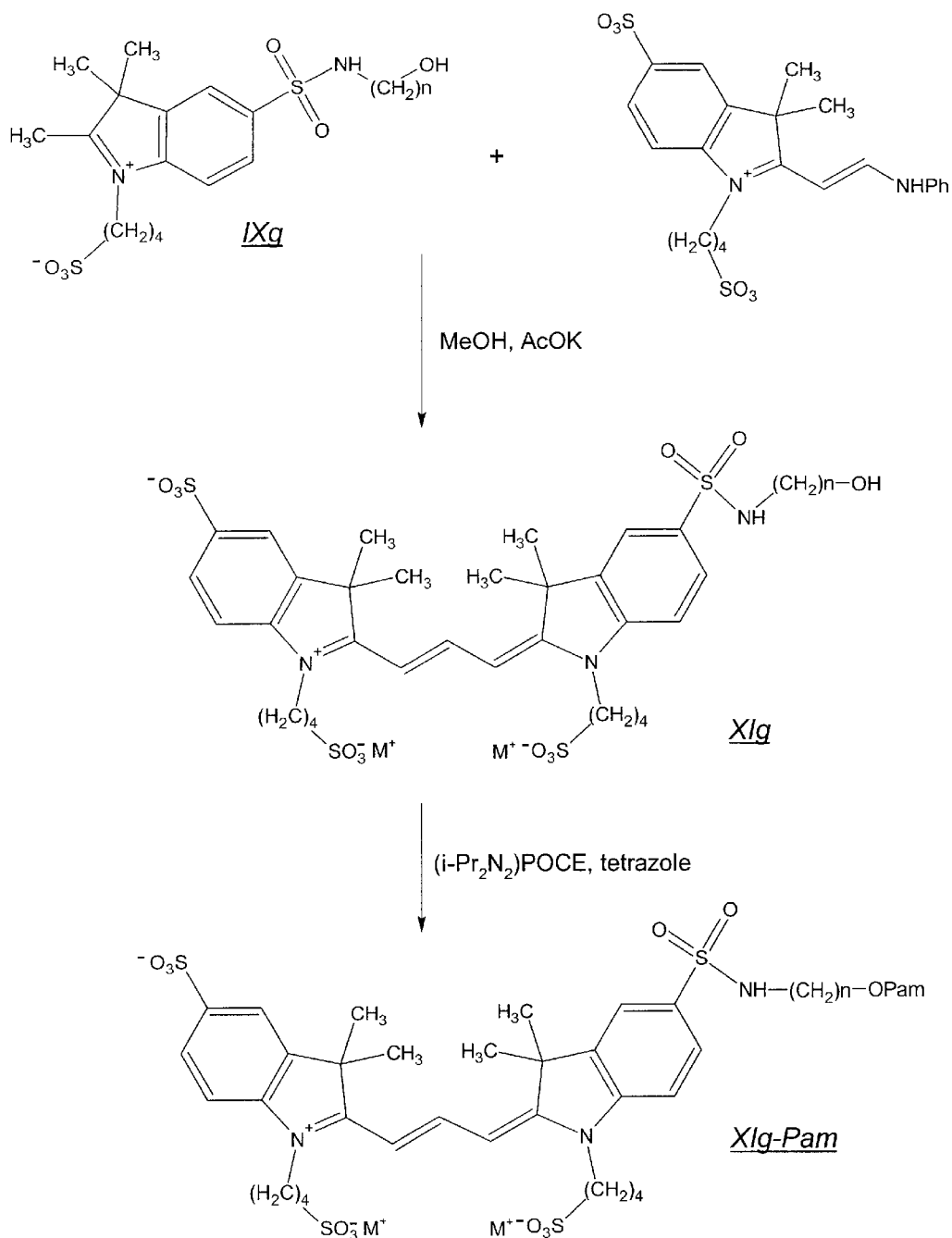
FIG. 11 outlines the preparation of XIg and XIg-Pam.
Figure 12:
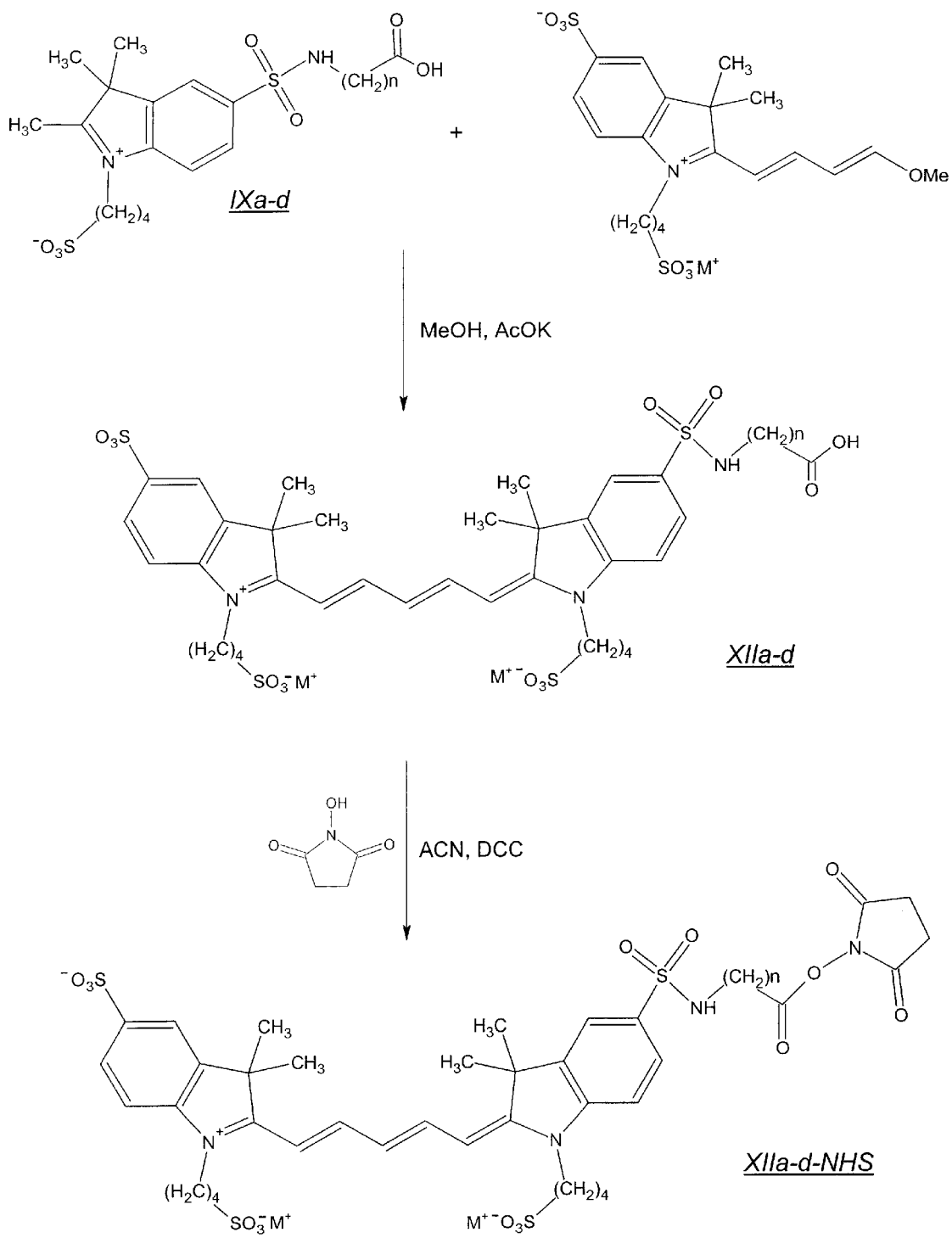
FIG. 12 outlines the preparation of XIIa–d and XIIa–d-NHS.
Figure 13:
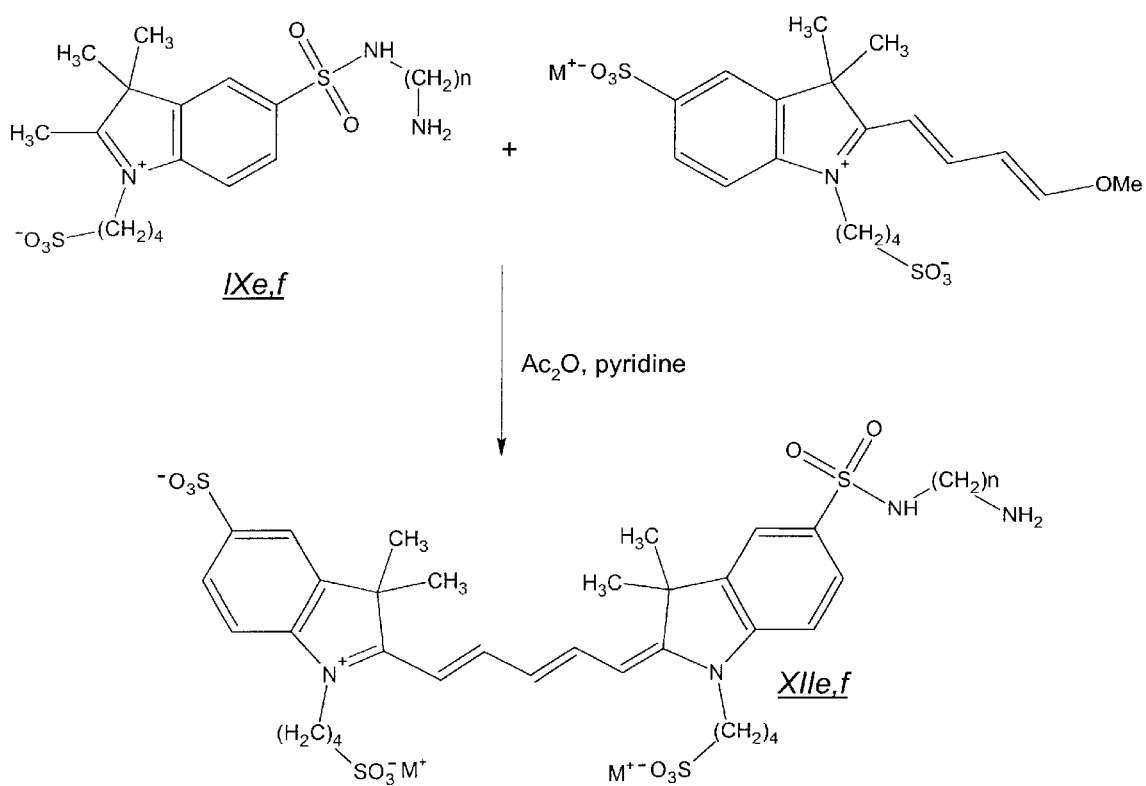
FIG. 13 outlines the preparation of XIIe and XIIf.
Figure 14:
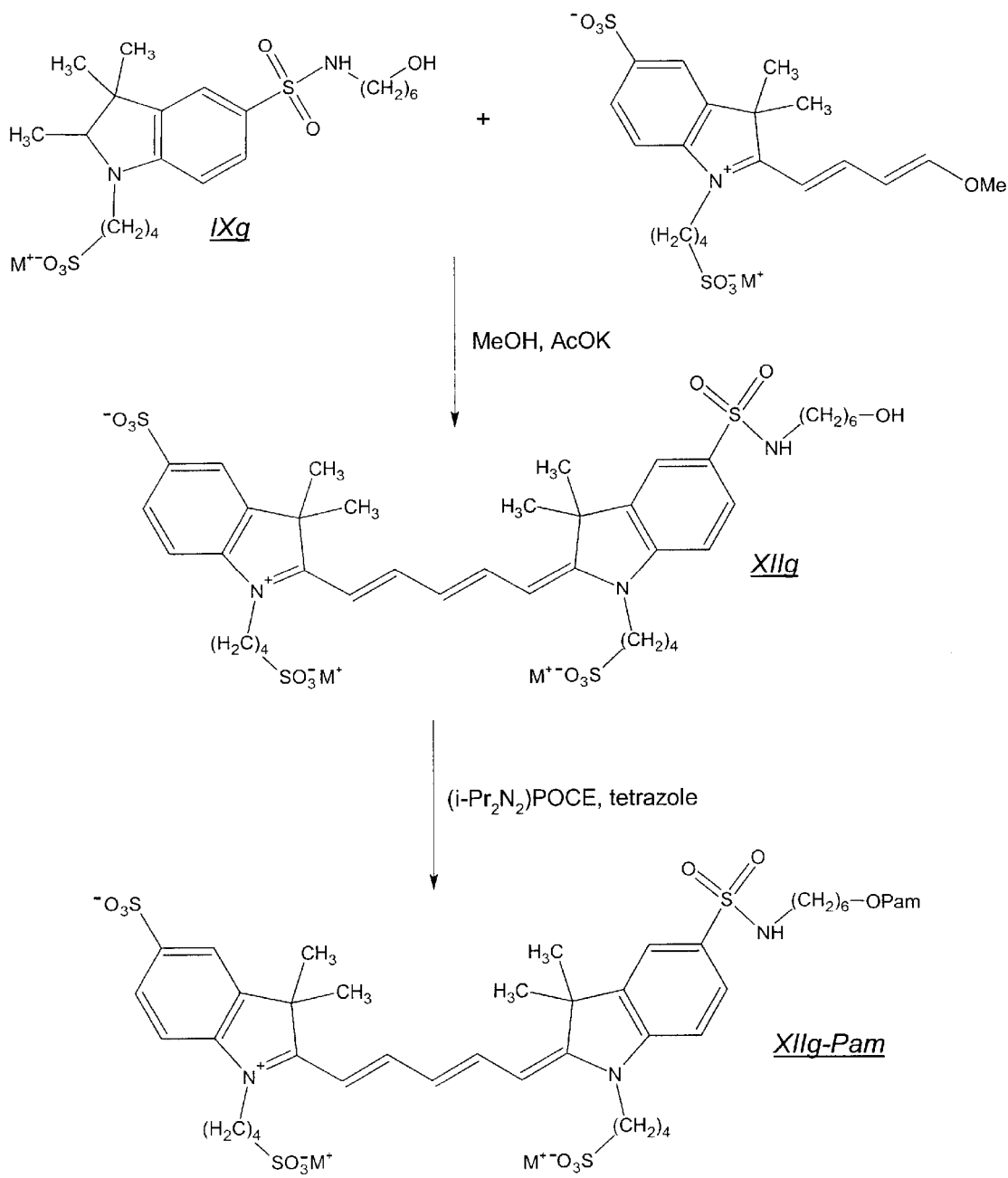
FIG. 14 outlines the preparation of XIIg and XIIg-Pam.
Figure 15:
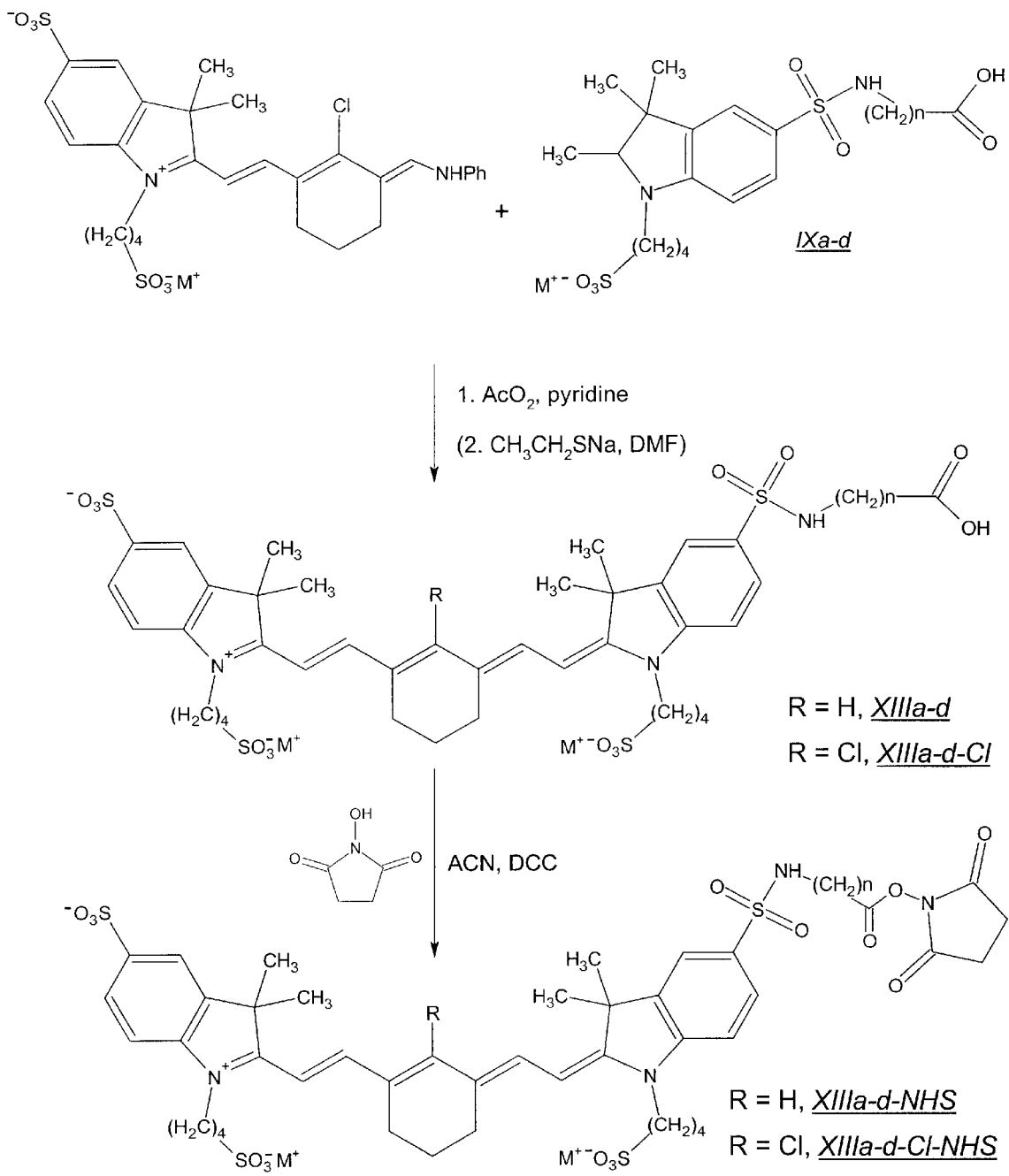
FIG. 15 outlines the preparation of XIIIa–d, XIIIa–d-Cl, XIIIa–d-NHS, and XIIIa–d-Cl-NHS.
Figure 16:
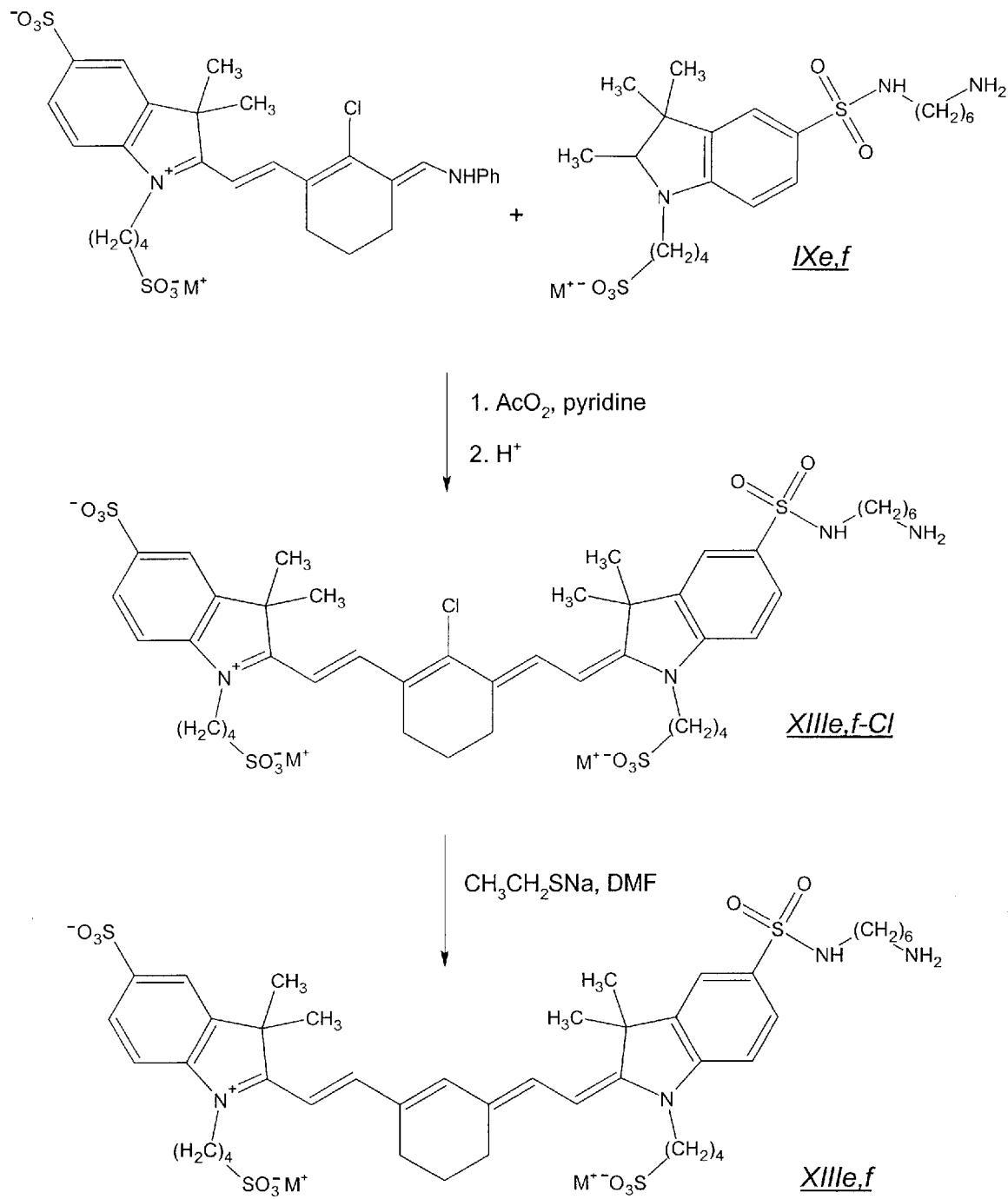
FIG. 16 outlines the preparation of XIIIe and XIIIf.
Figure 17:
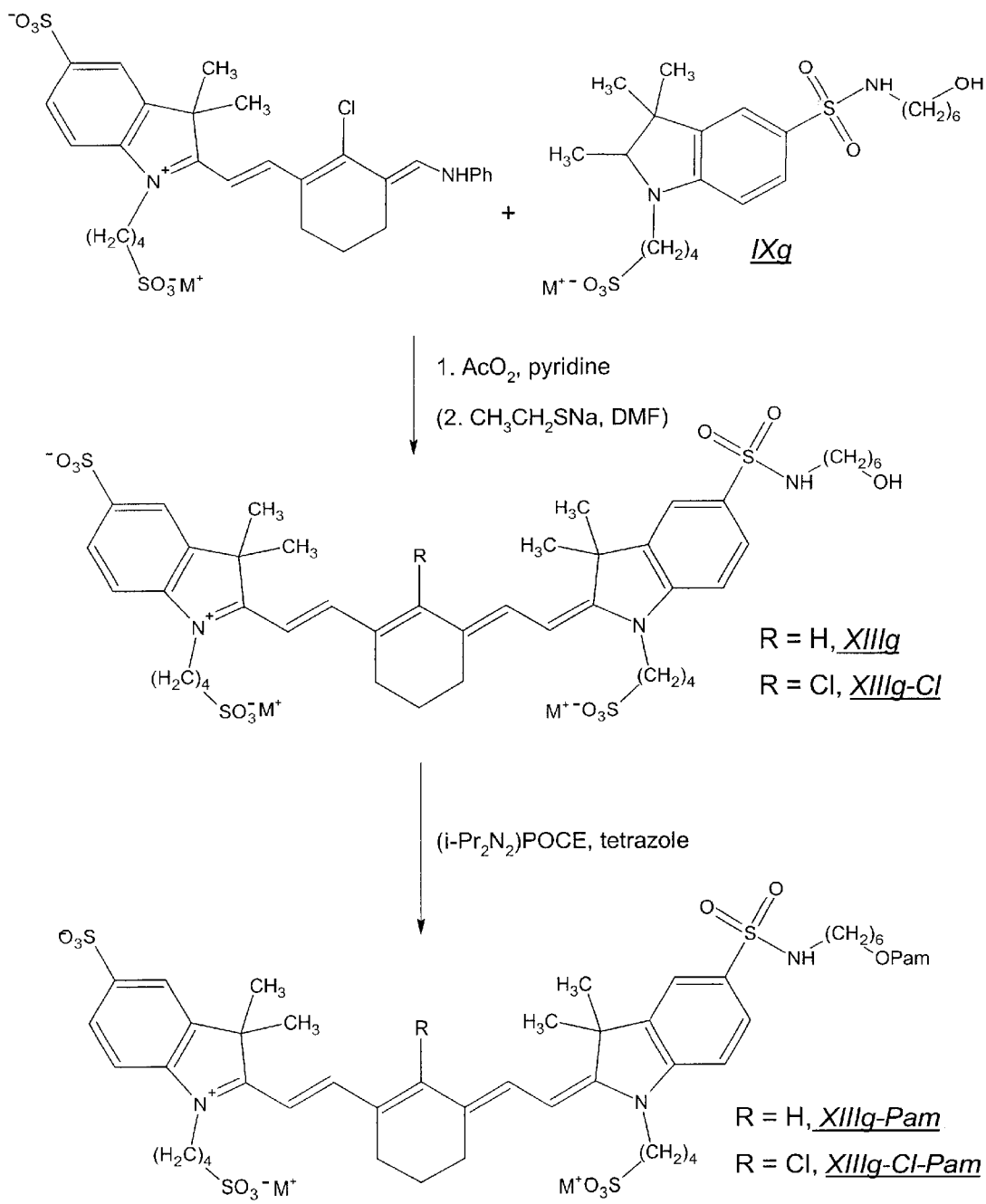
FIG. 17 outlines the preparation of XIIIg, XIIIg-Cl, XIIIg-Pam, and XIII-Cl-Pam.
Figure 18:
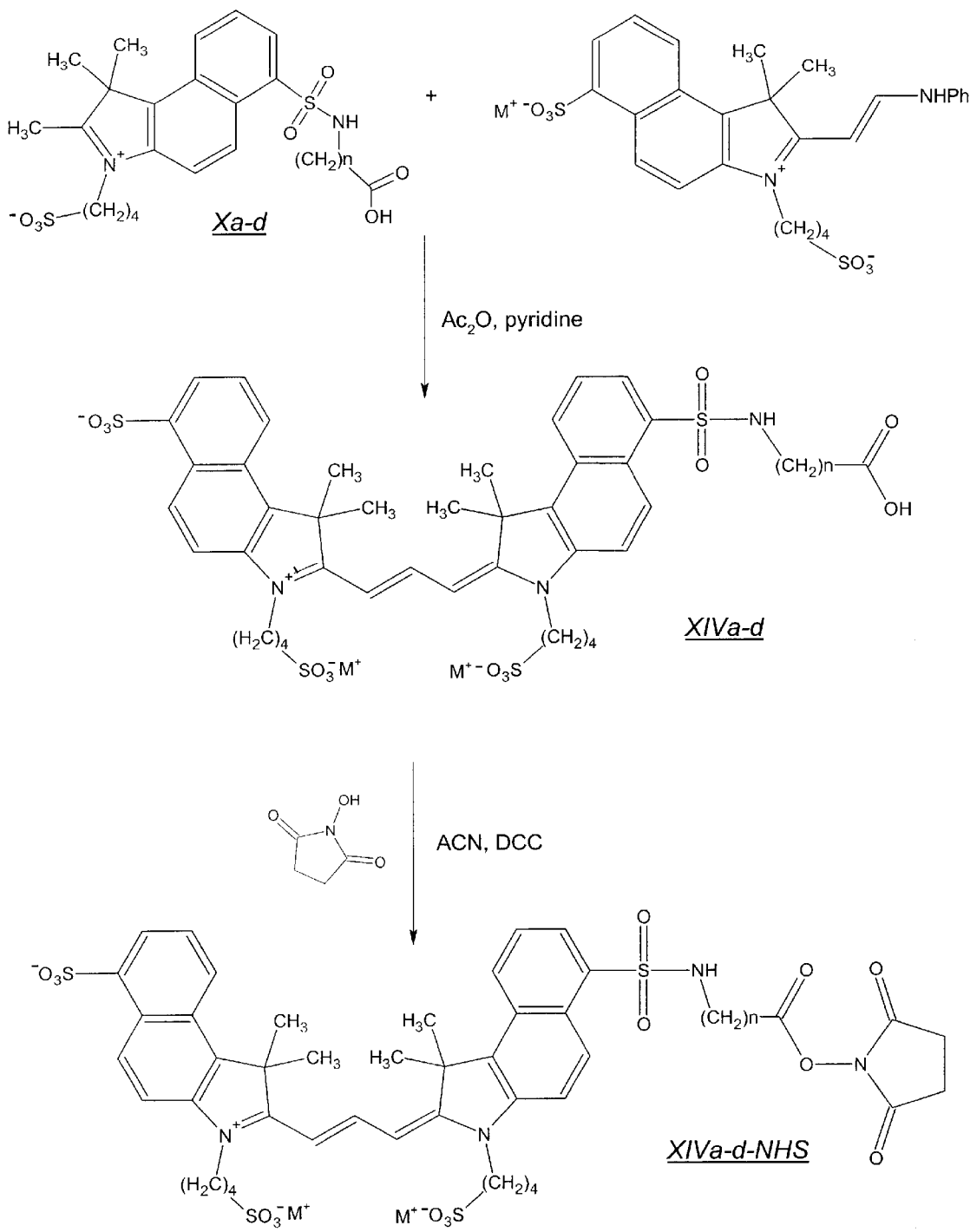
FIG. 18 outlines the preparation of XIVa–d and XIVa–d-NHS.
Figure 19:
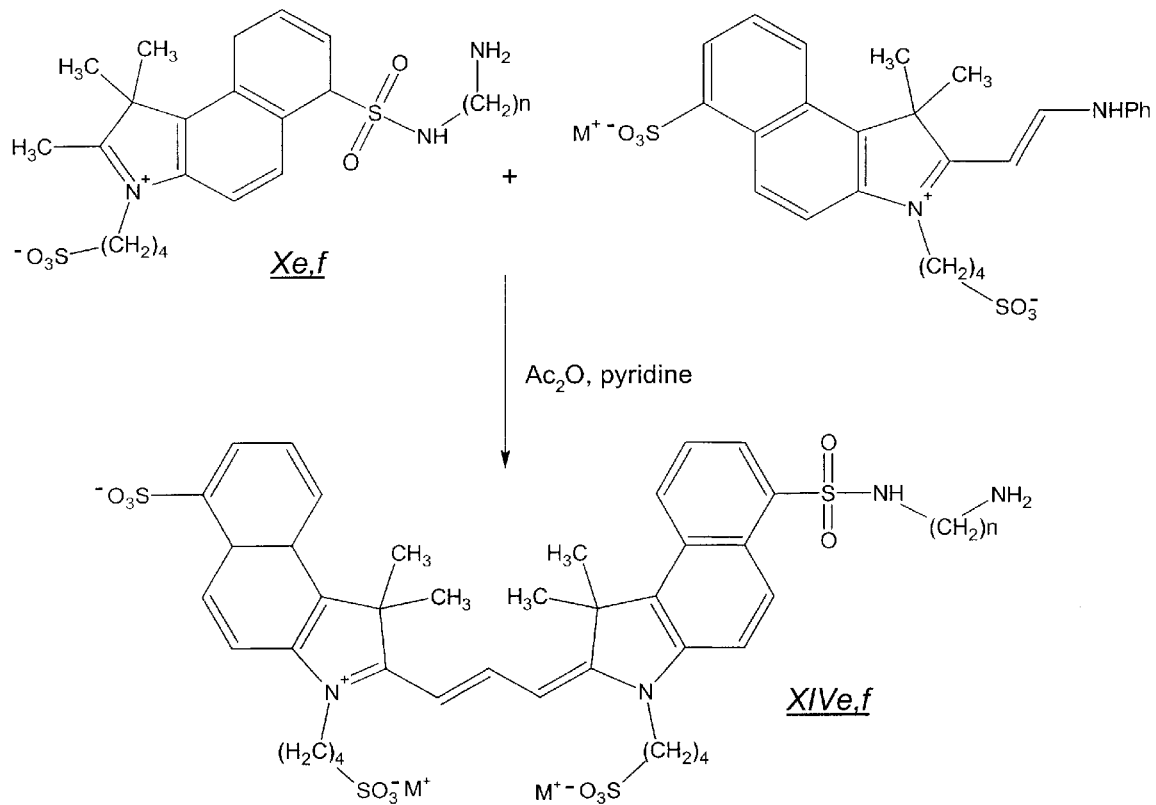
FIG. 19 outlines the preparation of XIVe and XIVf.
Figure 20:
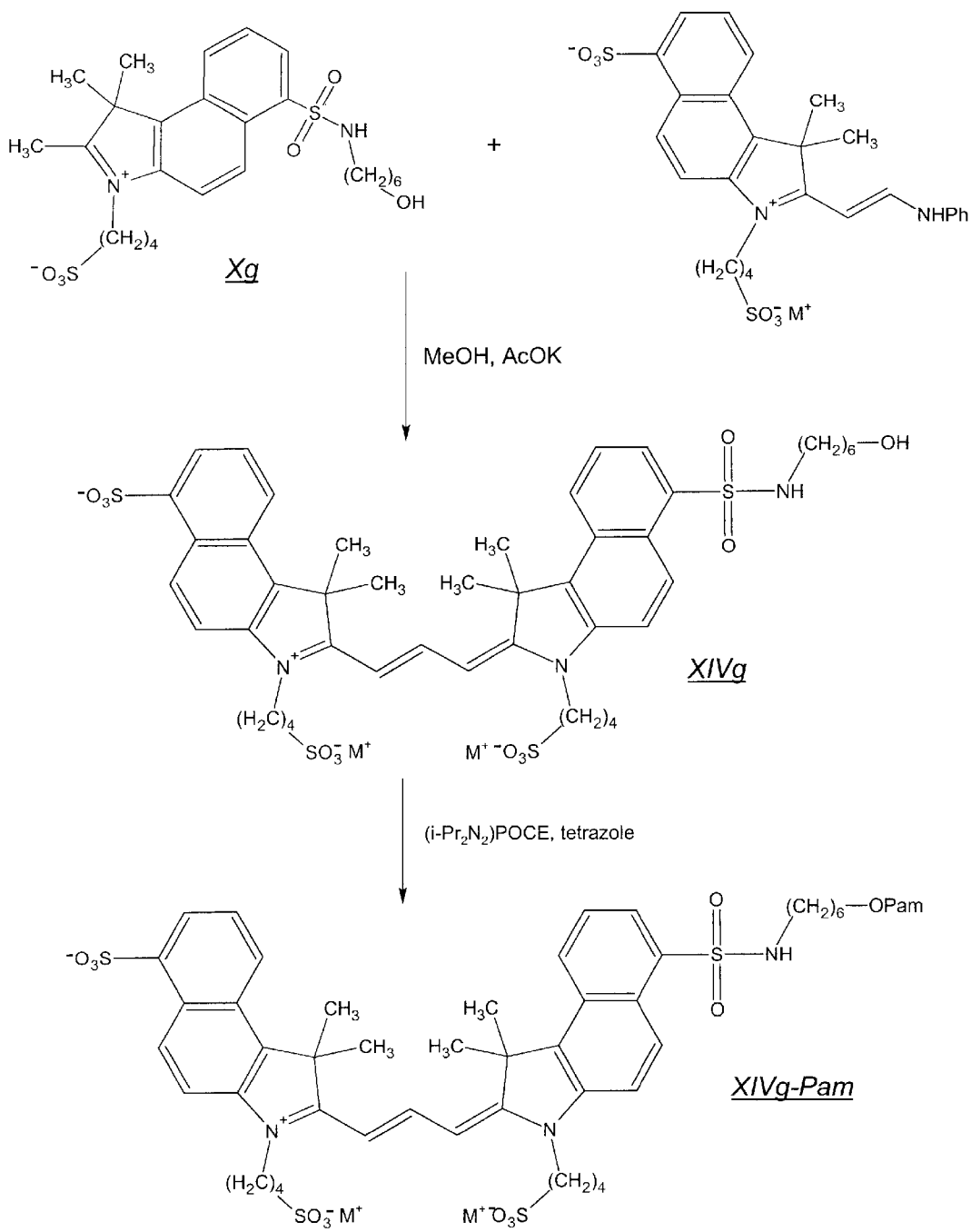
FIG. 20 outlines the preparation of XIVg and XIVg-Pam.
Figure 21:
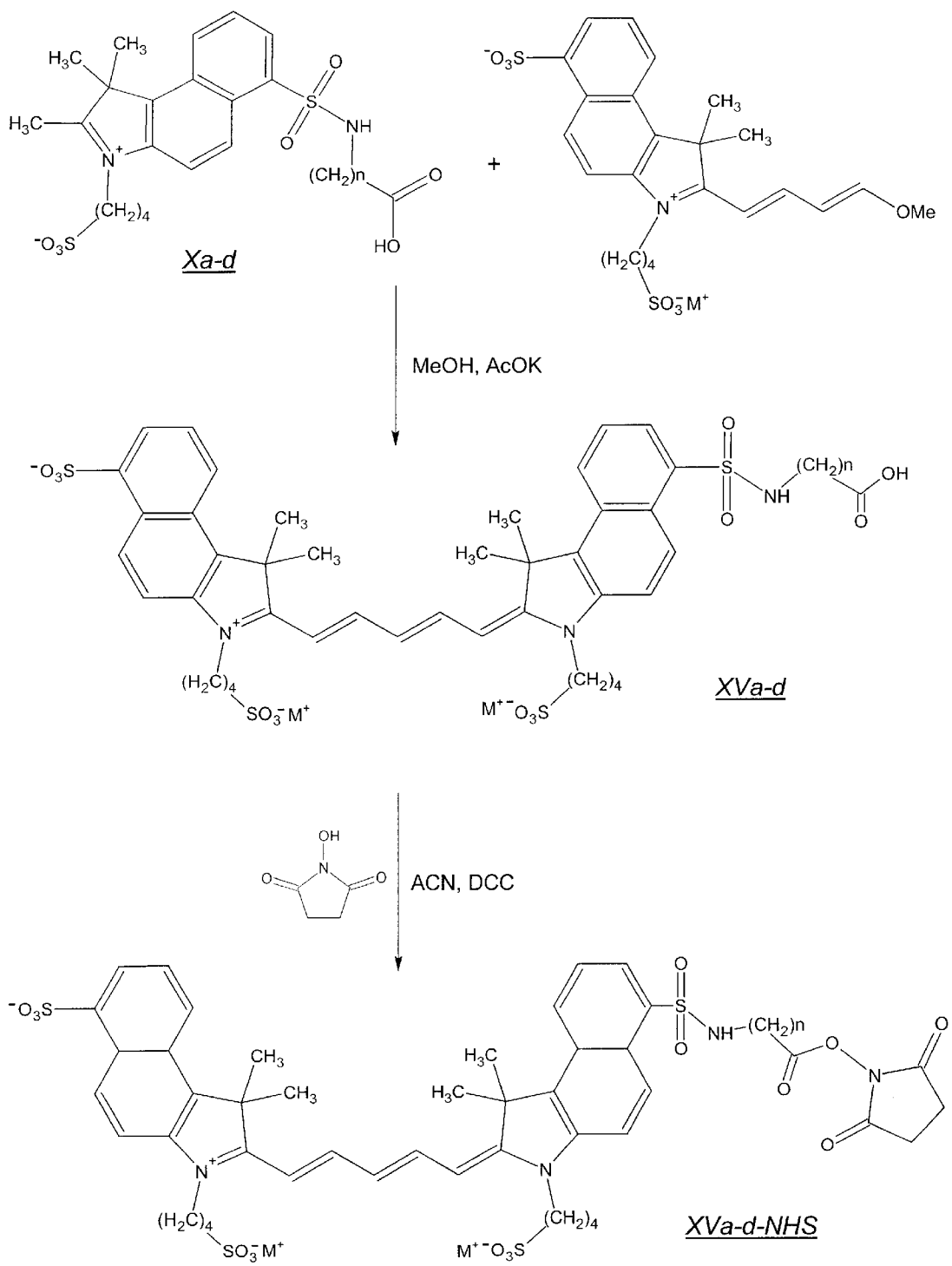
FIG. 21 outlines the preparation of XVa–d, and XVa–d-NHS.
Figure 22:
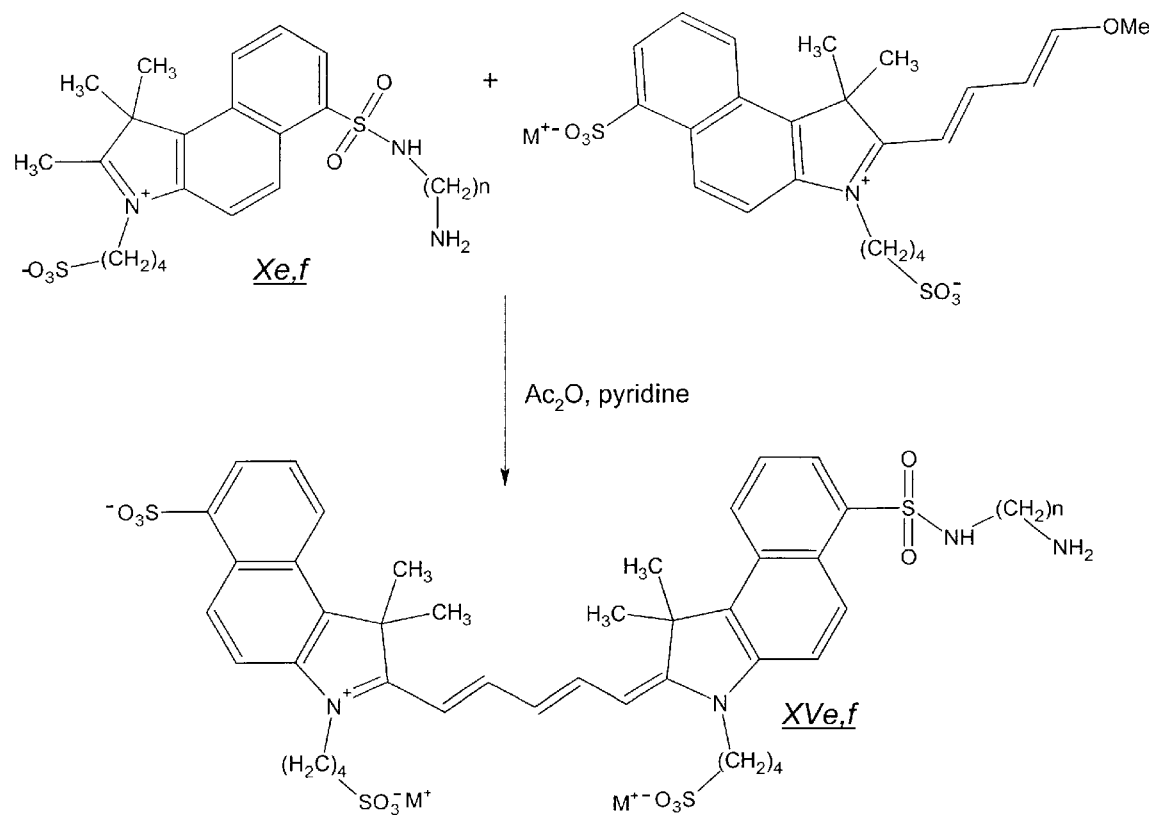
FIG. 22 outlines the preparation of XVe and XVf.
Figure 23:
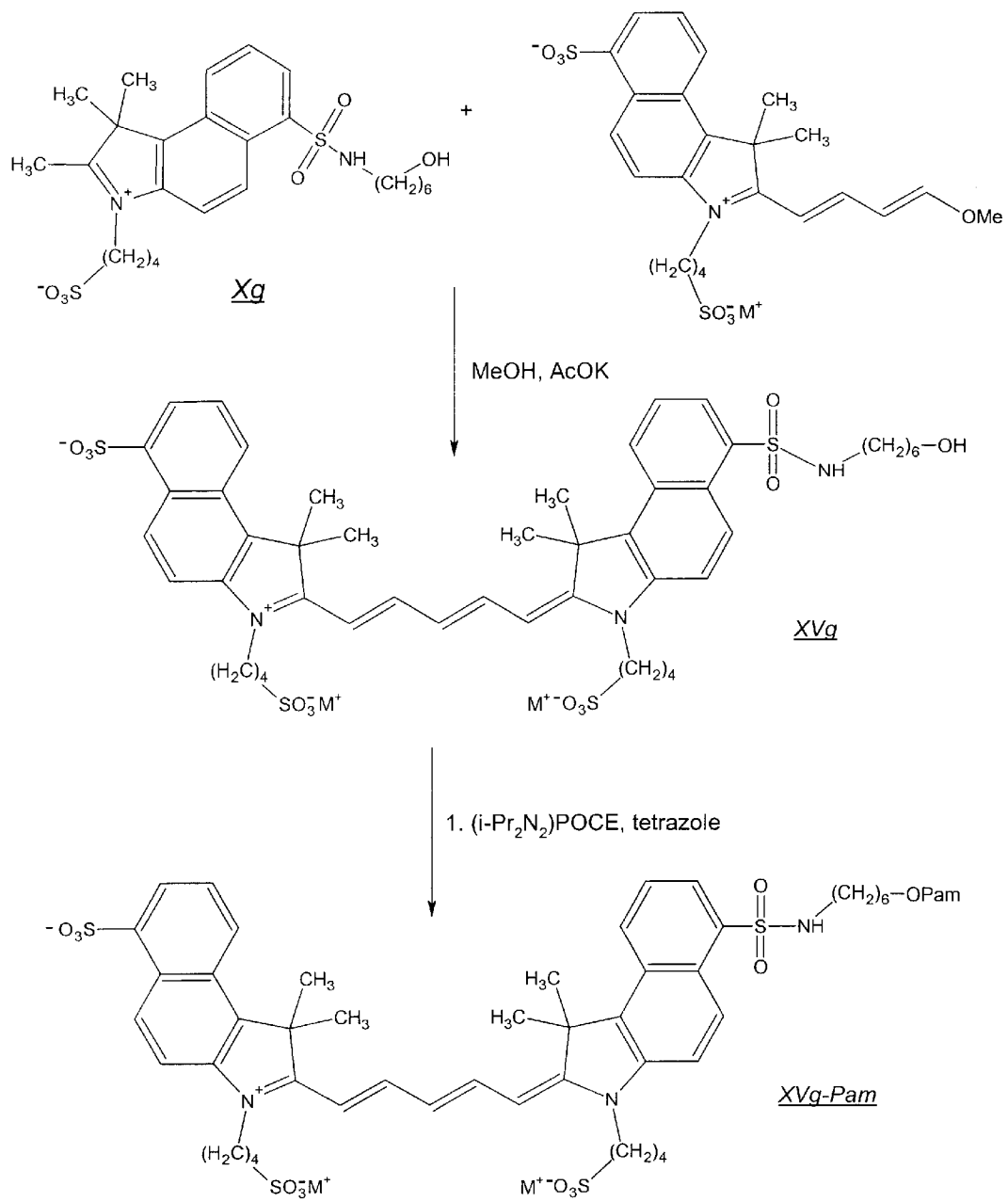
FIG. 23 outlines the preparation of XVg and XVg-Pam.
Figure 24:
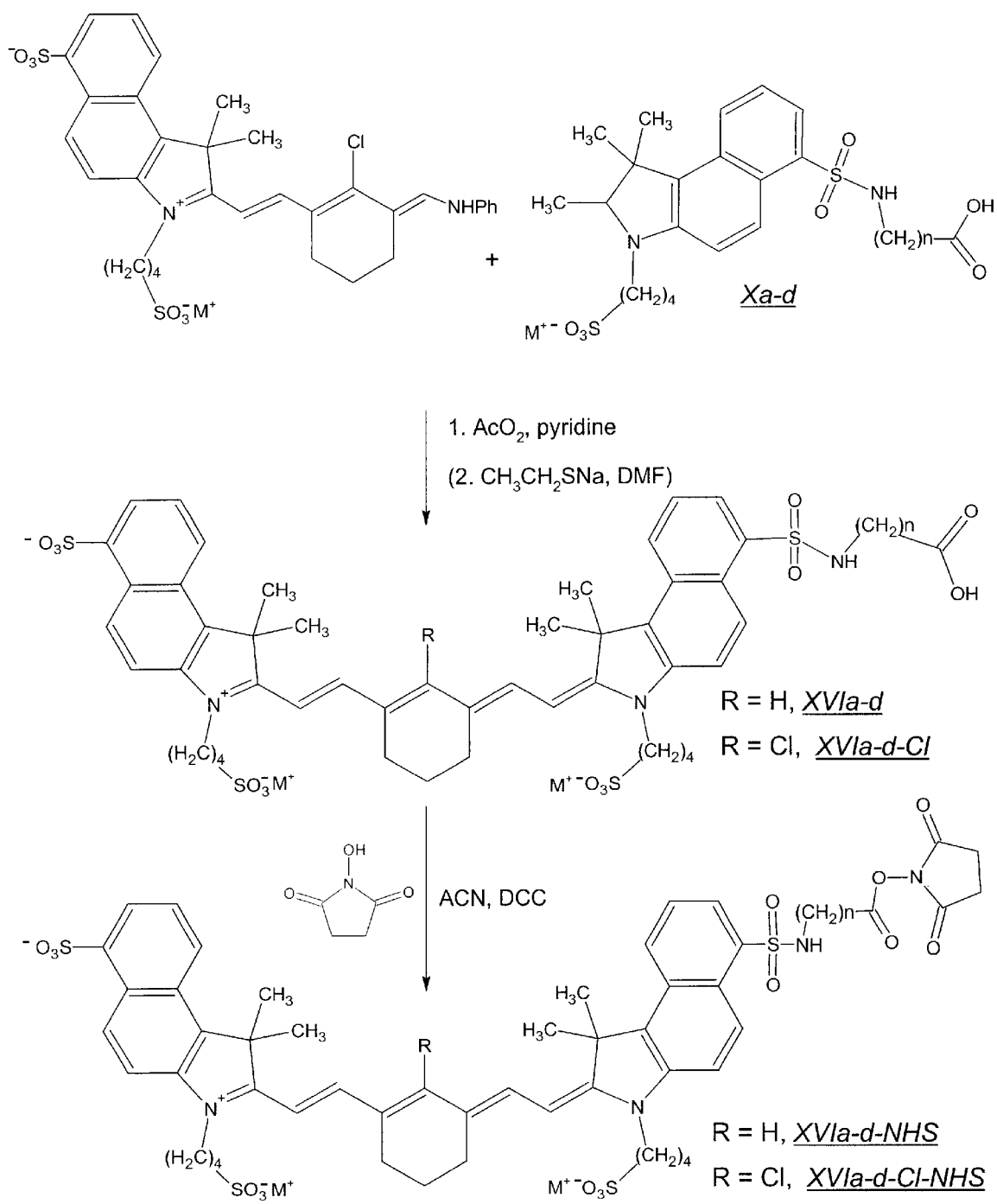
FIG. 24 outlines the preparation of XVIa–d, XVIa–d-Cl, XVIa–d-NHS, and XVIa–d-Cl-NHS.
Figure 25:
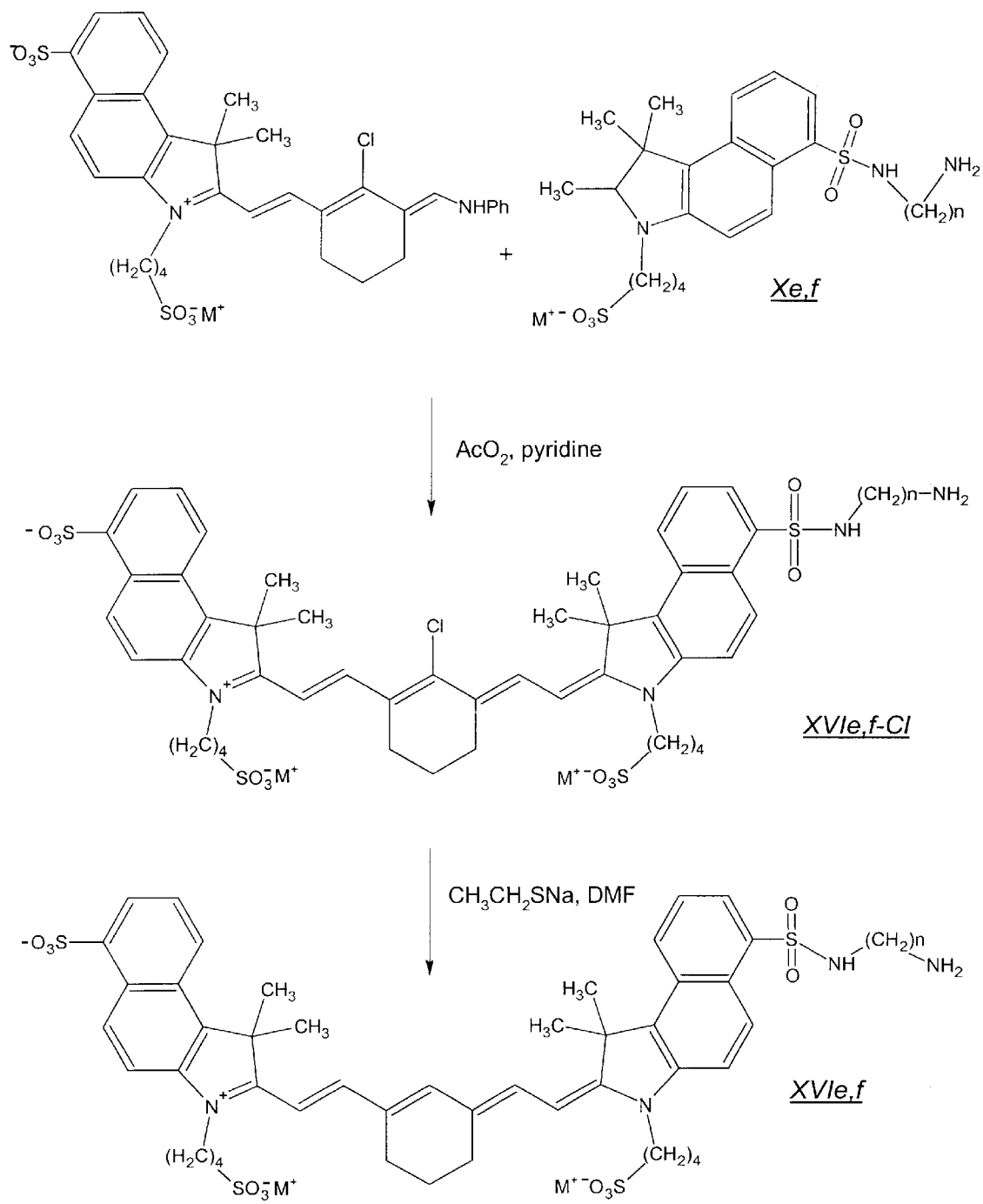
FIG. 25 outlines the preparation of XVIe, XVIf, XVIe-Cl, and XVIf-Cl.
Figure 26:
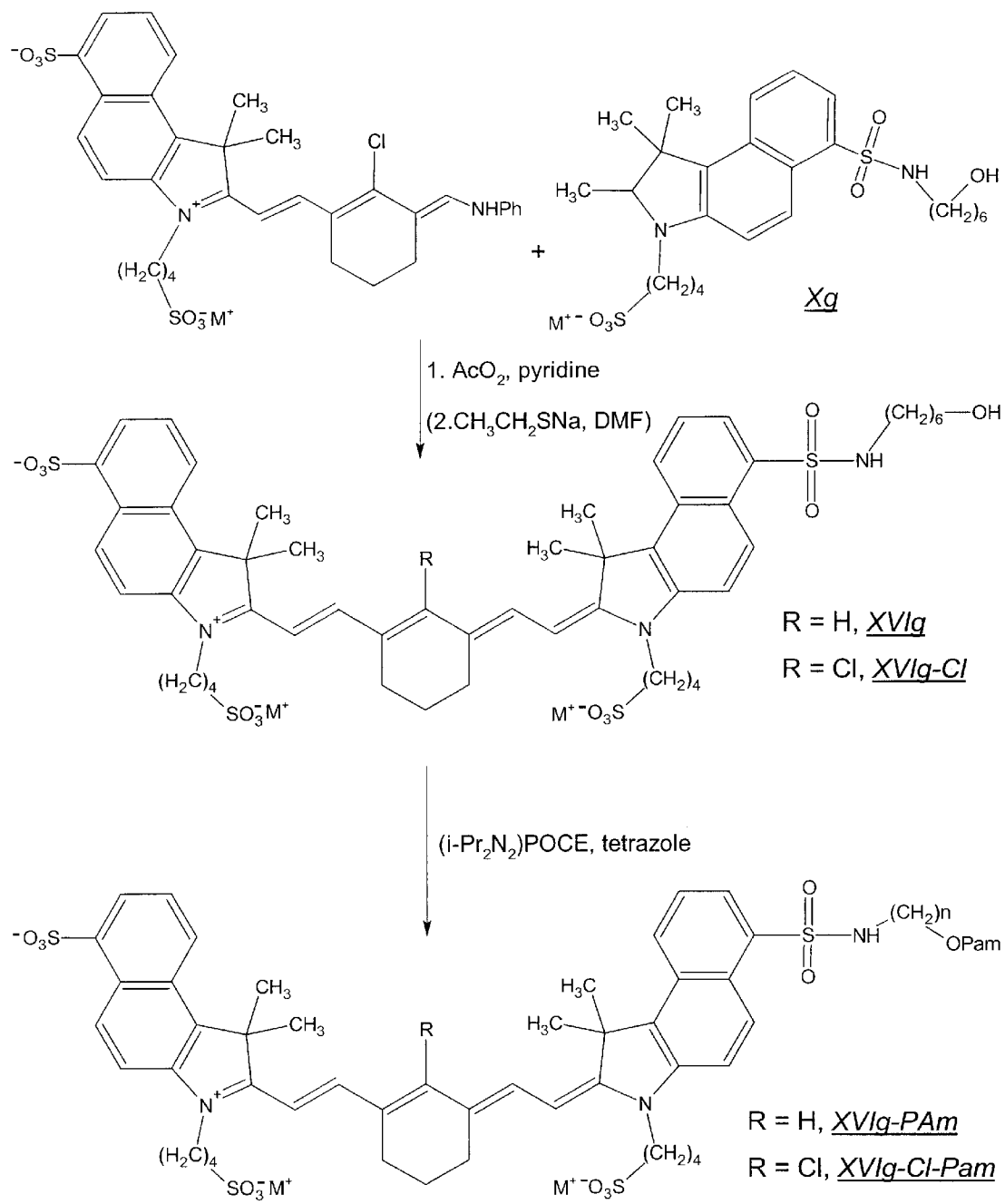
FIG. 26 outlines the preparation of XVIg, XVIg-Cl, XVIg-Pam, and XVIg-Cl-Pam.
Figure 27:
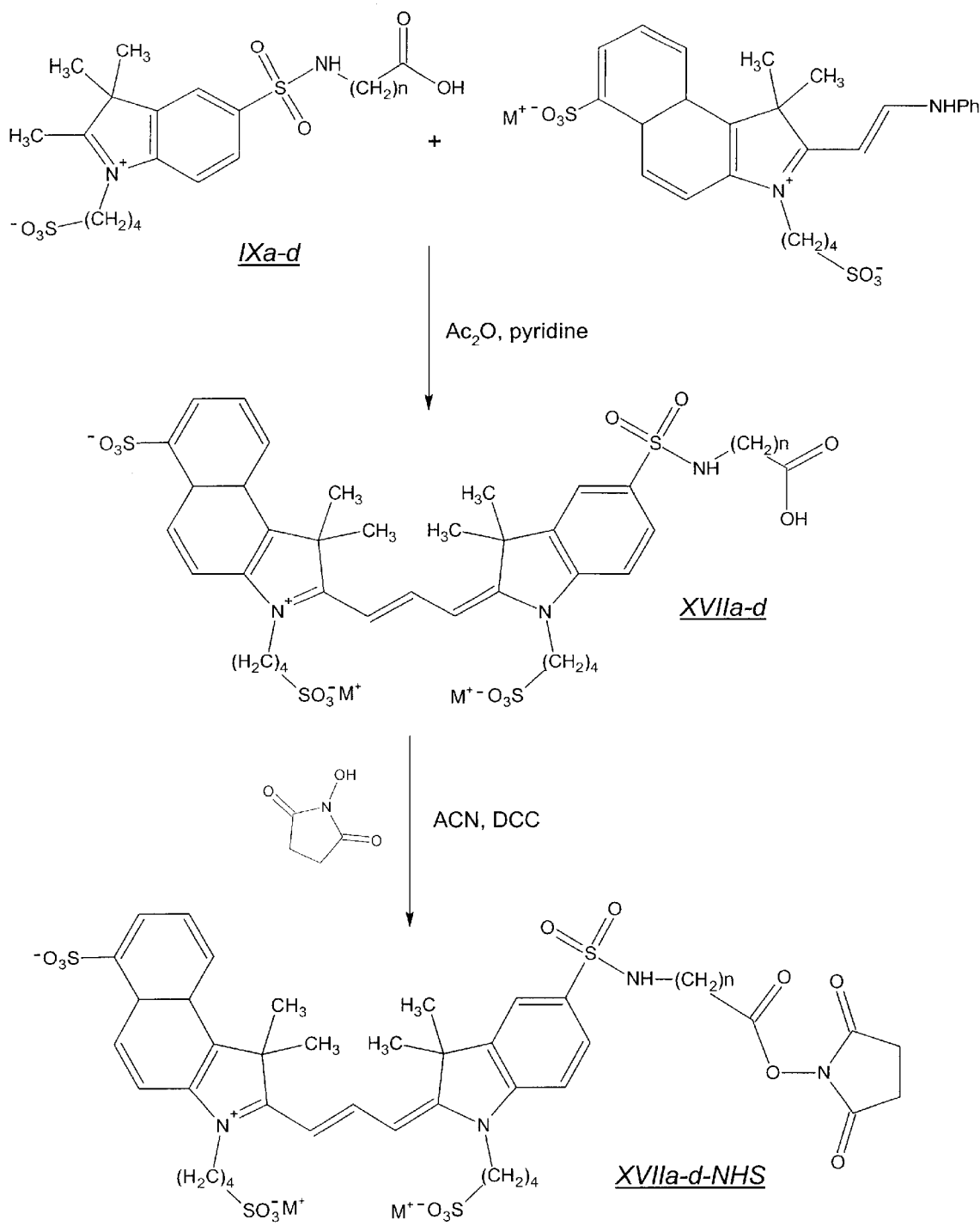
FIG. 27 outlines the preparation of XVIIa–d and XVIIa–d-NHS.
Figure 28:
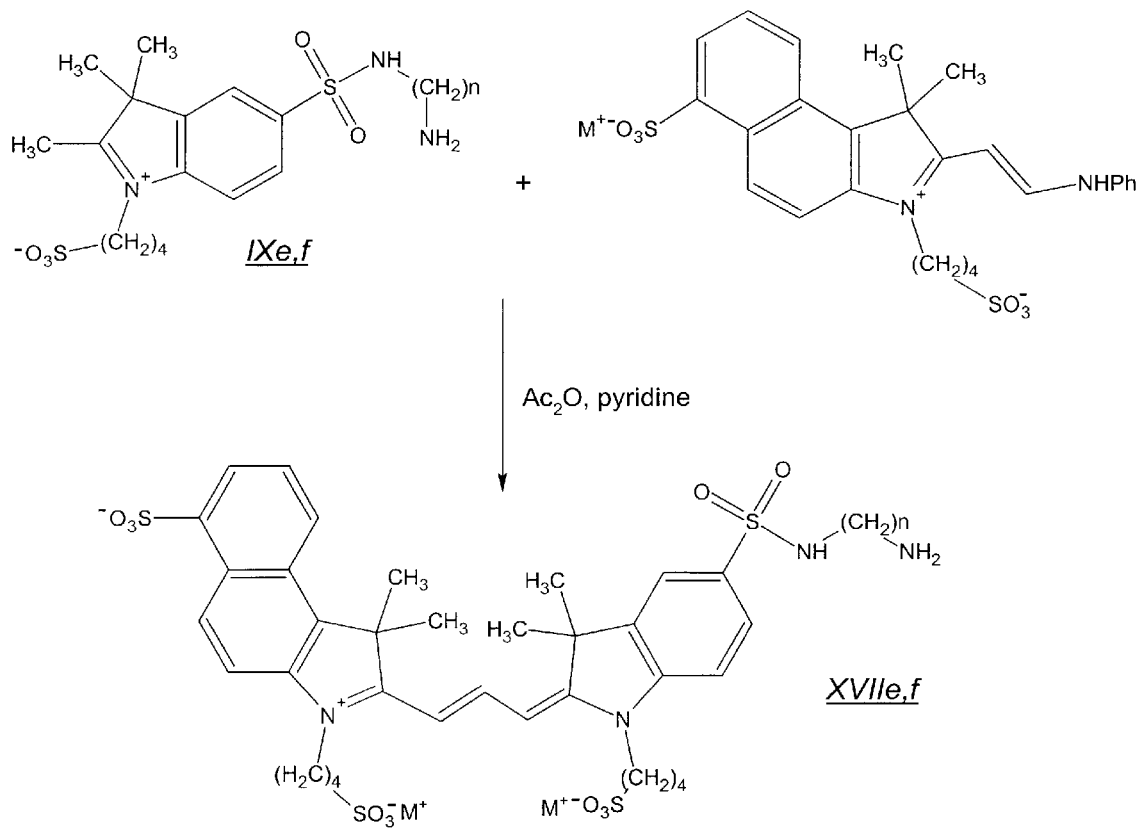
FIG. 28 outlines the preparation of XVIIe and XVIIf.
Figure 29:
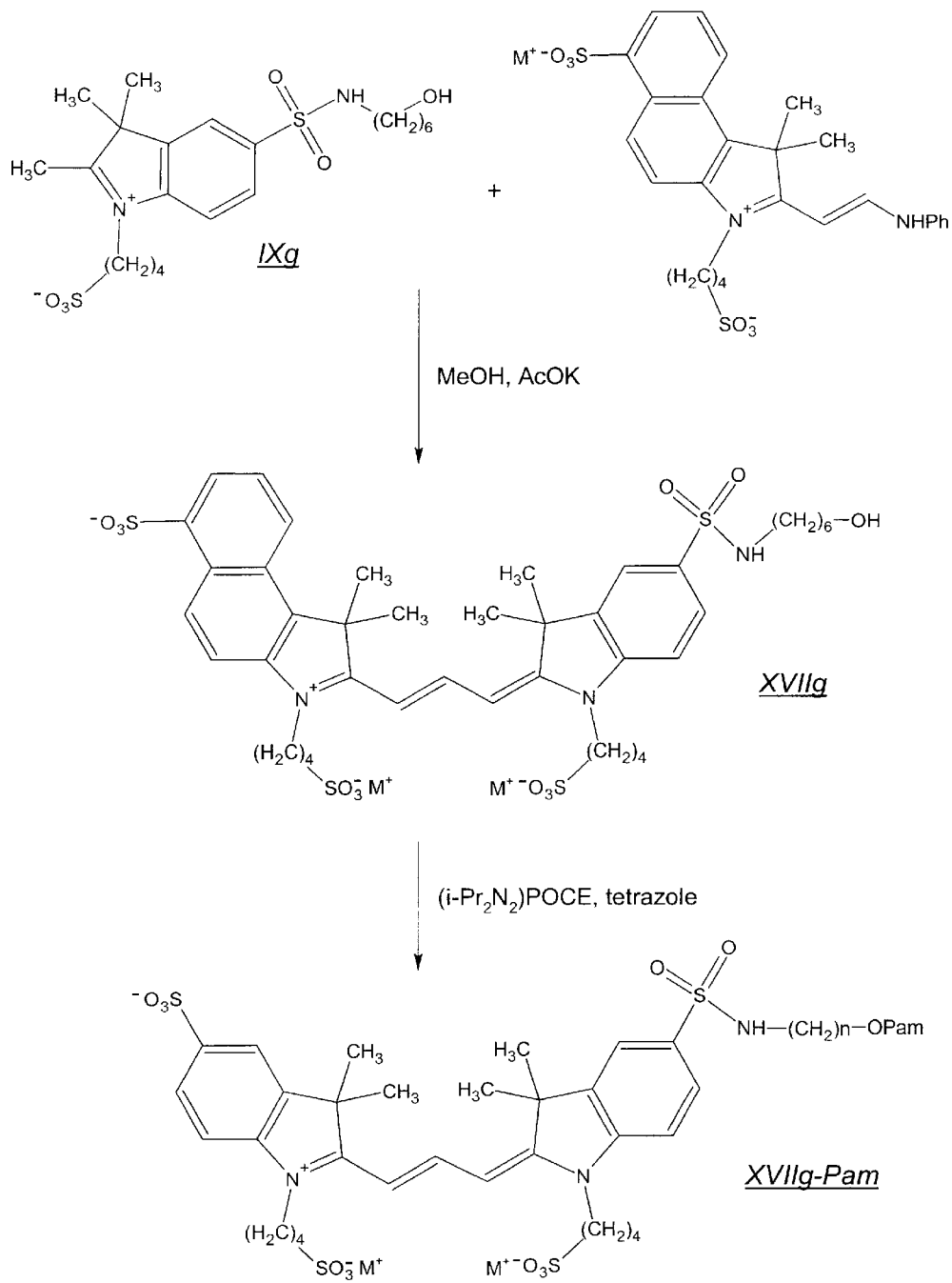
FIG. 29 outlines the preparation of XVIIg and XVIIg-Pam.
Figure 30:
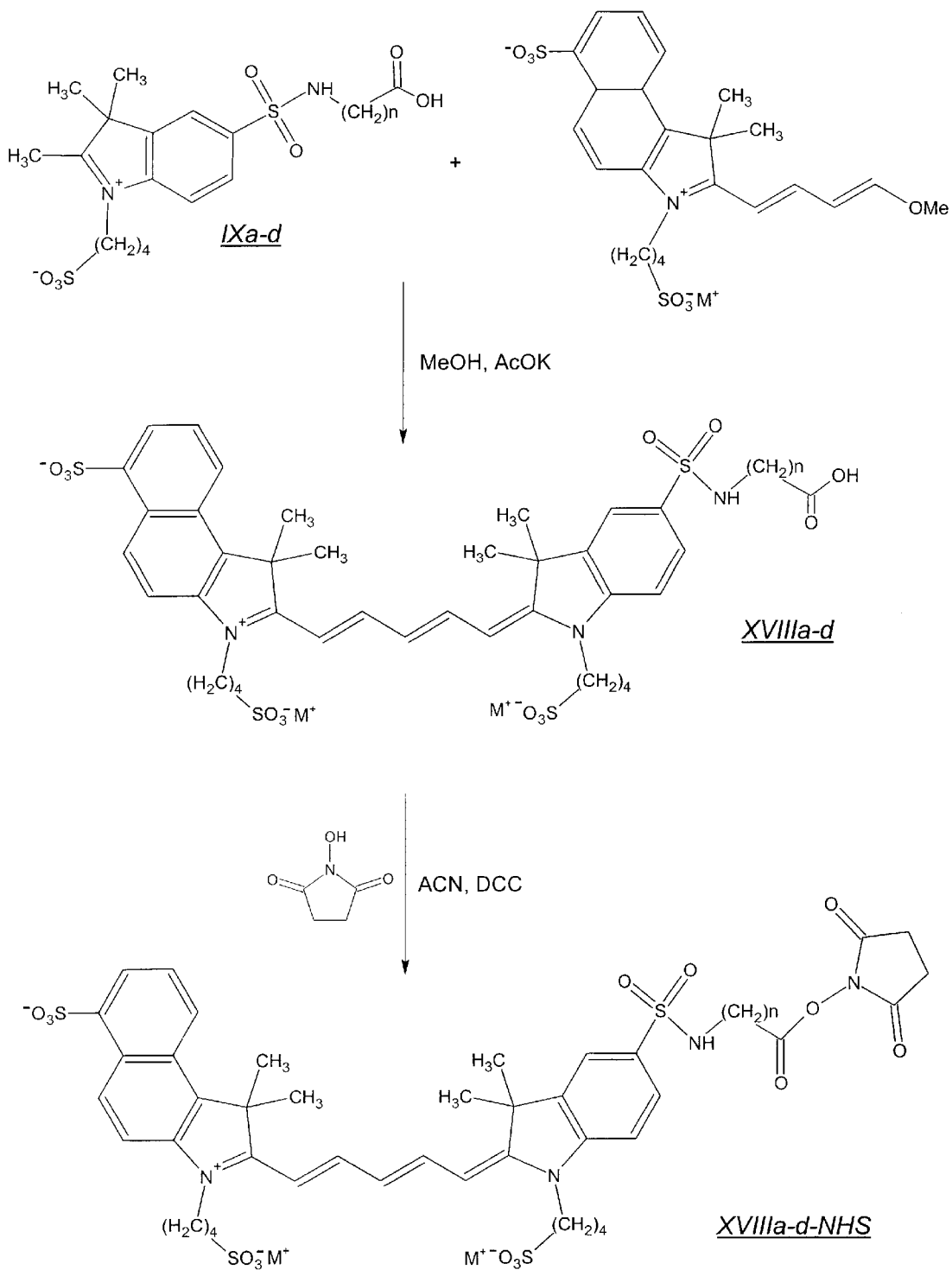
FIG. 30 outlines the preparation of XVIIIa–d and XVIIa–d-NHS.
Figure 31:
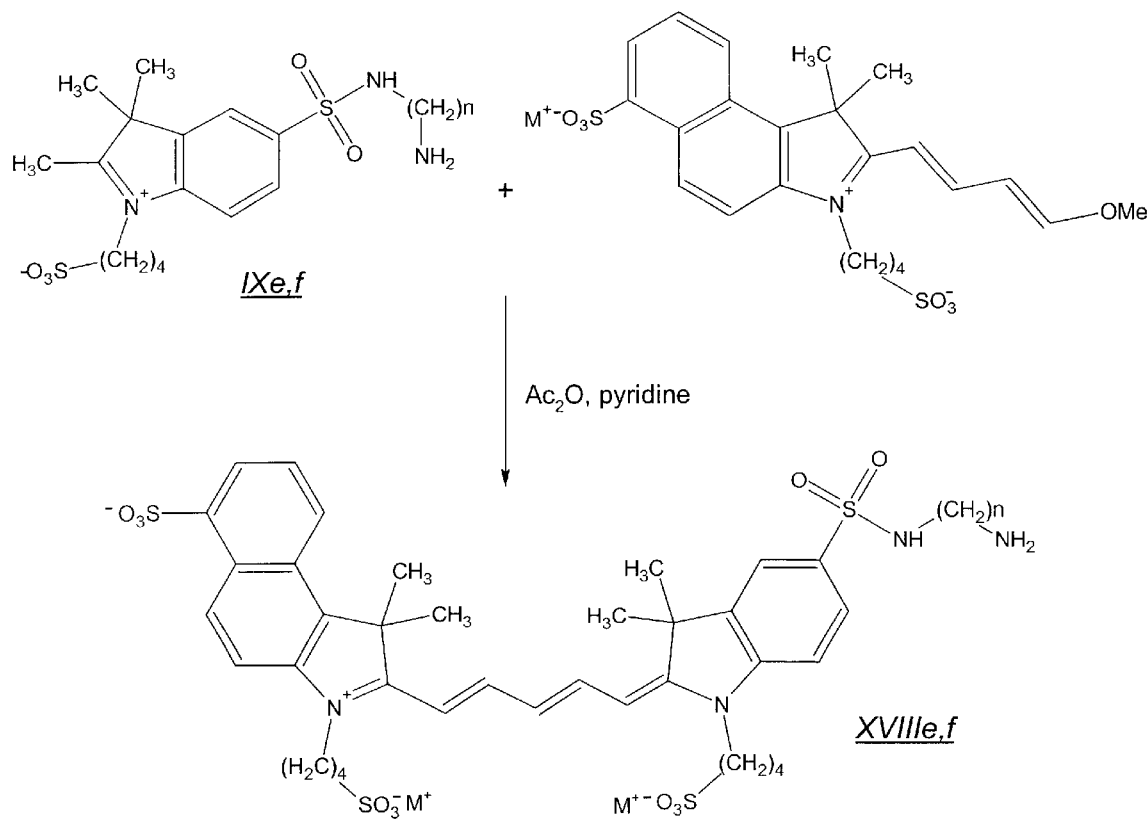
FIG. 31 outlines the preparation of XVIIIe and XVIIIf.
Figure 32:
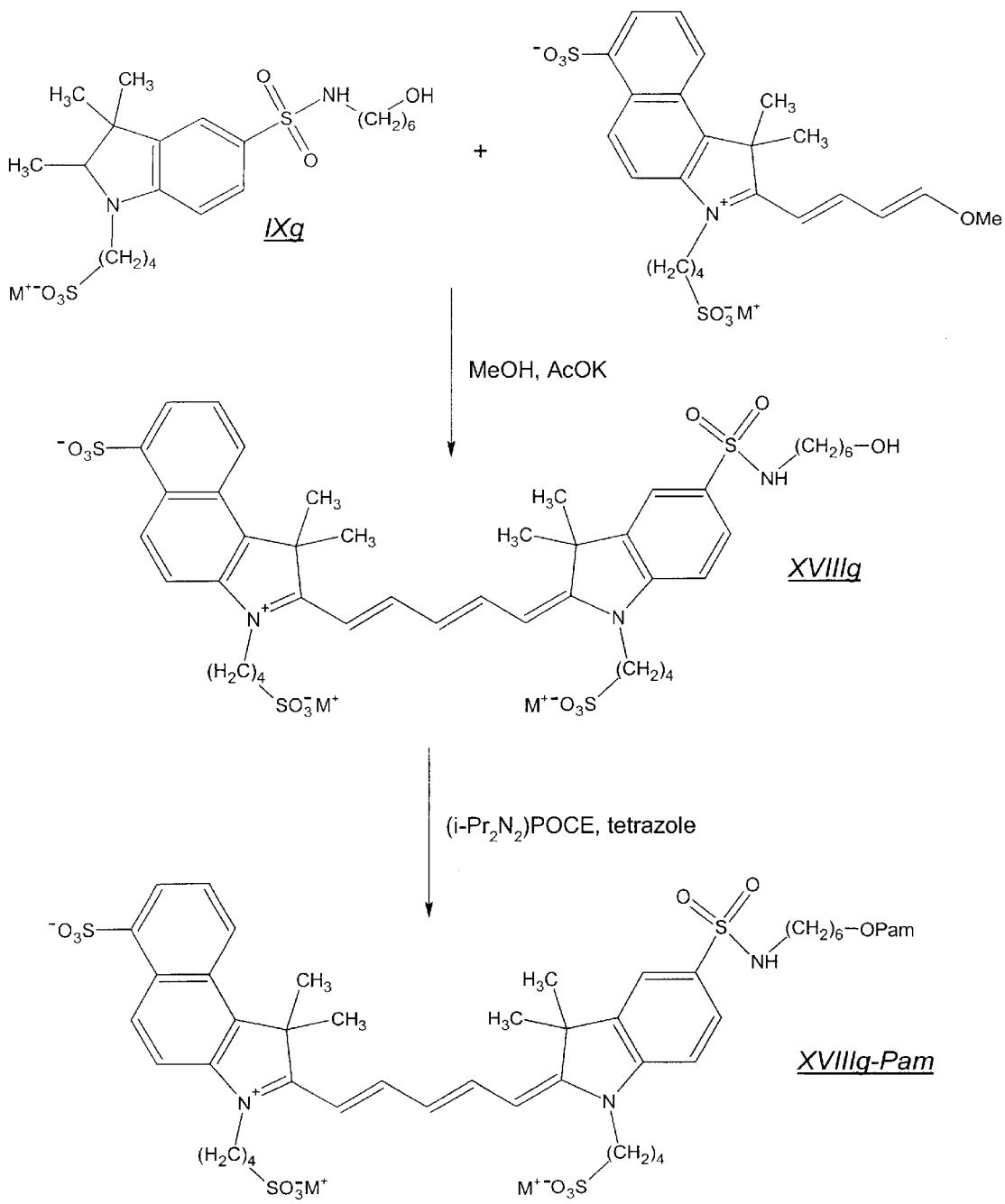
FIG. 32 outlines the preparation of XVIIIg and XVIIIg-Pam.
Figure 33:
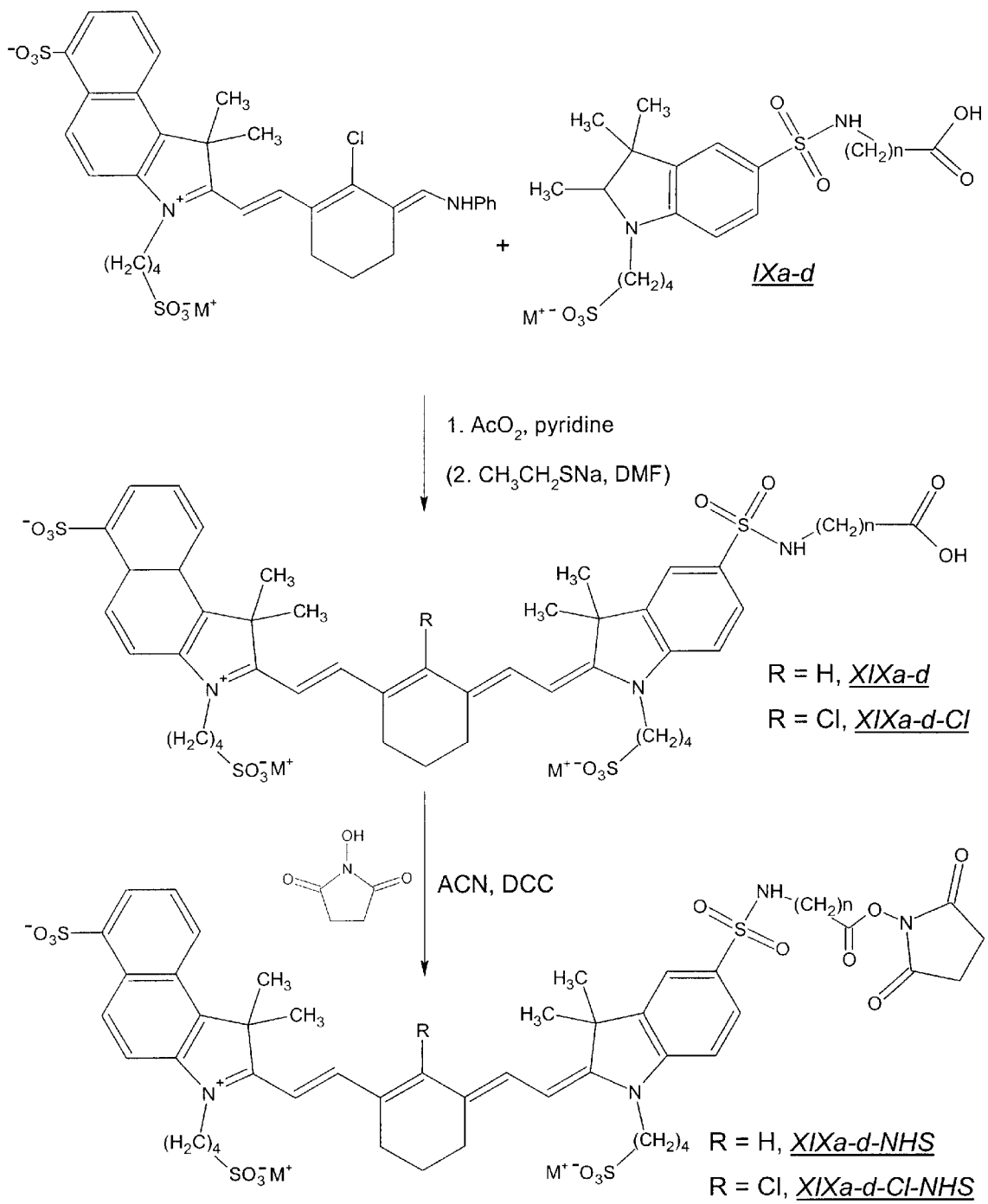
FIG. 33 outlines the preparation of XIXa–d, XIXa–d-Cl, XIXa–d-NHS, and XIXa–d-Cl-NHS.
Figure 34:
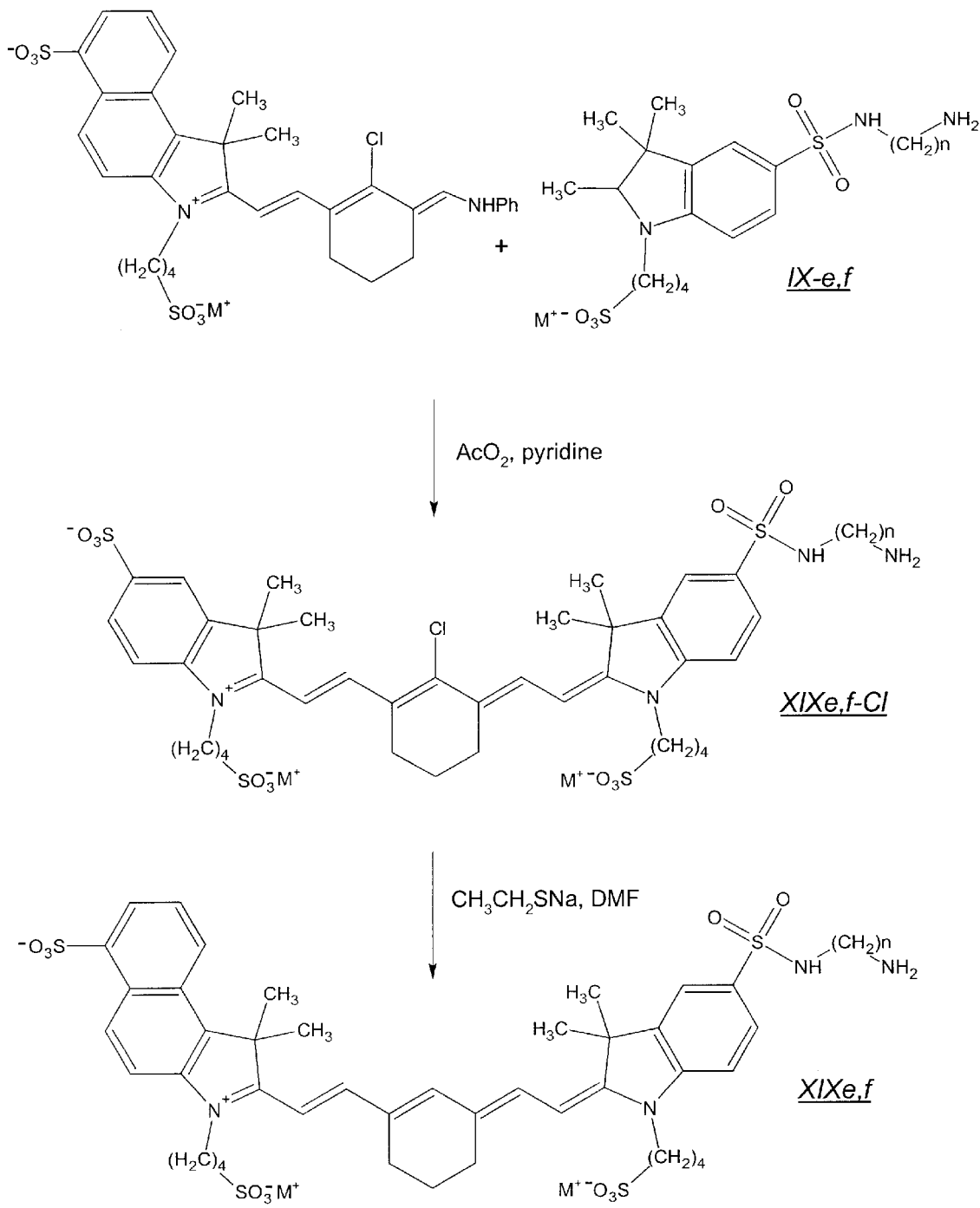
FIG. 34 outlines the preparation of XIXe, XIXf, XIXe-Cl, XIXf, and XIXf-Cl.
Figure 35:
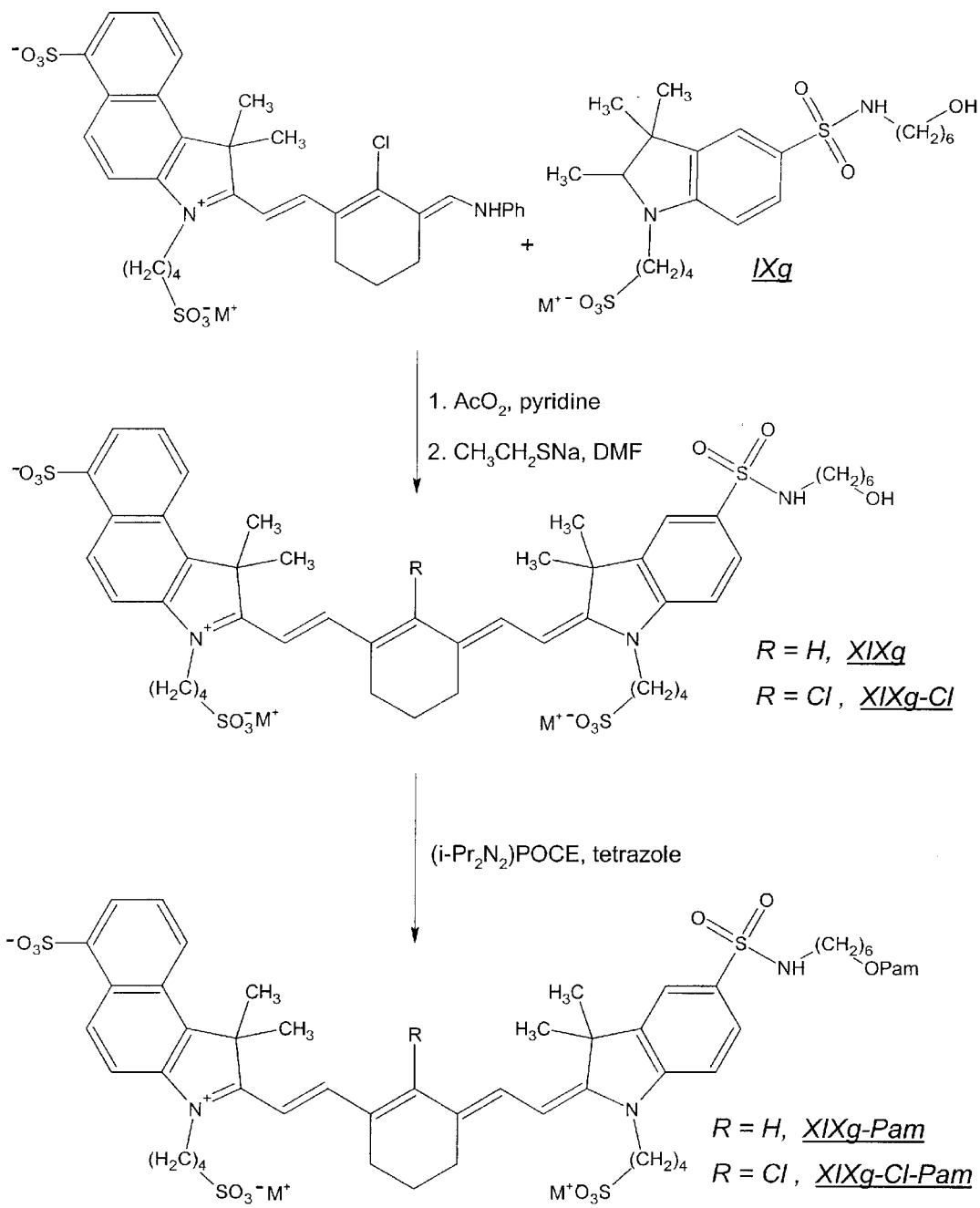
FIG. 35 outlines the preparation of XIXg, XIXg-Cl, XIXg-Pam, and XIXg—Cl-Pam.
Figure 36:
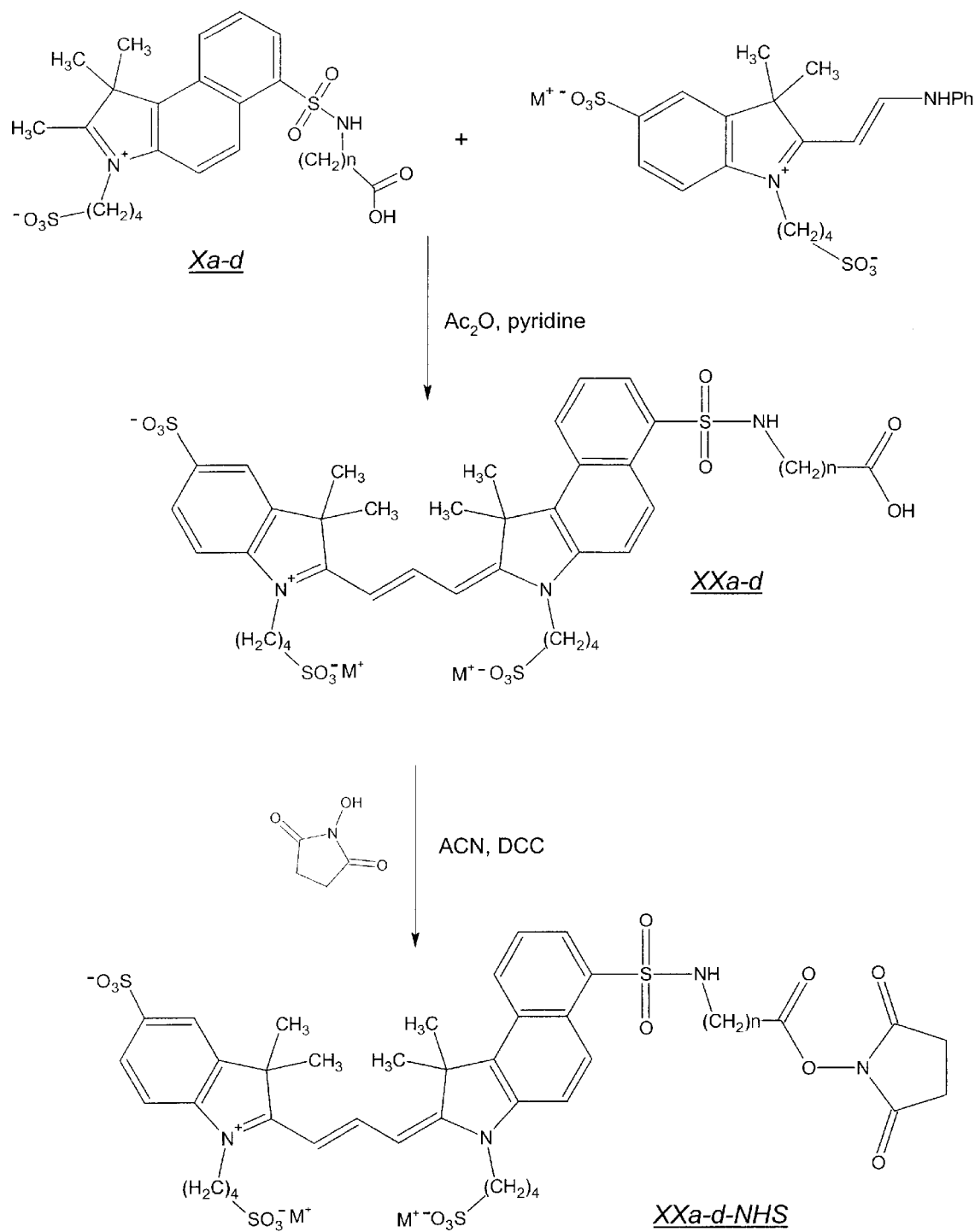
FIG. 36 outlines the preparation of XXa–d, and XXa–d-NHS.
Figure 37:
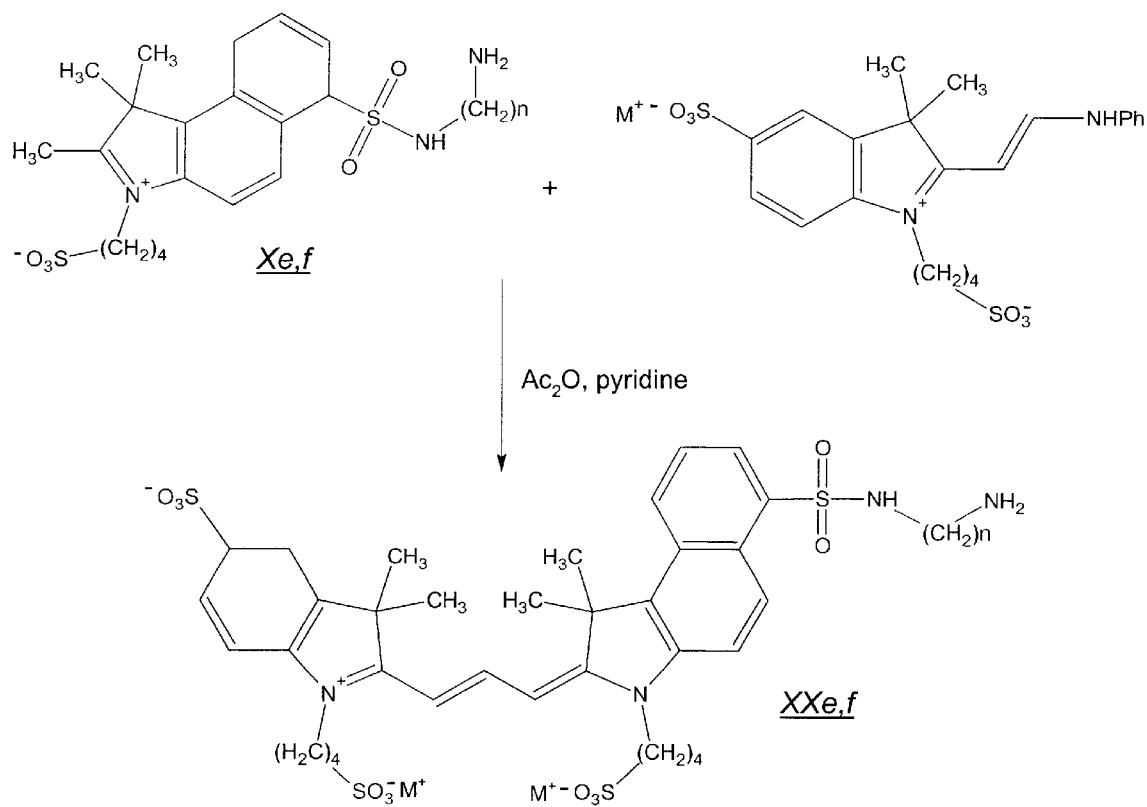
FIG. 37 outlines the preparation of XXe and XXf.
Figure 38:
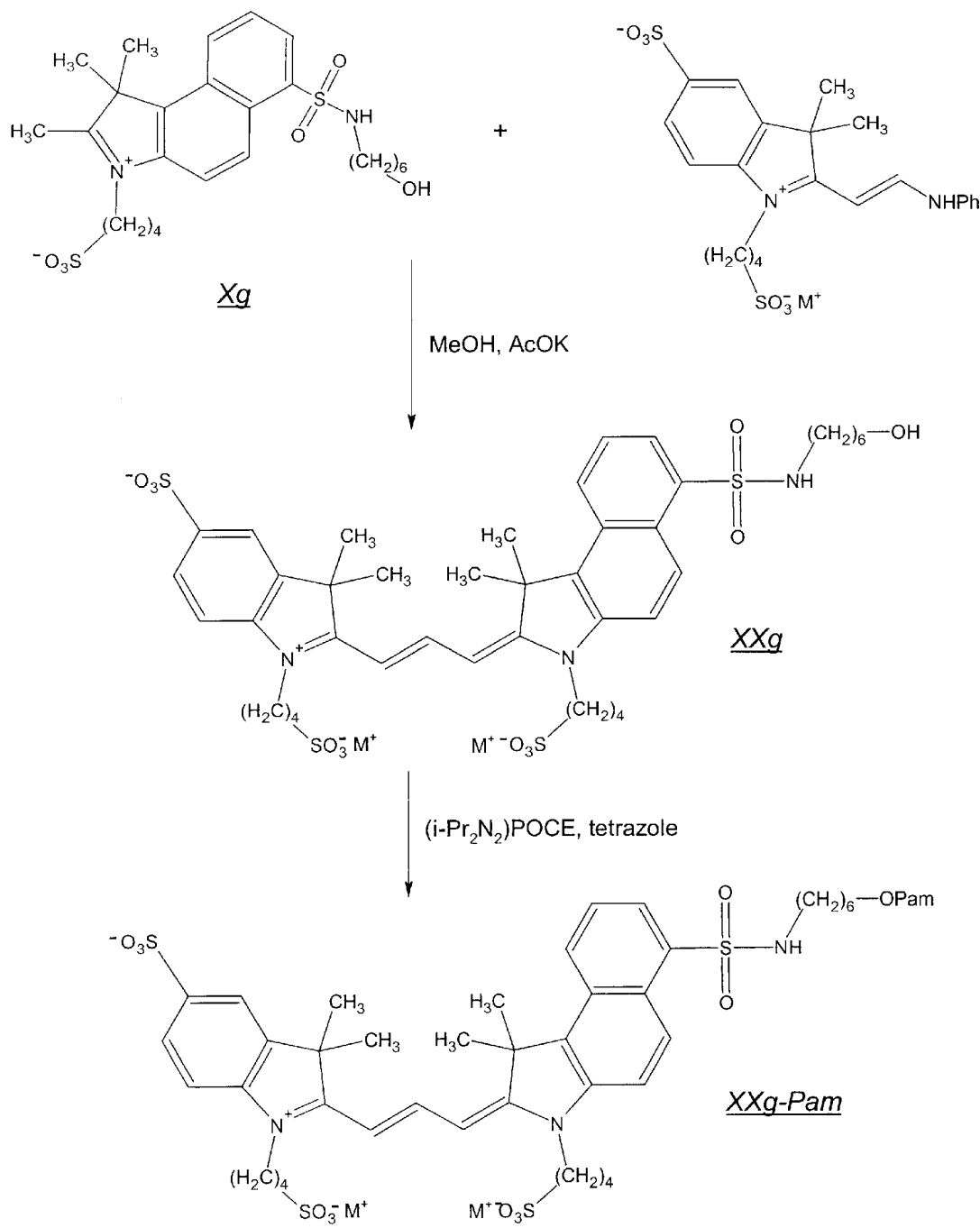
FIG. 38 outlines the preparation of XXg and XXg-Pam.
Figure 39:
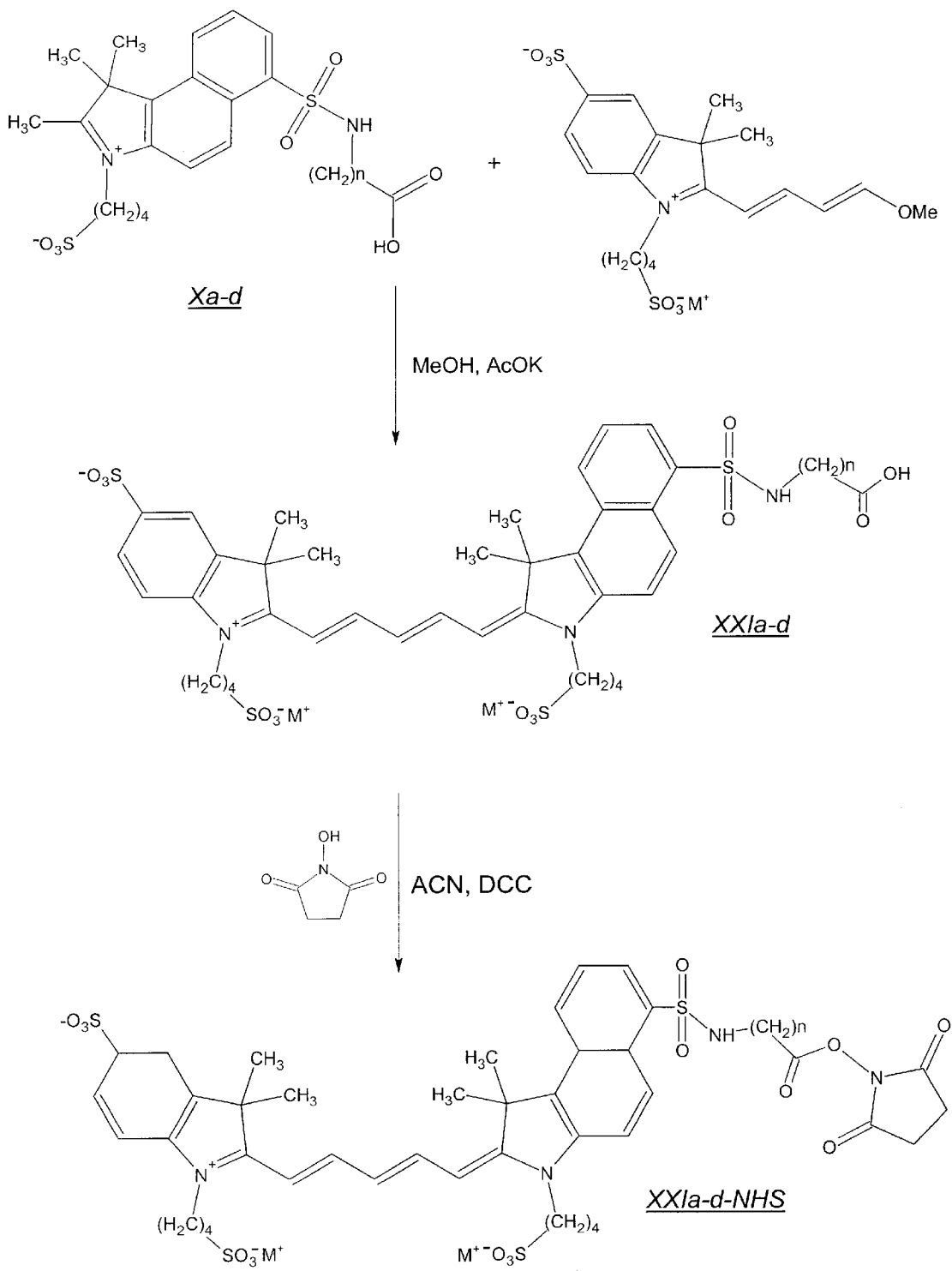
FIG. 39 outlines the preparation of XXIa–d and XXIa–d-NHS.
Figure 40:
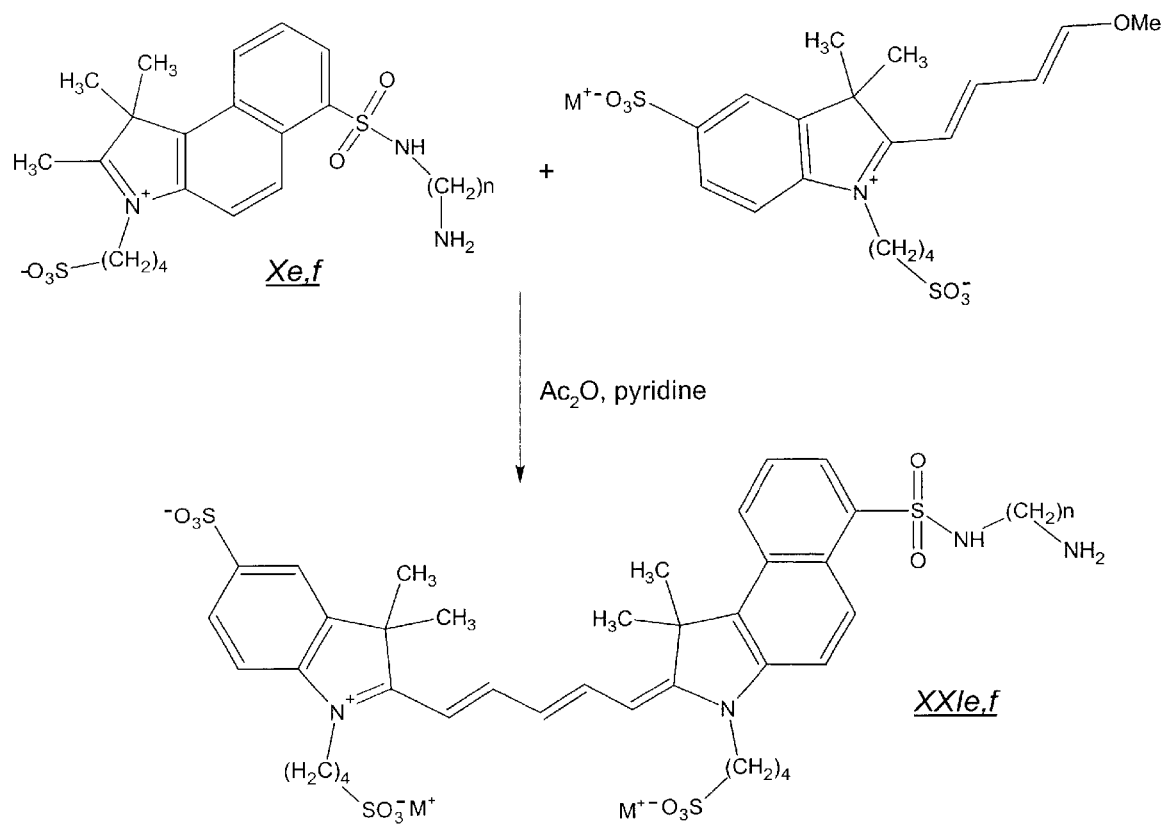
FIG. 40 outlines the preparation of XXIe and XXIf.
Figure 41:
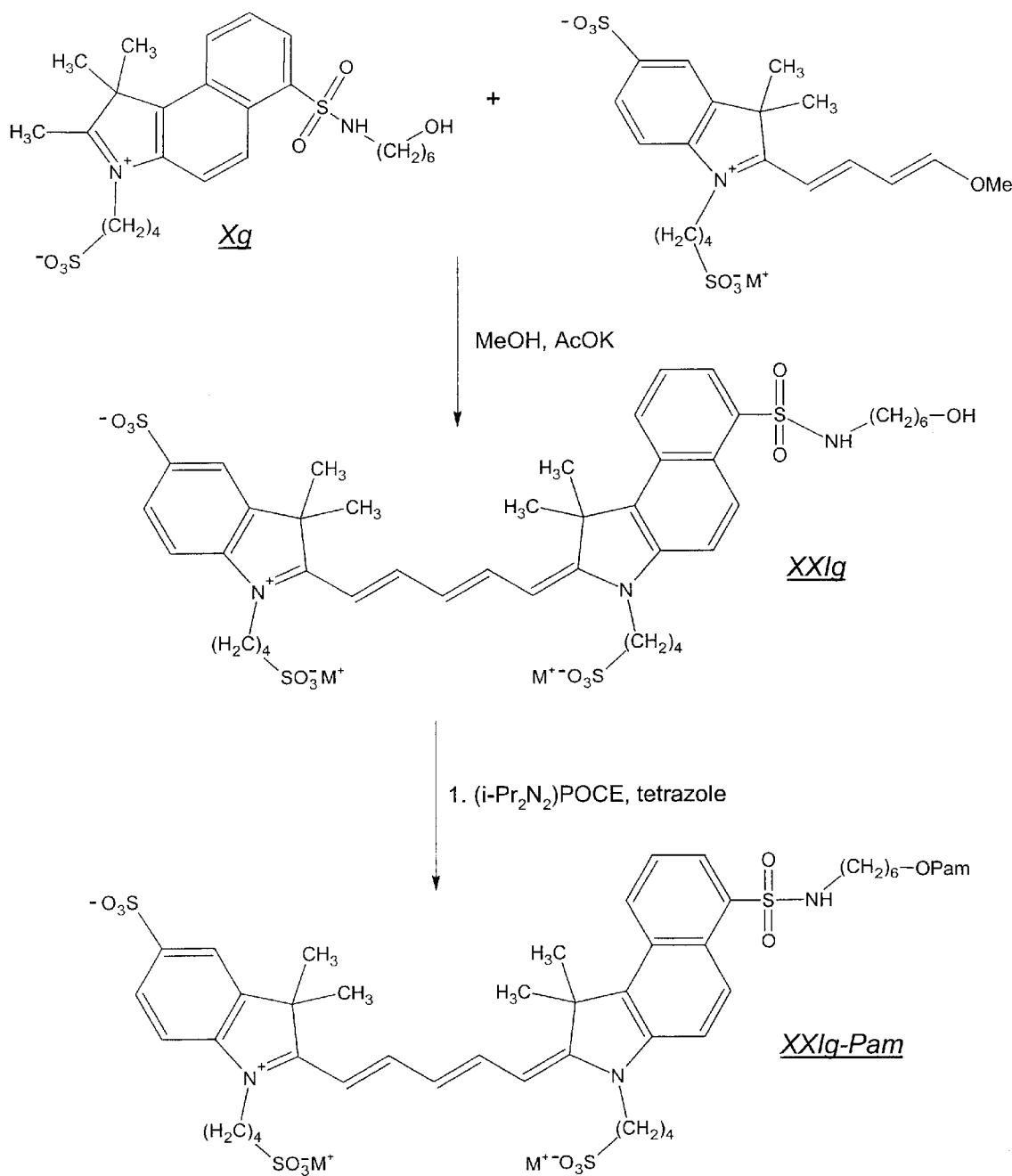
FIG. 41 outlines the preparation of XXIg and XXIg-Pam.
Figure 42:
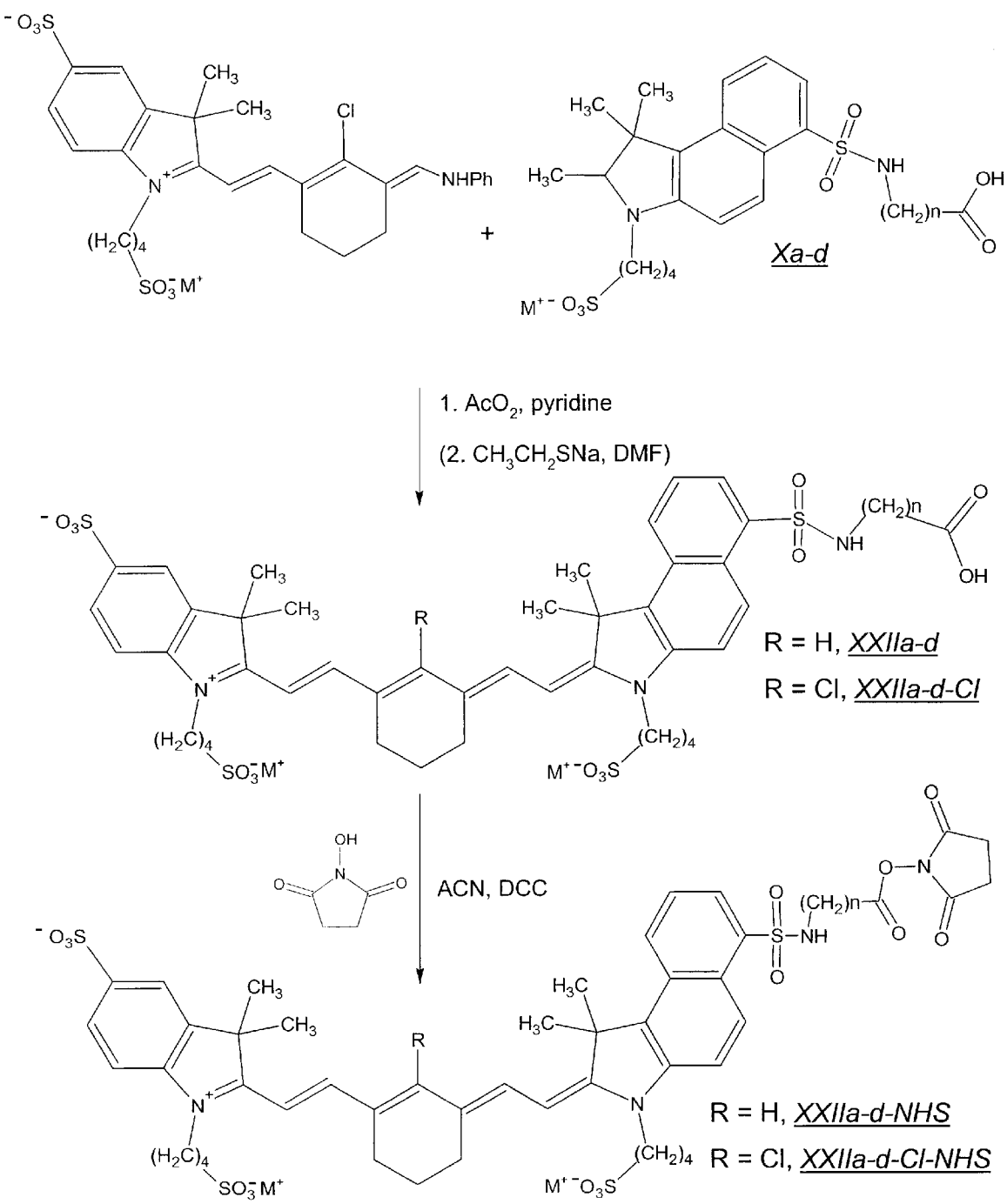
FIG. 42 outlines the preparation of XXIIa–d, XXIIa–d-Cl, XXIIa–d-NHS, and XXIIa–d-Cl-NHS.
Figure 43:
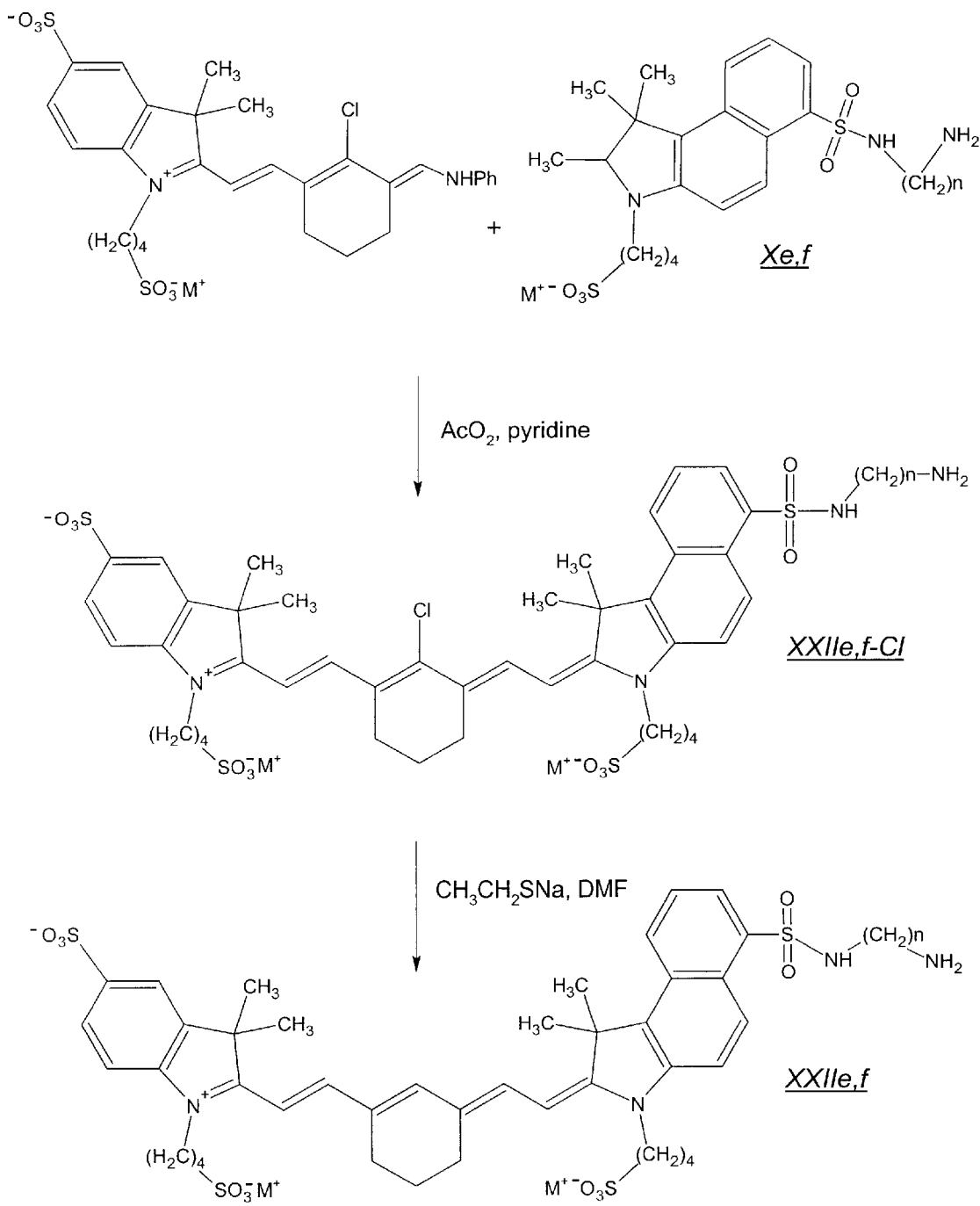
FIG. 43 outlines the preparation of XXIIe, XXIIf, XXIIe-Cl, and XXIIf-Cl.
Figure 44:
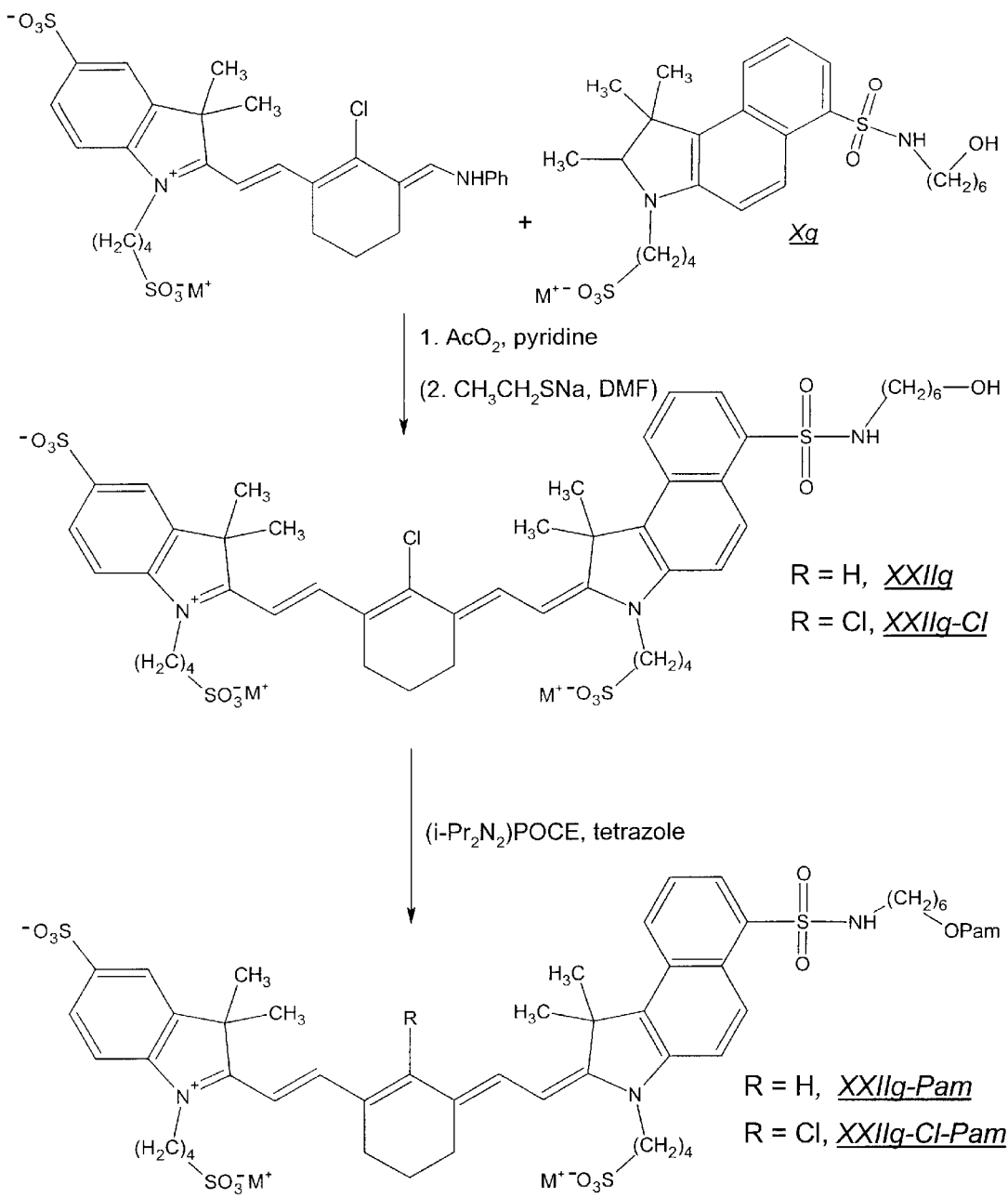
FIG. 44 outlines the preparation of XXIIg, XXIIg-Cl, XXIIg-Pam, and XXIIg-Cl-Pam.
Figure 45:
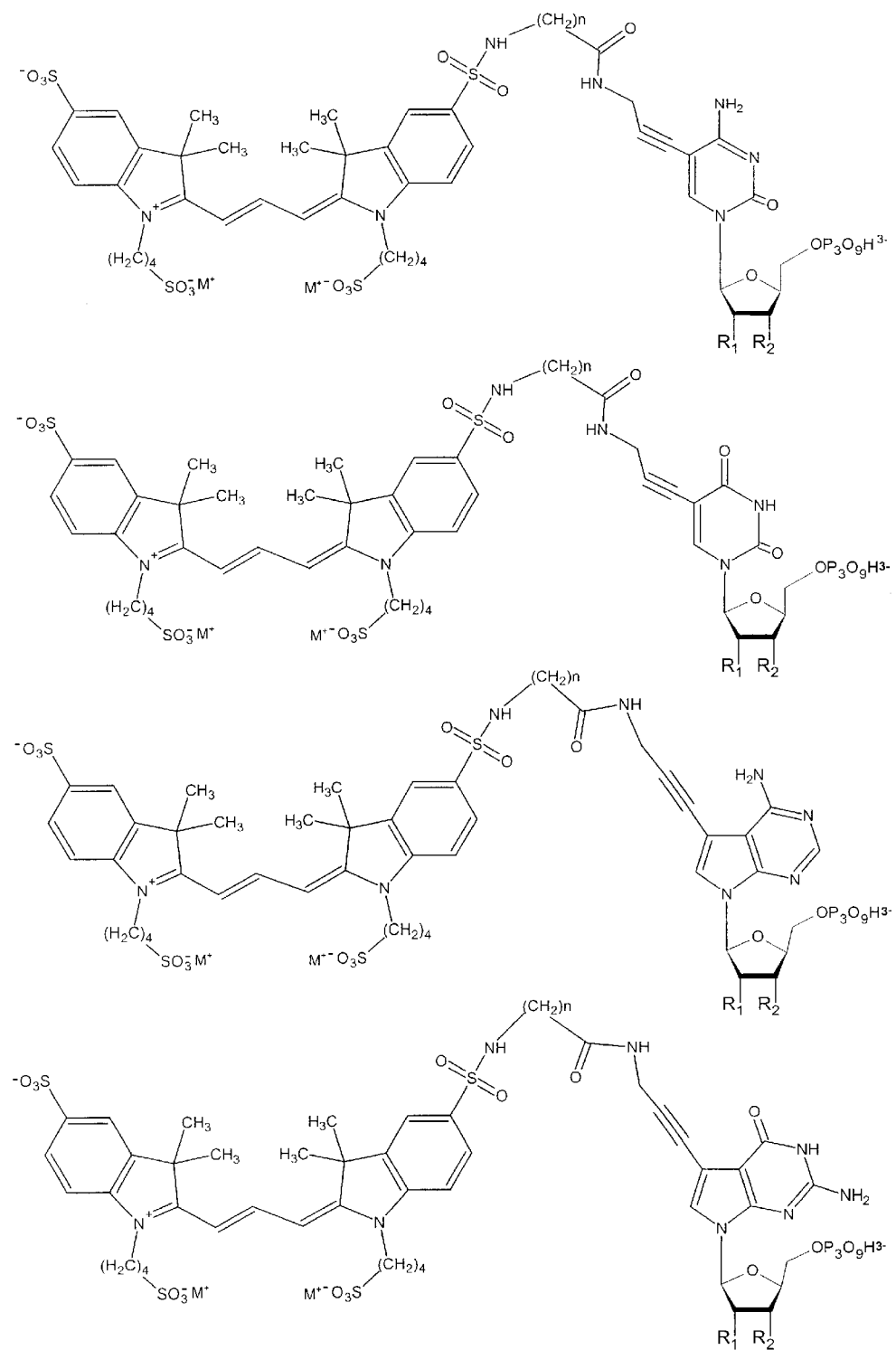
FIG. 45 depicts labeled ribonucleotides, deoxyribonucleotides, and dideoxyribonucleotides prepared with XIa–d-NHS (FIG. 9).
Figure 46:
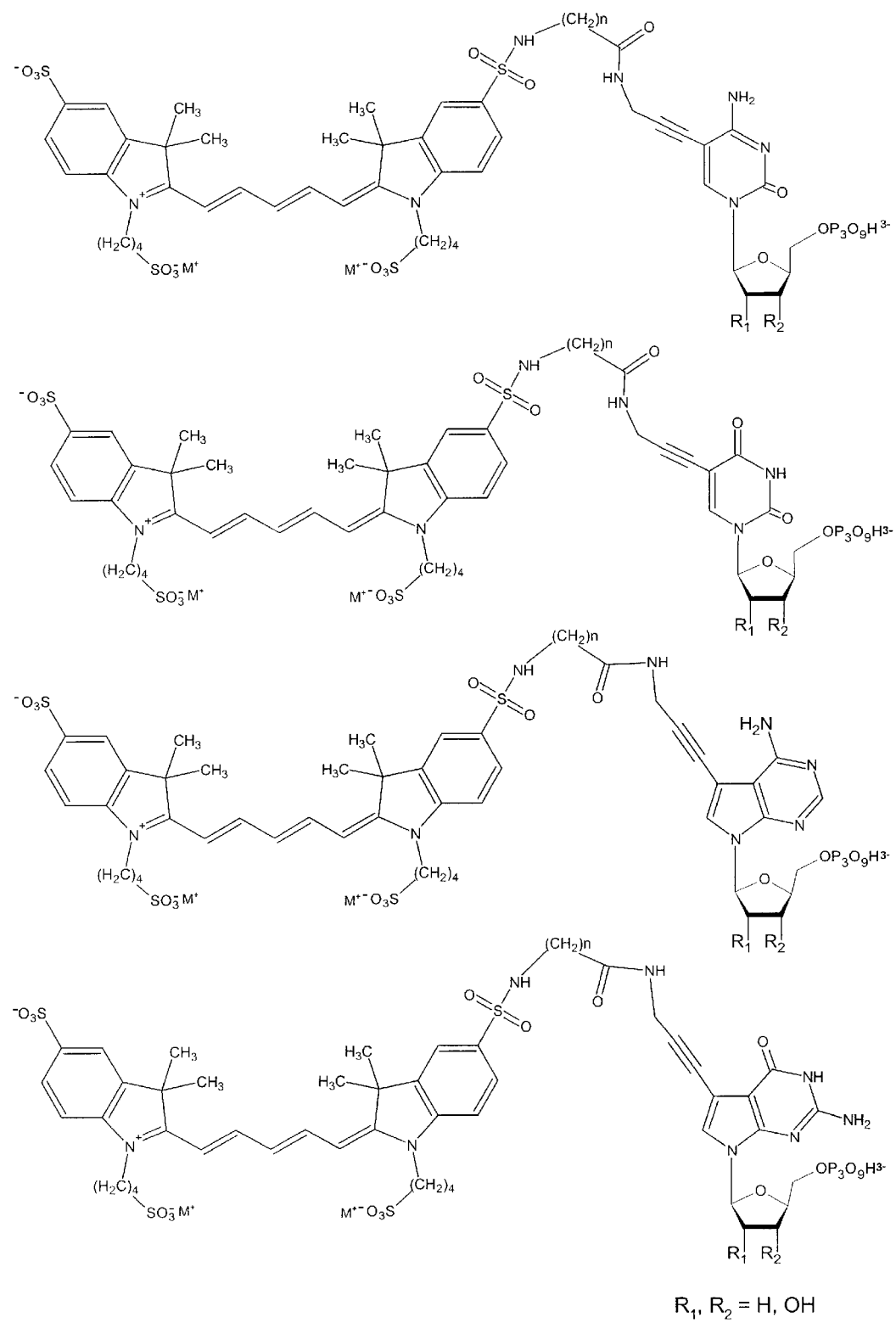
FIG. 46 depicts labeled ribonucleotides, deoxyribonucleotides, and dideoxyribonucleotides prepared with XIIa–d-NHS (FIG. 12).
Figure 47:
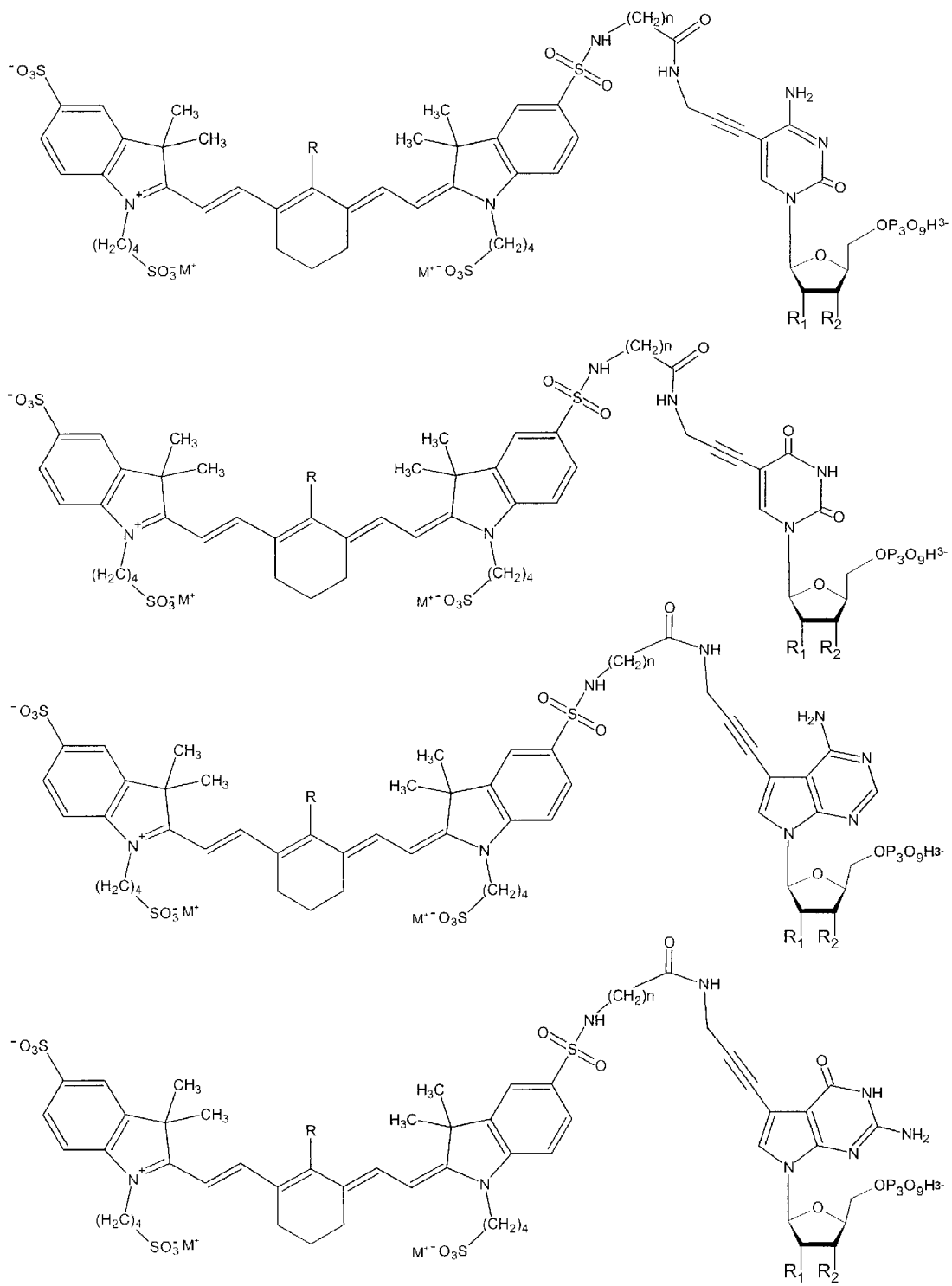
FIG. 47 depicts labeled ribonucleotides, deoxyribonucleotides, and dideoxyribonucleotides prepared with XIIIa–d-NHS and XIIIa–d-Cl-NHS (FIG. 15).
Figure 48:
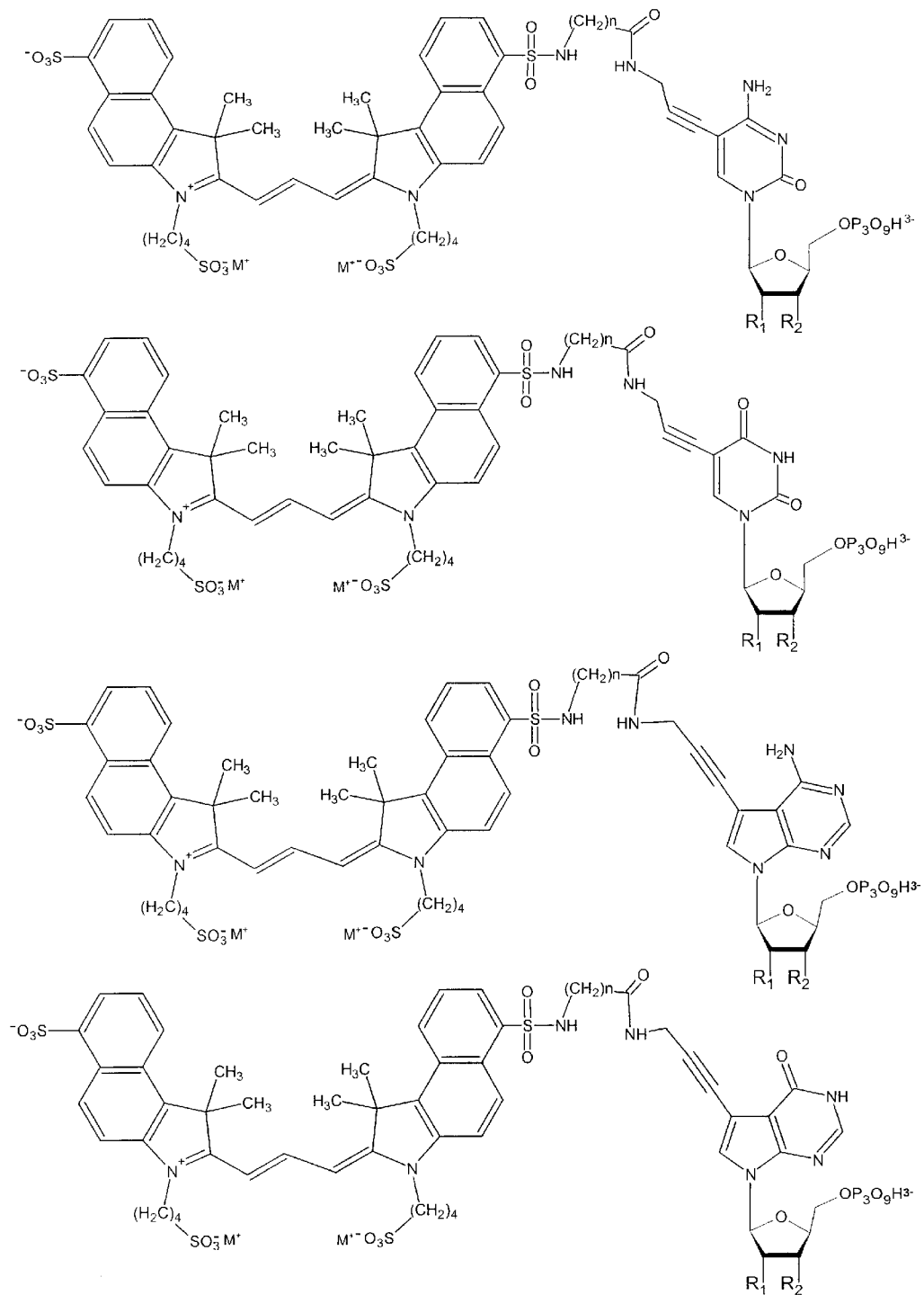
FIG. 48 depicts labeled ribonucleotides, deoxyribonucleotides, and dideoxyribonucleotides prepared with XIVa–d-NHS (FIG. 18).
Figure 49:
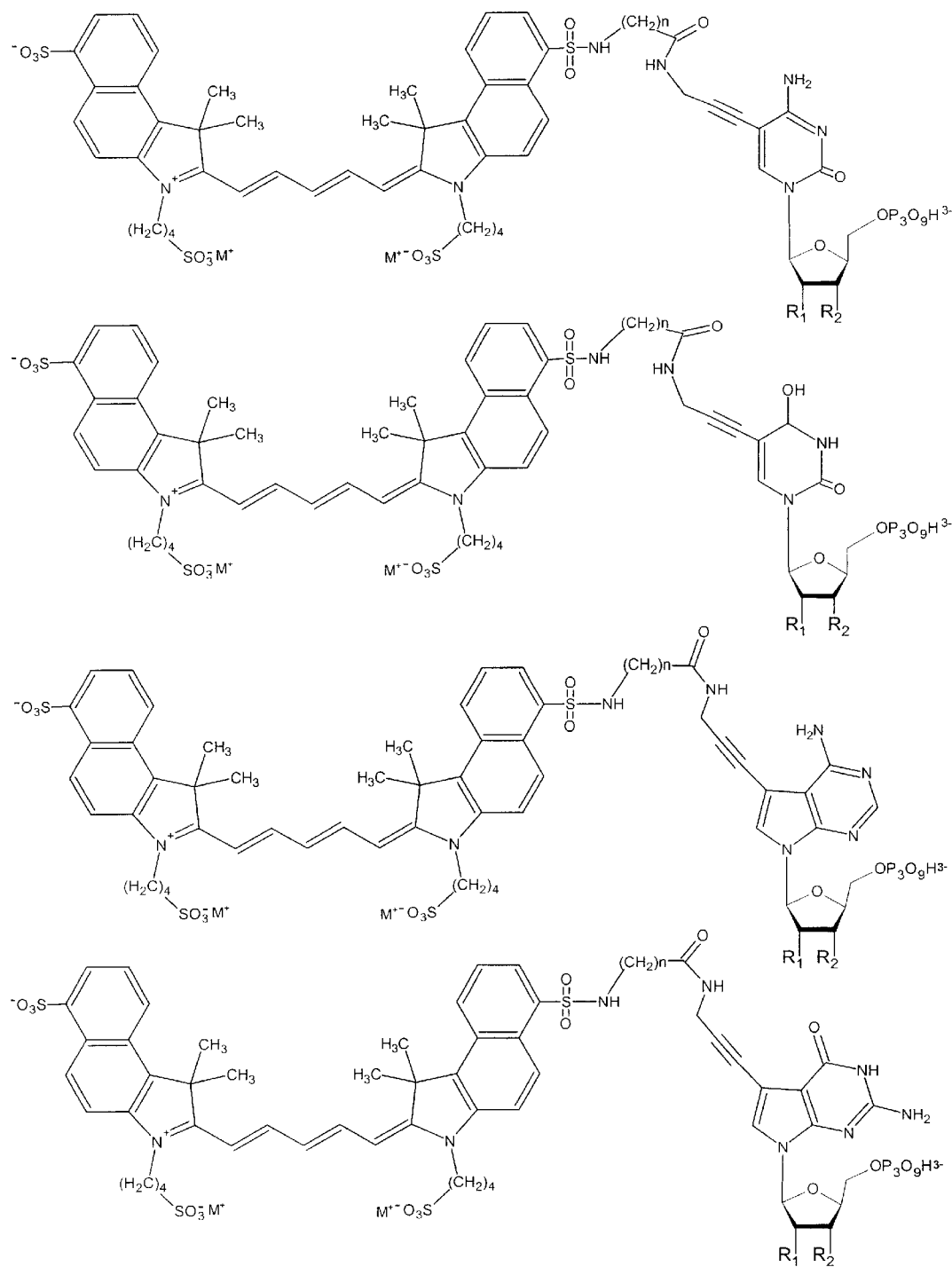
FIG. 49 depicts labeled ribonucleotides, deoxyribonucleotides, and dideoxyribonucleotides prepared with XVa–d-NHS (FIG. 21).
Figure 50:
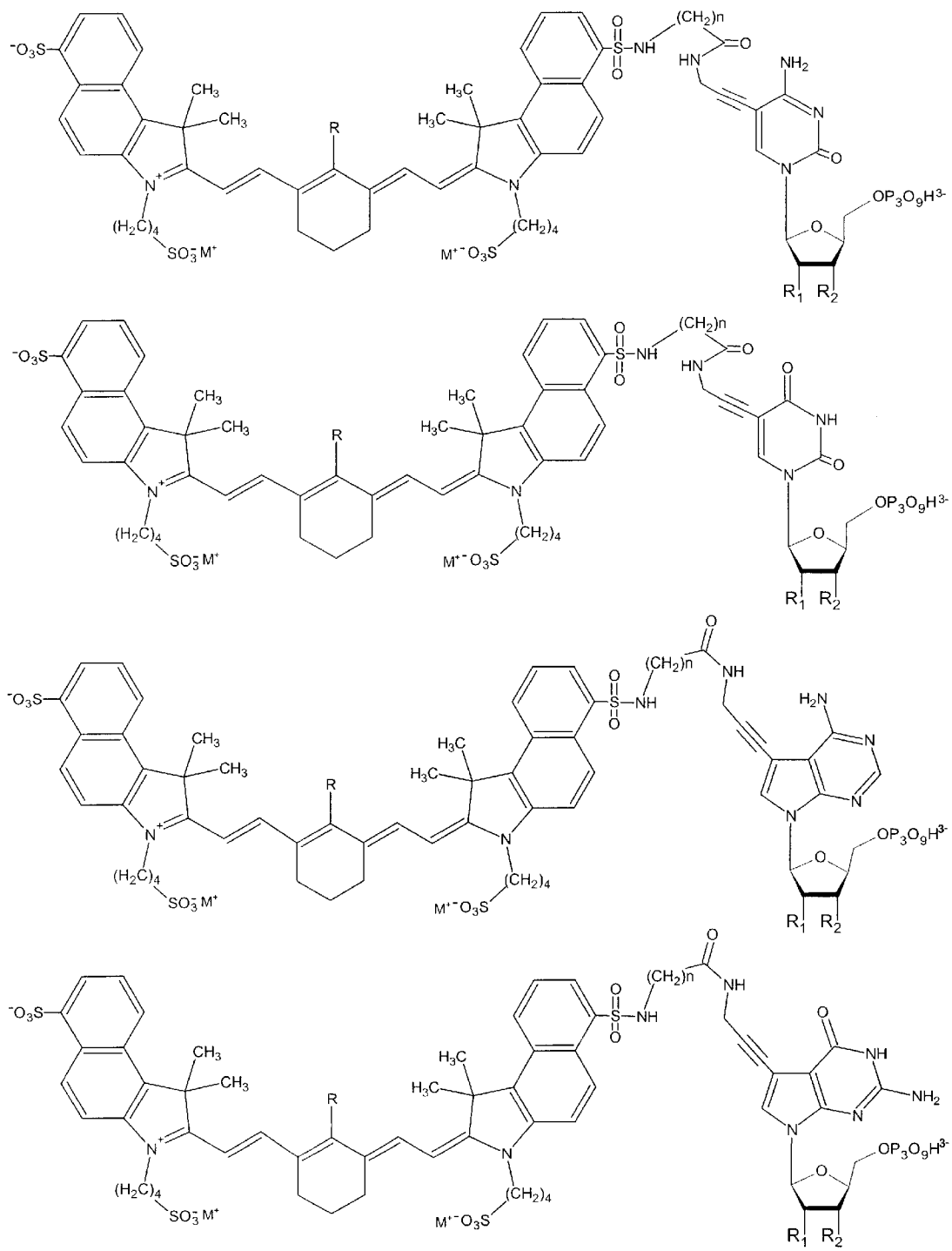
FIG. 50 depicts labeled ribonucleotides, deoxyribonucleotides, and dideoxyribonucleotides prepared with XVIa–d-NHS and XVIa–d-Cl-NHS (FIG. 24).
Figure 51:
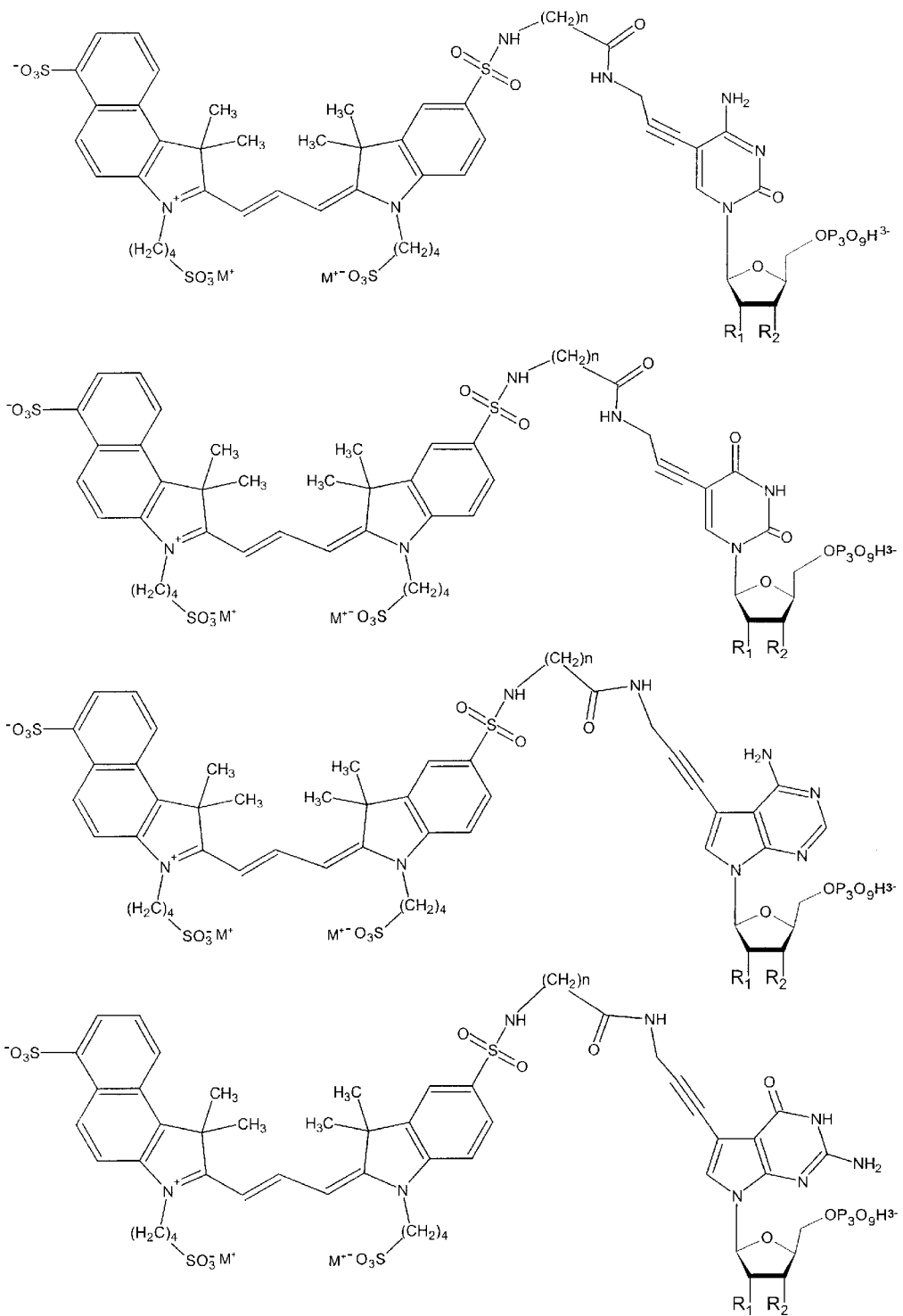
FIG. 51 depicts labeled ribonucleotides, deoxyribonucleotides, and dideoxyribonucleotides prepared with XVIIa–d-NHS (FIG. 27).
Figure 52:
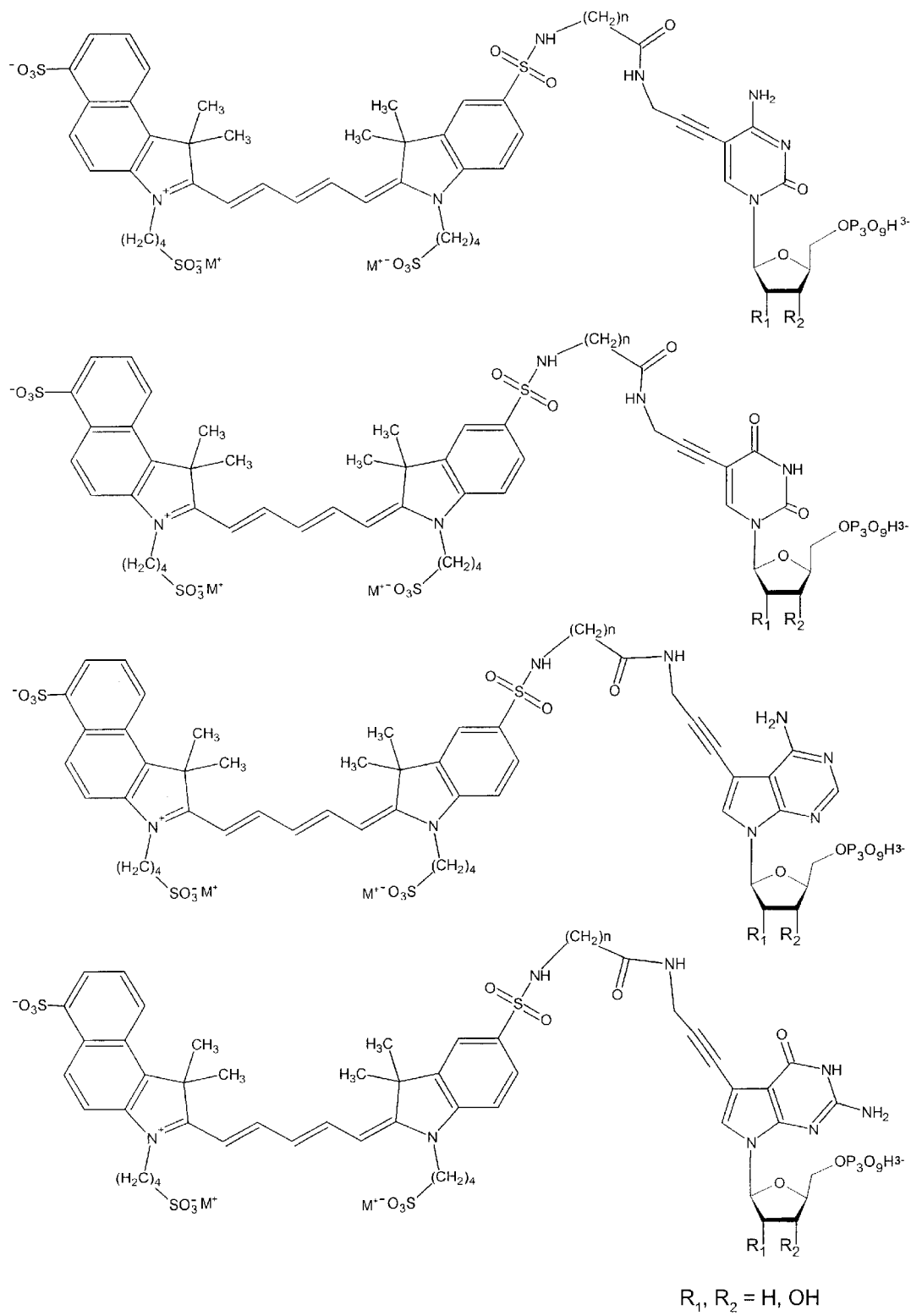
FIG. 52 depicts labeled ribonucleotides, deoxyribonucleotides, and dideoxyribonucleotides prepared with XVIIIa–d-NHS (FIG. 30).
Figure 53:
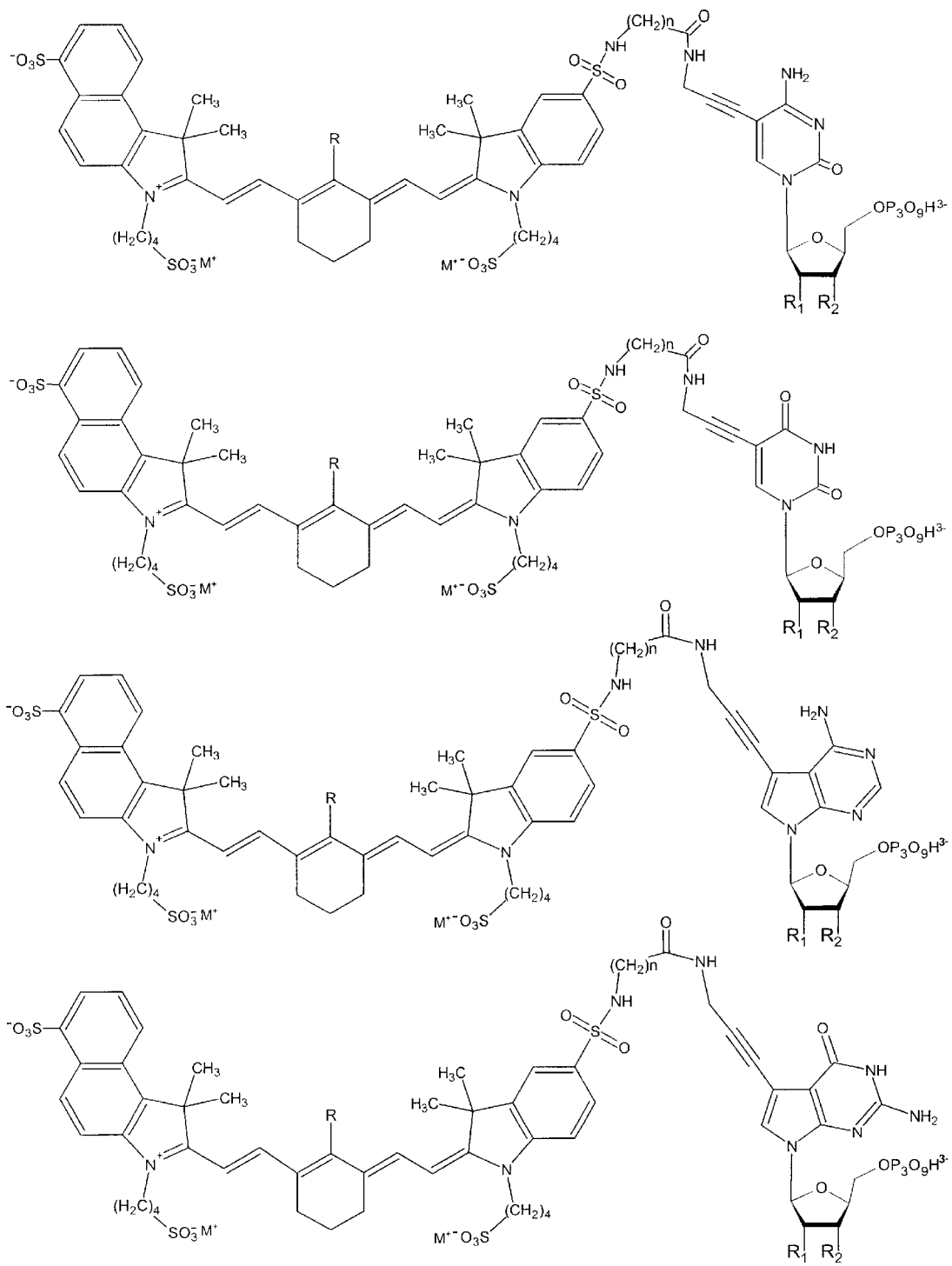
FIG. 53 depicts labeled ribonucleotides, deoxyribonucleotides, and dideoxyribonucleotides prepared with XIXa–d-NHS and XIXa–d-Cl-NHS (FIG. 33).
Figure 54:
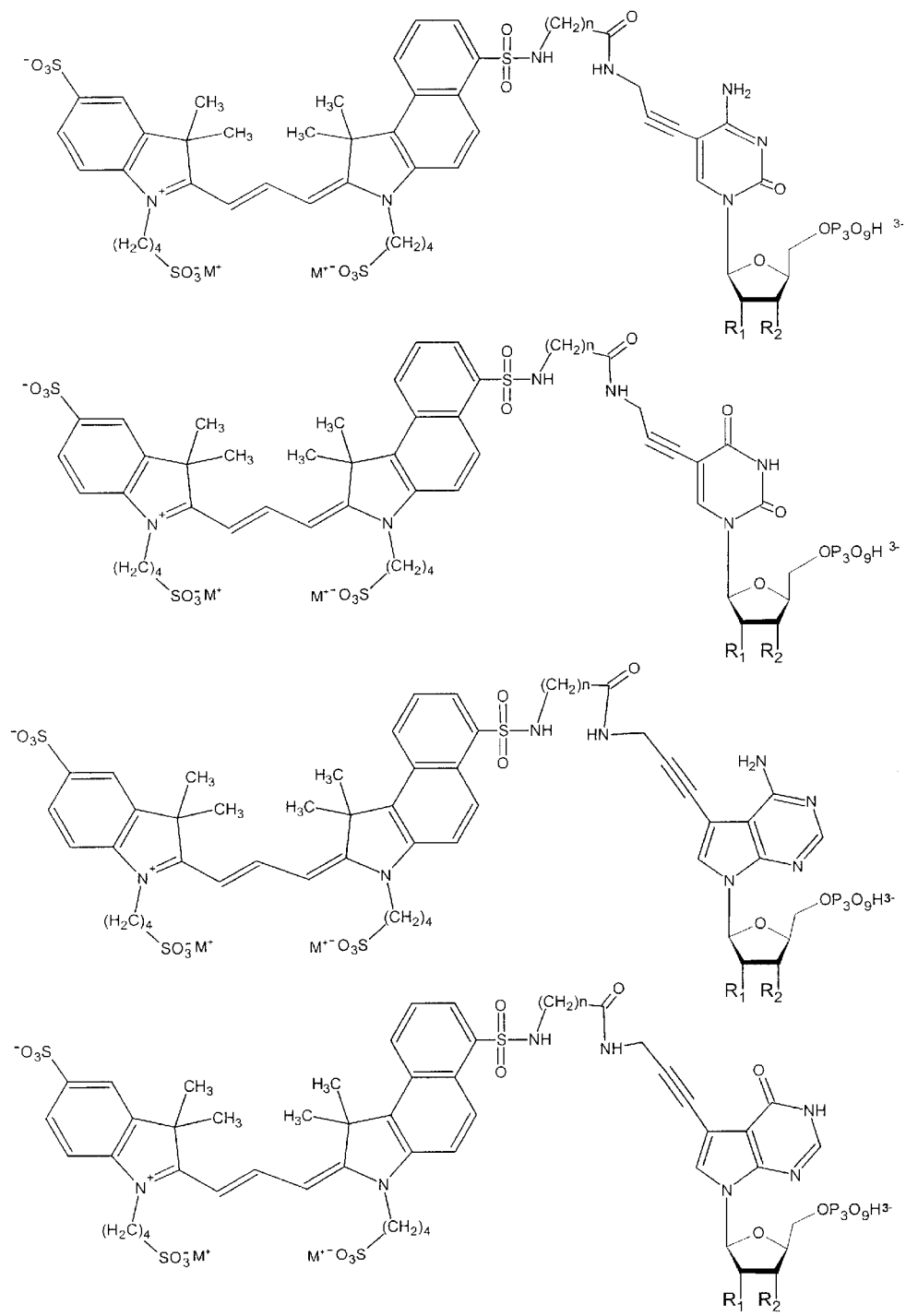
FIG. 54 depicts labeled ribonucleotides, deoxyribonucleotides, and dideoxyribonucleotides prepared with XXa–d-NHS (FIG. 36).
Figure 55:
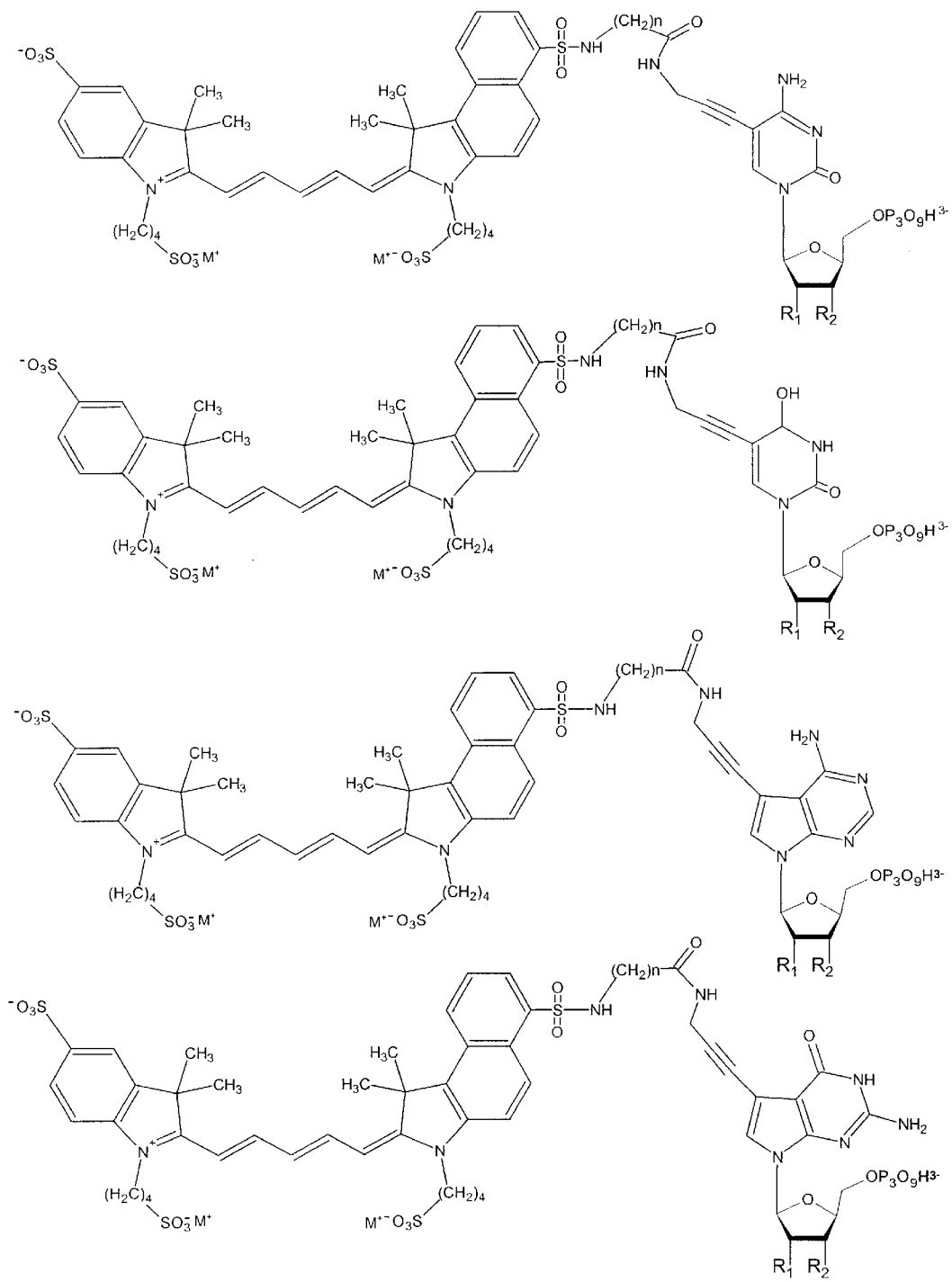
FIG. 55 depicts labeled ribonucleotides, deoxyribonucleotides, and dideoxyribonucleotides prepared with XXIa–d-NHS (FIG. 39).
Figure 56:
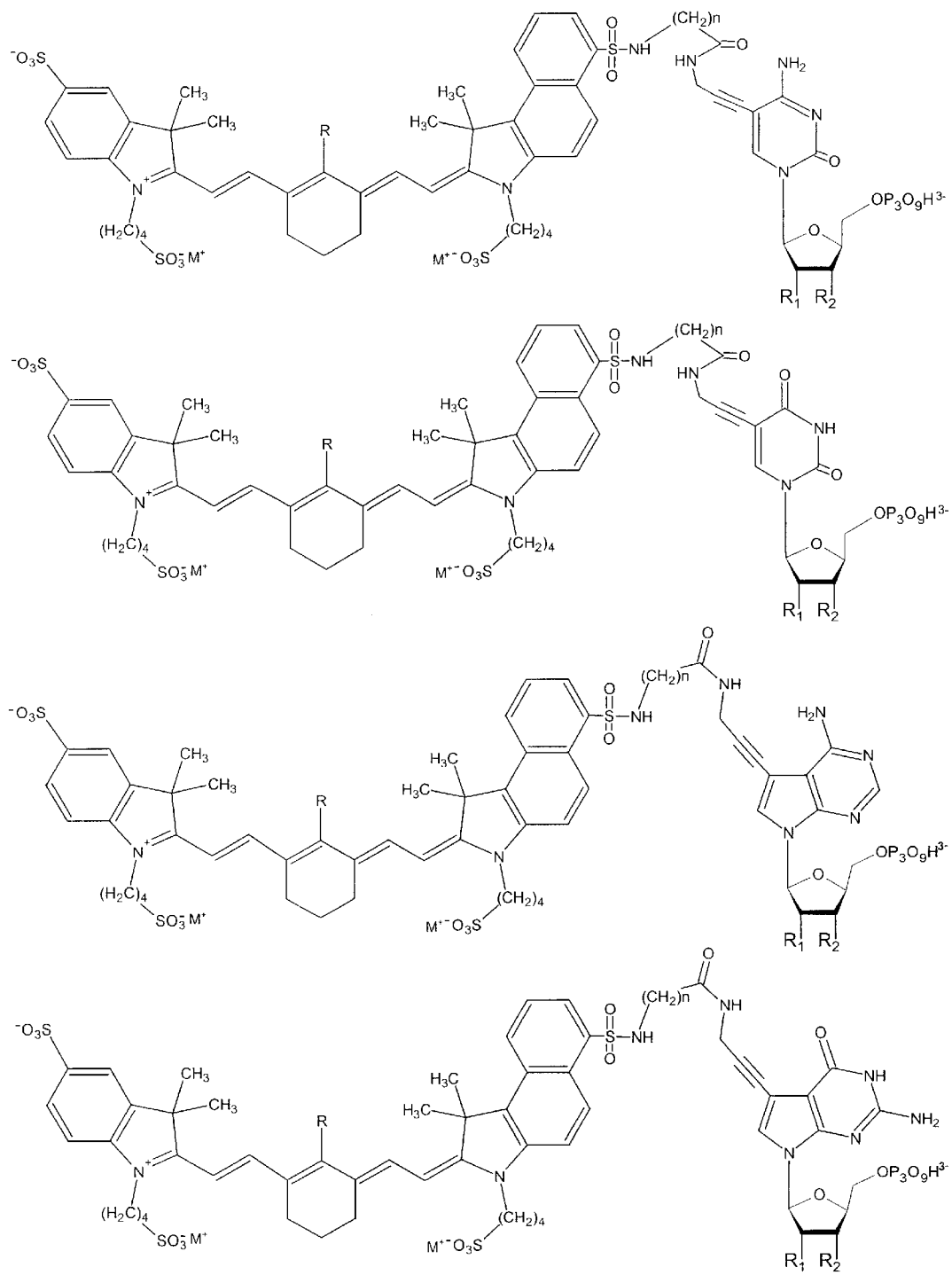
FIG. 56 depicts labeled ribonucleotides, deoxyribonucleotides, and dideoxyribonucleotides prepared with XXIIa–d-NHS and XXIIa–d-Cl-NHS (FIG. 42).
Figure 57:
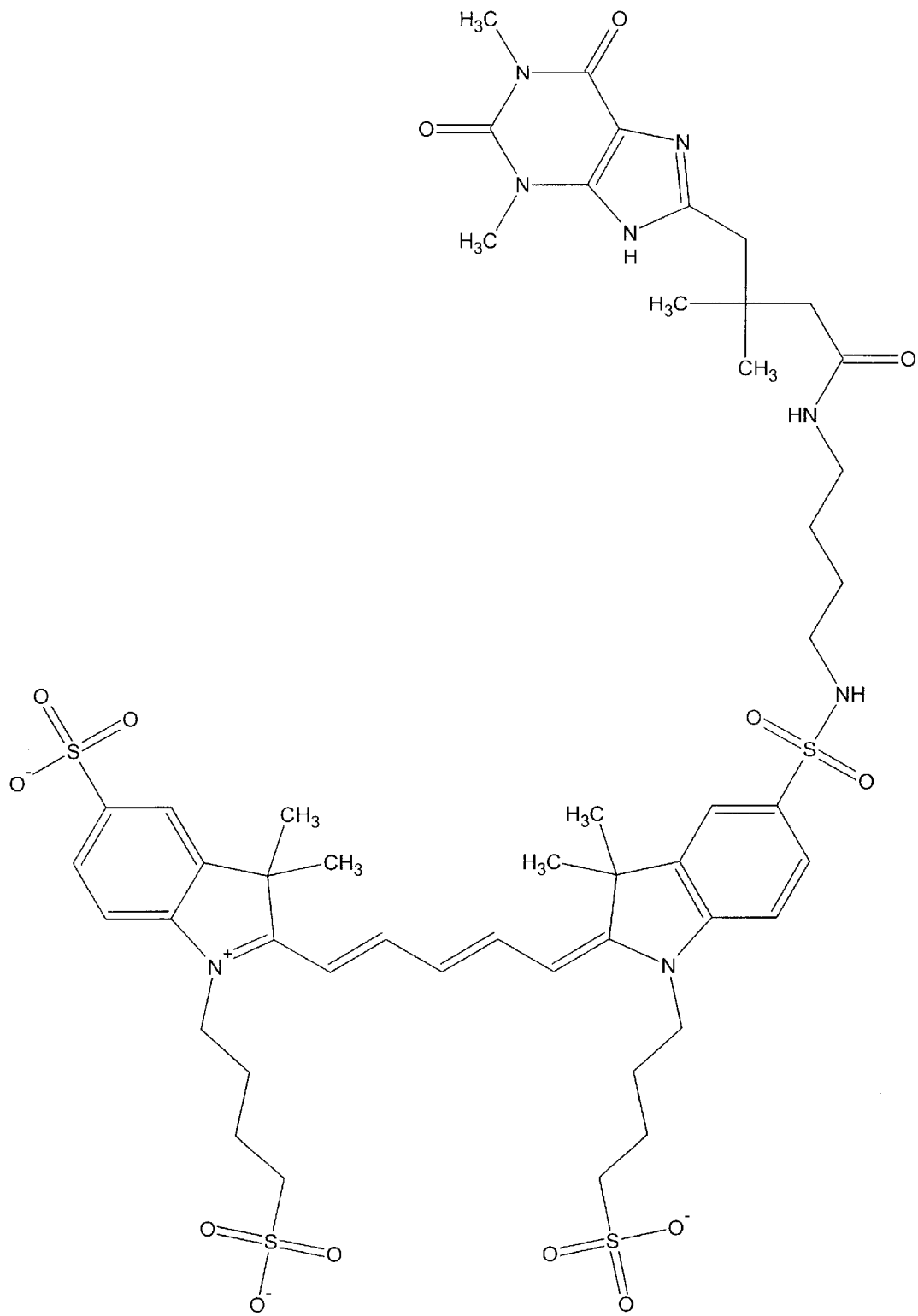
FIG. 57 depicts a theophylline-cyanine conjugate.

More specifically, the fluorescent labelling dyes of the present invention can be represented by the general formulae of FIGS. 2 and 3 wherein $X_1$ and $X_2$ are as above defined and preferably —C(CH$_3$)$_2$. Two general methods for the preparation of 2,3,3-trimethyl-(3H)-indoles with sulfamidoallkyl linker arms, are shown in FIG. 4. These compounds are key intermediates in the syntheses of the cyanine dyes. Similar schemes can be followed for the syntheses of 1,1,2-(1H)-benz[e]indoles with sulfamidoallkylene linker arms. According to the scheme shown in FIG. 4a, the synthesis starts with cheap, easily available 4-acetamidobenzene sulfonyl chloride (a starting material in the synthesis of sulfa drugs). This compound reacts with a wide variety of aminoalkylene compounds H$_2$N(CH$_2$)$_n$Z. In many cases, it is necessary to protect the functionality Z during this step or in later steps. Protected functionalities are indicated as Z(prot). This can be accomplished using standard protecting groups. For example, carboxyl groups can be protected as t-butyl esters, alcohol groups as tetrahydropyranyl (THP) acetals and amines as trifluoroacetamides, or, more conveniently, a large excess of diaminoalkanes can be used: the distal amino group can then be protected as a trifluoroacetamide. In the next step of FIG. 4a, the acetamido protecting group is removed by base hydrolysis. Under these conditions the previously formed sulfamido bonds are stable. The resulting primary aromatic amino groups are reduced to hydrazines by the action of SnCl$_2$ in concentrated hydrochloric acid. In the final step, a Fischer indole synthesis is performed by condensing the hydrazino derivatives with 3,3-dimethyl-2-butanone.

According to the alternative scheme (FIG. 4b), the Fischer indole synthesis takes place in the first step., that is, 4-hydrazinobenzenesulfonic acid is condensed with 3,3-dimethyl-2-butanone. The product, 2,3,3-trimethyl-(3H)-indole-4-sulfonic acid potassium salt, is converted to 2,3,3-trimethyl-(3H)-indole-4-sulfochloride sulfonyl chloride by heating it with phosphorus pentachloride. As in the previous method, the sulfochloride is then reacted with a wide variety of aminoalkyl compounds H$_2$N(CH$_2$)$_n$Z(prot). The protective groups can be removed most conveniently after the N-alkylation of the indolenine.

More specifically, compounds fall within the domain of the present invention are synthesized as shown in FIGS. 5–44.

Similar schemes can be followed for the synthesis of oxa- and thiacyanines with sulfamidoalkyl linker arms. In particular, 2-methylbenzoxazoles, 2-methylnaphtoxazoles, 2-methylbenzothiazoles and 2-methylnaphtothiazoles with the appropriate substituents in the benzo or naptho ring (sulfonic or sulfamidoalkylen groups) are used in place of the corresponding 2,3,3-trimethyl-(3H)-indoles 1,1,2-(1H)-benz[e]indoles. Asymmetric dyes (oxa-indocyanines, thia-indocyanines, oxa-thiacyanines) can also be made by appropriately choosing the corresponding heterocycles.

The optical properties of some dyes series in phosphate-buffered saline solution are summarized in the following Table:

| DYE | Absorption (λ max) | Emission (λ max) |
|---|---|---|
| 2,3,3-indole series: | | |
| trimethine | 550 | 565 |
| pentamethine | 650 | 668 |
| heptamethine-H-cyclohexene | 747 | 776 |
| heptamethine-Cl-cyclohexene | 776 | 803 |
| 1,2,2-benz[e]-indole series | | |
| trimethine | 580 | 600 |
| pentamethine | 670 | 695 |
| heptamethine-H-cyclohexene | 780 | 807 |
| heptamethine-Cl-cyclohexene | 810 | 843 |
| Mixed indole/benz[e]indole series | | |
| trimethine | 565 | 580 |
| pentamethine | 660 | 675 |
| heptamethine-H-cyclohexene | 766 | 778 |
| heptamethine-Cl-cyclohexene | 790 | 822 |

Immunoassays can be developed that rely on fluorescence measurements in the quantitation step. These measurements include fluorescence intensity, lifetime fluorescence or anisotropy (fluorescence polarization). To this end, the fluorescent compound of the invention is conjugated to an immunologically binding reagent, such as a monoclonal or polyclonal antibody or an antigen.

The conjugation of cyanine dyes with a sulfamidoalkylene spacer arm to anti-β-HCG and anti-α-fetoprotein antibodies is described in Example 26 and 28. Standard separation assays employing the cyanine conjugates and fluorescence intensity measurement of the captured fluorescent label are described in Examples 25 and 27, respectively.

The dyes of the present invention also have utility in any current application for detection of nucleic acids that requires a sensitive detection reagent. The nucleic acid in the sample may be either RNA or DNA, or a mixture thereof. When the nucleic acid is DNA, the DNA may be optionally be single-, double-, triple- or quadruple-stranded DNA. The nucleic acid may be either natural (biological in origin) or synthetic (prepared artificially) and can be present in the sample as nucleic acid fragments, oligonucleotides, or nucleic acid polymers. The presence of the nucleic acid in the sample may be due to a successful or unsuccessful experimental methodology, undesirable contamination, or a disease state.

The fluorescent dyes of the present invention can also be used for DNA sequencing methods. Typically, a fluorophore-labelled probe specific to the sequence is hybridised with the target DNA and the sequence ladders are identified by laser induced fluorescence or other appropriate means for detecting fluorescence labelled DNA.

Example 29 describes a method for the labelling of ribonucleotides, deoxyribonucleotides and dideoxyribonucleotides with the dyes of the invention. The structures of the compounds obtained by this method are shown in FIGS. 45–56.

One particularly useful form of fluorescence assay is the utilisation of fluorescence polarisation. Fluorescence polarisation occurs when a fluorescent molecule is excited with polarised light which results in he emitted light from the fluorescence molecule also to be polarised. A quantitative determination of the polarisation of the excited molecule can be obtained by measuring the relative intensity of the emitted light parallel and perpendicular to the plane of polarisation of the excitation light. This type of assay has the advantage of being homogeneous, that is it does not require any separation steps. Example 30 describes the preparation of a theophylline-(sulfamidoalkylamino)cyanine conjugate.

EXAMPLE 1

Preparation of 2,3,3-Trimethyl-(3H)-indole-4-sulfochloride (I)

5 g of dry 2,3,3-trimethyl-(3H)-indole 5-sulfonic acid potassium salt (18 mmol), prepared as described in Mank et al., Anal. Chem. 1995, 67, p. 1744, were mixed with 7.5 g of $PCl_5$ (36 mmol) and 2 ml of $POCl_3$ (22 mmol) in a 500 ml round bottom flask. The flask, fitted with a reflux condenser was heated under argon for 2 hours at 110° C. in an oil bath. Unreacted phosphorus chlorides were removed under vacuum at 110° C. using a membrane pump operating at 7 mm Hg. The cooled mixture was triturated with two 150 mL portions of dry hexane in order to remove impurities. The hexane extracts were discarded and the crude sulfochloride is dried at 110° C. in vacuo (yield: 90%).

EXAMPLE 2a

Preparation of the Sulfonamide Derivative of 2,3,3-Trimethyl-(3H)-indole With the t-Butyl Ester of Glycine, 5-($SO_2$—NH—$CH_2$—COO-t-Butyl)-2,3,3-trimethyl-(3H)-indole (IIa)

5.15 g of glycine t-butyl ester dibenzenesulfimide salt (12 mmol) and 8 mL of pyridine are dissolved in 100 mL of chloroform. To this solution are added under stirring 2 g of crude 2,3,3-trimethyl-(3H)-indole-4-sulfochloride (7.8 mmol) from Example 1. After stirring at room temperature overnight, the solvent and the pyridine are evaporated in vacuo. The residue is treated three times with 100 mL of chloroform which is then again removed in vacuo. The crude sulphonamide is then dissolved in chloroform and precipitated by dropwise addition to 1 L of diethyl ether. (Yield: 70%).

EXAMPLE 2b

Preparation of the Sulfonamide Derivative of 2,3,3-Trimethyl-(3H)-indole With the t-Butyl Ester of β-alanine, 5-($SO_2$NH—$CH_2$—$CH_2$—COO-t-Butyl)-2,3,3-trimethyl-(3H)-indole (IIb)

The sulfonamide was prepared according to the procedure of Example 2a from 2.18 g of β-alanine t-butyl ester hydrochloride (12 mmol), 8 mL of pyridine and 2 g of 2,3,3-trimethyl-(3H)-indole-4-sulfochloride (7.8 mmol) from Example 1. (Yield: 67%).

EXAMPLE 2c

Preparation of the Sulfonamide Derivative of 2,3,3-Trimethyl-(3H)-indole With the t-Butyl Ester of γ-aminobutyric, 5-($SO_2$NH—$CH_2$—$CH_2$—$CH_2$—$CH_2$—COO-t-Butyl)-2,3,3-trimethyl-(3H)-indole (IIc)

The sulfonamide was prepared according to the procedure of Example 2a from 2.35 g γ-aminobutyric t-butyl ester hydrochloride (12 mmol), 8 mL of pyridine and 2 g of 2,3,3-trimethyl-(3H)-indole 4-sulfochloride (7.8 mmol) from Example 1. (Yield: 90%).

EXAMPLE 2d

Preparation of the Sulfonamide Derivative of 2,3,3-Trimethyl-(3H)-indole With the t-Butyl Ester of ε-aminocaproic Acid, 5-($SO_2$NH—$CH_2$—$CH_2$—$CH_2$—$CH_2$—$CH_2$—COO-t-Butyl)-2,3,3-trimethyl-(3H)-indole (IId)

The sulfonamide was prepared according to the procedure of Example 2 from 2.68 g of ε-aminocaproic acid t-butyl ester hydrochloride (12 mmol), 8 mL of pyridine and 2 g of 2,3,3-trimethyl-(3H)-indole-4-sulfochloride (7.8 mmol) from Example 1. (Yield: 80%).

EXAMPLE 2e

Preparation of the Sulfonamide Derivative of 2,3,3-Trimethyl-(3H)-indole With 1,4-diaminobutane, 5-($SO_2$NH—$CH_2$—$CH_2$—$CH_2$—$CH_2$—$NH_2$)-2,3,3-trimethyl-(3H)-indole (IIe)

The sulfonamide was prepared according to the procedure of Example 2a from 8 mL of 1,4-diaminobutane (80 mmol), 8 mL of pyridine and 2 g of 2,3,3-trimethyl-(3H)-indole-4-sulfochloride (7.8 mmol) from Example 1. (Yield: 75%).

EXAMPLE 2f

Preparation of the Sulfonamide Derivative of 2,3,3-Trimethyl-(3H)-indole With 1,6-diaminohexane, 5-($SO_2$NH—$CH_2$—$CH_2$—$CH_2$—$CH_2$—$CH_2$—$CH_2$—$NH_2$)-2,3,3-trimethyl-(3H)-indole (IIf)

The sulfonamide was prepared according to the procedure of Example 2a from 10 g of 1,4-diaminohexane (86 mmol), 8 mL of pyridine and 2 g of 2,3,3-trimethyl-(3H)-indole-4-sulfochloride (7.8 mmol) from Example 1. (Yield. 80%).

EXAMPLE 2g

Preparation of the Sulfonamide Derivative of 2,3,3-Trimethyl-(3H)-indole with 6-amino-1-hexanol, 5-($SO_2NH$—$CH_2$—$CH_2$—$CH_2$—$CH_2$—$CH_2$—$CH_2$—OH)-2,3,3-trimethyl-(3H)-indole (IIg)

The sulfonamide was prepared according to the procedure of Example 2a from 1.4 g of 6-amino-1-hexanol (12 mmol), 8 mL of pyridine and 2 g of 2,3,3-trimethyl-(3H)-indole-4-sulfochloride (7.8 mmol) from Example 1. (Yield: 78%).

EXAMPLE 3a

Preparation of 5-($SO_2NH$—$CH_2$—$CH_2$—$CH_2$—$CH_2$—$NHCOCF_3$)-2,3,3-Trimethyl-(3H)-indole (IIIa)

1.8 g of the sulfonamide prepared according to the procedure of Example 2d was treated with trifluoroacetic anhydride at room temperature. (Yield: 96%).

EXAMPLE 3b

Preparation of 5-($SO_2NH$—$CH_2$—$CH_2$—$CH_2$—$CH_2$—$CH_2$—$CH_2$—$NHCOCF_3$)-2,3,3-Trimethyl-(3H)-indole (IIIb)

1.8 g of the sulfonamide prepared according to the procedure of Example 2e was treated with trifluoroacetic anhydride at room temperature. (Yield: 99%).

EXAMPLE 4

Preparation of 5-($SO_2NH$—$CH_2$—$CH_2$—$CH_2$—$CH_2$—$CH2$—$CH2$—OTHP)-2,3,3-Trimethyl-(3H)-indole (IVa)

1.8 g of the sulfonamide prepared according to the procedure of Example 2g was treated with an excess of 3,4-diidro-2H-pyrane at room temperature and a few drops of trifluoroacetic acid as catalyst. (Yield: 90%).

EXAMPLE 5

Preparation of 1,1,2-Trimethyl-(1H)-benz[e]indole-6-sulfochloride (V)

1,1,2-trimethyl-(1H)-benz[e]indole-6-sulfonic acid, prepared as described in WO 97/13810, was dissolved in methanol and stirred with a saturated potassium hydroxide in isopropanol. The potassium salt precipitated and was collected on a filter, washed with isopropanol and dried in vacuo. 6.0 g of the salt (18.3 mmol), were mixed with 7.5 g of $PCl_5$ (36 mmol) and 2 ml of $POCl_3$ (22 mmol) in a 500 ml round bottom flask. The flask, fitted with a reflux condenser was heated under argon for 2 hours at 110° C. in an oil bath. Unreacted phosphorus chlorides were removed under vacuum at 110° C. using a membrane pump operating at 7 mm Hg. The cooled mixture was triturated with two 150 mL portions of dry hexane in order to remove impurities. The hexane extracts were discarded and the crude sulfochloride is dried at 110° in vacuo (yield: 60%).

EXAMPLE 6a

Preparation of the Sulfonamide Derivative of 1,1,2-Trimethyl-(1H)-benz[e]indole With the t-Butyl Ester of Glycine, 6-($SO_2NH$—$CH_2$—COO-t-Butyl)-1,1,2-trimethyl-(1H)-benz[e]indole (VIa)

5.15 g of glycine t-butyl ester dibenzenesulfimide salt (12 mmol) and 8 mL of pyridine are dissolved in 100 mL of chloroform. To this solution are added under stirring 2.5 g of 1,1,2-trimethyl-(1H)-benz[e]indole-6-sulfochloride (7.6 mmol) from Example 5. After stirring at room temperature overnight, the solvent and the pyridine are evaporated in vacuo. The residue is treated three times with 100 mL of chloroform which is then again removed in vacuo. The crude sulphonamide is then dissolved in chloroform and precipitated by dropwise addition to 1 L of diethyl ether. (Yield: 90%).

EXAMPLE 6b

Preparation of the Sulfonamide Derivative of 1,1,2-Trimethyl-(1H)-benz[e]indole With the t-Butyl Ester of β-alanine, 6-($SO_2NH$—$CH_2$—$CH_2$—COO-t-Butyl)-1,1,2-trimethyl-(1H)-benz[e]indole (VIb)

The sulfonamide was prepared according to the procedure of Example 6a from 2.18 g of β-alanine t-butyl ester hydrochloride (12 mmol), 8 mL of pyridine and 2.5 g of 1,1,2-trimethyl-(1H)-benz[e]indole-6-sulfochloride (7.6 mmol) from Example 5 (Yield: 81%).

EXAMPLE 6c

Preparation of the Sulfonamide Derivative of 1,1,2-Trimethyl-(1H)-benz[e]indole With the t-Butyl Ester of γ-aminobutyric, 6-($SO_2NH$—$CH_2$—$CH_2$—$CH_2$—$CH_2$—COO-t-Butyl)-1,1,2-trimethyl-(1H)-benz[e]indole (VIc)

The sulfonamide was prepared according to the procedure of Example 6a from 2.35 g γ-aminobutyric t-butyl ester hydrochloride (12 mmol), 8 mL of pyridine and 2.5 g 1,1,2-trimethyl-(1H)-benz[e]indole-6-sulfochloride (7.6 mmol) from Example 5 (Yield: 80%).

EXAMPLE 6d

Preparation of the Sulfonamide Derivative of 21,1,2-Trimethyl-(1H)-benz[e]indole With the t-Butyl Ester of ε-aminocaproic Acid, 6-($SO_2NH$—$CH_2$—$CH_2$—$CH_2$—$CH_2$—$CH_2$—COO-t-Butyl)-1,1,2-trimethyl-(1H)-benz[e]indole (VId)

The sulfonamide was prepared according to the procedure of Example 6a from 2.68 g of ε-aminocaproic acid t-butyl ester hydrochloride (12 mmol), 8 mL of pyridine and 2.5 g of 1,1,2-trimethyl-(1H)-benz[e]indole-6-sulfochloride (7.6 mmol) from Example 5. (Yield: 89%).

EXAMPLE 6e

Preparation of the Sulfonamide Derivative of 1,1,2-Trimethyl-(1H)-benz[e]indole With 1,4-diaminobutane, 7-($SO_2NH$—$CH_2$—$CH_2$—$CH_2$—$CH_2$—$NH_2$)-1,1,2-trimethyl-(1H)-benz[e]indole (VIe)

The sulfonamide was prepared according to the procedure of Example 13 from 8 mL of 1,4-diaminobutane (80 mmol), 8 mL of pyridine and 2.5 g of 1,1,2-trimethyl-(1H)-benz[e]indole-7-sulfochloride (7.6 mmol) from Example 12. (Yield: 90%).

EXAMPLE 6f

Preparation of the Sulfonamide Derivative of 1,1,2-Trimethyl-(1H)-benz[e]indole With 1,6-diaminohexane, 6-($SO_2NH$—$CH_2$—$CH_2$—$CH_2$—$CH_2$—$CH_2$—$CH_2$—$NH_2$)-1,1,2-trimethyl-(1H)-benz[e]indole (VIf)

The sulfonamide was prepared according to the procedure of Example 13 from 10 g of 1,4-diaminohexane (86 mmol), 8 mL of pyridine and 2 g of 1,1,2-trimethyl-(1H)-benz[e] indole-7-sulfochloride (7.6 mmol) from Example 12. (Yield 90%).

EXAMPLE 6g

Preparation of the Sulfonamide Derivative of 1,1,2-Trimethyl-(1H)-benz[e]indole With 6-amino-1-hexanol, 7-($SO_2NH$—$CH_2$—$CH_2$—$CH_2$—$CH_2$—$CH_2$—$CH_2$—OH)-1,1,2-trimethyl-(1H)-benz[e]indole (VIg)

The sulfonamide was prepared according to the procedure of Example 10 from 1.4 g of 6-amino-1-hexanol (12 mmol), 8 mL of pyridine and 2.5 g of 1,1,2-trimethyl-(1H)-benz[e] indole-4-sulfochloride (7.6 mmol) from Example 9. (Yield: 99%).

EXAMPLE 7a

Preparation of 6-($SO_2NH$—$CH_2$—$CH_2$—$CH_2$—$CH_2$—$NHCOCF_3$)-1,1,2-Trimethyl-(1H)-benz[e] indole (VIIa)

2.6 g of the sulfonamide prepared according to the procedure of Example 6e was treated with trifluoroacetic anhydride at room temperature. (Yield: 83%).

EXAMPLE 7b

Preparation of 7-($SO_2NH$—$CH_2$—$CH_2$—$CH_2$—$CH_2$—$CH_2$—$NHCOCF_3$)-1,1,2-Trimethyl-(1H)-benz[e]indole (VIIb)

3.1 g of the sulfonamide prepared according to the procedure of Example 6f was treated with trifluoroacetic anhydride at room temperature. (Yield: 91%).

EXAMPLE 8

Preparation of 7-($SO_2NH$—$CH_2$—$CH_2$—$CH_2$—$CH_2$—$CH_2$—OTHP)-1,1,2-Trimethyl-(1H)-benz[e]indole (VIII)

2.8 g of the sulfonamide prepared according to the procedure of Example 6g was treated with tetrahydropyrene at room temperature. (Yield: 97%).

EXAMPLE 9a

Preparation of 1-(δ-Sulfonatobutyl)-5-($SO_2NH$—$CH_2$—COOH)-2,3,3-trimethyl-(3H)-indolium (IXa)

In a 100 mL round-bottom flask, 2.5 g (7.1 mmol) of 5-($SO_2NH$—$CH_2$—COO-t-butyl)-2,3,3-trimethyl-(3H)-indole from Example 2a were dissolved in 30 mL of hot sulfolane under argon. To this solution was added 1,4-butanesultone (1 mL, 9.8 mmol). The mixture was then heated at 130° C. for 12 hours. After cooling, the dark solution was mixed with 50 mL of toluene. The brown precipitate was filtered and washed with two 50 mL portions of toluene. The protective group was removed by dissolving the crude product in a few milliliters of methanol/concentrated hydrochloric acid. The resulting solution was stirred for two hours at room temperature and the title product was precipitated by dropwise addition to 500 mL of ether and dried in vacuo. (Yield: 90%).

EXAMPLE 9b

Preparation of 1-(δ-Sulfonatobutyl)-5-($SO_2NH$—$CH_2$—$CH_2$—COOH)-2,3,3-trimethyl-(3H)-indolium (IXb)

The title compound was prepared according to the procedure of Example 9a from 2.2 g (7.1 mmol) of 5-($SO_2NH$—$CH_2$—$CH_2$—COO-t-butyl)-2,3,3-trimethyl-(3H)-indole, Example 2b, and 1.0 mL (9.8 mmol) of 1,4-butanesultone (Yield: 89%).

EXAMPLE 9c

Preparation of 1-(δ-Sulfonatobutyl)-5-($SO_2NH$—$CH_2$—$CH_2$—$CH_2$—$CH_2$—COOH)-2,3,3-trimethyl-(3H)-indolium (IXc)

The title compound was prepared according to the procedure of Example 9a from 2.5 g (7.1 mmol) of 5-($SO_2NH$—$CH_2$—$CH_2$—CH2—CH2—COO-t-butyl)-2,3,3-trimethyl-(3H)-indole, Example 2c, and 1.0 mL (9.8 mmol) of 1,4-butanesultone (Yield: 58%).

EXAMPLE 9d

Preparation of 1-(δ-Sulfonatobutyl)-5-($SO_2NH$—$CH_2$—$CH_2$—$CH_2$—$CH_2$—$CH_2$—$CH_2$—COOH)-2,3,3-trimethyl-(3H)-indolium (IXd)

The title compound was prepared according to the procedure of Example 9a from 2.8 g (7.1 mmol) of 5-($SO_2NH$—$CH_2$—$CH_2$—CH2—CH2—$CH_2$—$CH_2$—COO-t-butyl)-2,3,3-trimethyl-(3H)-indole, Example 2d, and 1.0 mL (9.8 mmol) of 1,4-butanesultone (Yield: 89%).

EXAMPLE 9e

Preparation of 1-(δ-Sulfonatobutyl)-5-($SO_2NH$—$CH_2$—$CH_2$—$CH_2$—$CH_2$—$NH_2$)-2,3,3-trimethyl-(3H)-indolium (IXe)

The title compound was prepared according to the procedure of Example 9a from 2.2 g (7.1 mmol) of 5-($SO_2NH$—$CH_2$—$CH_2$—$CH_2$—$CH_2$—$NHCOCF_3$)-2,3,3-trimethyl-(3H)-indole, Example 3a 1.0 mL (9.8 mmol) of 1,4-butanesultone (Yield: 79%).

EXAMPLE 9f

Preparation of 1-(δ-Sulfonatobutyl)-5-($SO_2NH$—$CH_2$—$CH_2$—$CH_2$—$CH_2$—$CH_2$—$CH_2$—$NH_2$)-2,3,3-trimethyl-(3H)-indolium (IXf)

The title compound was prepared according to the procedure of Example 9a from 2.2 g (7.1 mmol) of 5-($SO_2NH$—$CH_2$—$CH_2$—$CH_2$—$CH_2$—$CH_2$—$CH_2$—$NHCOCF_3$)-2,3,3-trimethyl-benz[e]-(3H)-indole, Example 3b, and 1.0 mL (9.8 mmol) of 1,4-butanesultone. (Yield: 99%).

EXAMPLE 9g

Preparation of 1-(δ-Sulfonatobutyl)-5-($SO_2NH$—$CH_2$—$CH_2$—$CH_2$—$CH_2$—$CH_2$—$CH_2$—OH)-2,3,3-trimethyl-(3H)-indolium (IXg)

The title compound was prepared according to the procedure of Example 9a from 2.2 g (7.1 mmol) of 5-($SO_2$—NH—$CH_2$—$CH_2$—$CH_2$—$CH_2$—$CH_2$—$CH_2$—$CH_2$—$CH_2$—THP)-1,1,2-trimethyl-(1H)-benz[e]indole, Example 4, and 1.0 mL (9.8 mmol) of 1,4-butanesultone (Yield: 89%).

EXAMPLE 10a

Preparation of 1-(δ-Sulfonatobutyl)-6-($SO_2NH$—$CH_2$—COOH)-1,1,2-trimethyl-(1H)-benz[e] indolium (Xa)

The title compound was prepared according to the procedure of Example 9a from 2.2 g (7.1 mmol) of 6-($SO_2NH$—$CH_2$—COOH)-1,1,2-trimethyl-(1H)-benz[e]indole, Example 6a, and 1.0 mL (9.8 mmol) of 1,4-butanesultone (Yield: 95%).

EXAMPLE 10b

Preparation of 1-(δ-Sulfonatobutyl)-6-($SO_2NH$—$CH_2$—$CH_2$—COOH)-1,1,2-trimethyl-(1H)-benz[e]indolium (Xb)

The title compound was prepared according to the procedure of Example 9a from 2.2 g (7.1 mmol) of 6-($SO_2NH$—$CH_2$—$CH_2$—COO-t-butyl)-1,1,2-trimethyl-(1H)-benz[e]indole, Example 6b, and 1.0 mL (9.8 mmol) of 1,4-butanesultone followed by acid hydrolysis (Yield 90%).

EXAMPLE 10c

Preparation of 1-(δ-Sulfonatobutyl)-6-($SO_2NH$—$CH_2$—$CH_2$—$CH_2$—$CH_2$—COOH)-1,1,2-trimethyl-(1H)-benz[e]indolium (Xc)

The title compound was prepared according to the procedure of Example 9a from 2.5 g (7.1 mmol) of 6-($SO_2NH$—$CH_2$—$CH_2$—CH2—CH2—COO-t-butyl)-1,1,2-trimethyl-(1H)-benz[e]indole, Example 6and 1.0 mL (9.8 mmol) of 1,4-butanesultone followed by acid hydrolysis (Yield 85%).

EXAMPLE 10d

Preparation of 1-(δ-Sulfonatobutyl)-6-($SO_2NH$—$CH_2$—$CH_2$—$CH_2$—$CH_2$—$CH_2$—COOH)-1,1,2-trimethyl-(1H)-benz[e]indolium (Xd)

The title compound was prepared according to the procedure of Example 9a from 2.8 g (7.1 mmol) of 6-($SO_2NH$—$CH_2$—$CH_2$—$CH_2$—$CH_2$—$CH_2$—COO-t-butyl)-1,1,2-trimethyl-(1H)-benz[e]indole, Example 6d, and 1.0 mL (9.8 mmol) of 1,4-butanesultone (Yield: 88%).

EXAMPLE 10e

Preparation of 1-(δ-Sulfonatobutyl)-6-($SO_2NH$—$CH_2$—$CH_2$—$CH_2$—$CH_2$—$NH_2$)-1,1,2-trimethyl-(1H)-benz[e]indolium (Xe)

The title compound was prepared according to the procedure of Example 9a from 2.2 g (7.1 mmol) of 6-($SO_2NH$—$CH_2$—$CH_2$—$CH_2$—$CH_2$—$NHCOCF_3$)-1,1,2-trimethyl-(1H)-benz[e]indole, Example 7b, and 1.0 mL (9.8 mmol) of 1,4-butanesultone. (Yield: 80%).

EXAMPLE 10f

Preparation of 1-(δ-Sulfonatobutyl)-6-($SO_2NH$—$CH_2$—$CH_2$—$CH_2$—$CH_2$—$CH_2$—$CH_2$—$NH_2$)-1,1,2-trimethyl-(1H)-benz[e]indolium (Xf)

The title compound was prepared according to the procedure of Example 9a from 2.2 g (7.1 mmol) of 6-($SO_2NH$—$CH_2$—$CH_2$—$CH_2$—$CH_2$—$CH_2$—$CH_2$—$NHCOCF_3$)-1,1,2-trimethyl-(1H)-benz[e]indole, Example 7b, and 1.0 mL (9.8 mmol) of 1,4-butanesultone. (Yield: 67%).

EXAMPLE 10g

Preparation of 1-(δ-Sulfonatobutyl)-6-($SO_2NH$—$CH_2$—$CH_2$—$CH_2$—$CH_2$—$CH_2$—$CH_2$—OH)-1,1,2-trimethyl-(1H)-benz[e]indolium (Xg)

The title compound was prepared according to the procedure of Example 9a from 2.2 g (7.1 mmol) of 6-($SO_2NH$—$CH_2$—$CH_2$—$CH_2$—$CH_2$—$CH_2$—$CH_2$—OTHP)-2,3,3-trimethyl-(3H)-benz[e]-indole, Example 8, and 1.0 mL (9.8 mmol) of 1,4-butanesultone. (Yield: 3.0 g).

EXAMPLE 11a

Preparation of 2-{3'-[1''-(δ-Sulfonatobutyl)-5''-($SO_2NH$—$CH_2$—COOH)-3'',3''-dimethyl-(3''H)-indol-2''-ylidene]-1'-propen-1'-yl}-1-(δ-sulfonatobutyl)-3,3-dimethyl-(3H)-indolium-5-sulfonate (XIa)

In a round-bottom flask equipped with a reflux condenser, a mixture of 300 mg (0.73 mmol) of 1-(δ-sulfonatobutyl)-2,3,3-trimethyl-(3H)-indolium-5-sulfonate (from Mujumdar et al., Bioconjugate Chemistry, 1993, 4, 105–11) and 163 mg (0.83 mmol) of N,N'-diphenyl-formamidine in 2 mL of acetic acid was heated to reflux for 3 h. Acetic acid was evaporated in vacuo and the product triturated with a mixture of ethyl acetate and water. The crude product was redissolved in acetic anhydride (2 mL) and pyridine (2 mL) mixture. 316 mg of 1-(δ-sulfonatobutyl)-5-($SO_2NH$—$CH_2$—COOH)-2,3,3-trimethyl-(3H)-indolium prepared in example 9a was added and mixture was heated at 110° C. for 30 min. After cooling the dye was precipitated by addition of ethyl ether. The crude product was purified by Michel-Miller chromatography on Lichroprep RP18, particle size 25–40 micron, using a mixture of methanol:water as eluent (Yield: 70%).

EXAMPLE 11b

Preparation of 2-{3'-[1''-(δ-Sulfonatobutyl)-5''-($SO_2NH$—$CH_2$—$CH_2$—COOH)-3'',3''-dimethyl-(3''H)-indol-2''-ylidene]-1'-propen-1'-yl}-1-(δ-sulfonatobutyl)-3,3-dimethyl-(3H)-indolium-5-sulfonate (XIb)

The title compound was prepared according to the procedure of Example 1 a from 300 mg (0.73 mmol) of 1-(δ-sulfonatobutyl)-2,3,3-trimethyl-(3H)-indolium-5-sulfonate and 326 mg (0.73 mmol) of 1-(δ-sulfonatobutyl)-5-($SO_2NH$—$CH_2$—$CH_2$—COOH)-2,3,3-trimethyl-(3H)-indolium from example 9b (Yield: 50%).

EXAMPLE 11c

Preparation of 2-{3'-[1''-(δ-Sulfonatobutyl)-5''-($SO_2NH$—$CH_2$—$CH_2$—$CH_2$—COOH)-3'',3''-dimethyl-(3''H)-indol-2''-ylidene]-1'-propen-1'-yl}-1-(δ-sulfonatobutyl)-3,3-dimethyl-(3H)-indolium-5-sulfonate (XIc)

The title compound was prepared according to the procedure of Example 1 1a from 300 mg (0.73 mmol) of 1-(δ-sulfonatobutyl)-2,3,3-trimethyl-(3H)-indolium-5-sulfonate and 336 mg (0.73 mmol) of 1-(δ-sulfonatobutyl)-5-($SO_2NH$—$CH_2$—$CH_2$—$CH_2$—COOH)-2,3,3-trimethyl-(3H)-indolium from example 9c (Yield: 30%).

EXAMPLE 11d

Preparation of 2-{3'-[1''-(δ-Sulfonatobutyl)-5''-($SO_2NH$—$CH_2$—$CH_2$—$CH_2$—$CH_2$—$CH_2$—$CH_2$—COOH)-3'',3''-dimethyl-(3''H)-indol-2''-ylidene]-1'-propen-1'-yl}-1-(δ-sulfonatobutyl)-3,3-dimethyl-(3H)-indolium-5-sulfonate The title compound was prepared according to the procedure of Example 11a from 300 mg (0.73 mmol) of 1-(δ-sulfonatobutyl)-2,3,3-trimethyl-(3H)-indolium-5-sulfonate and 357 mg (0.73 mmol) of 1-(δ-sulfonatobutyl)-5-($SO_2$—NH—$CH_2$—$CH_2$—COOH)-2,3,3-trimethyl-(3H)-indolium from example 9d (Yield: 45%).

EXAMPLE 11e

Preparation of 2-{3'-[1"-(δ-Sulfonatobutyl)-5"-($SO_2$NH—$CH_2$—$CH_2$—$CH_2$—$CH_2$—$NH_2$)-3",3"-dimethyl-(3"H)-indol-2"-ylidene]-1'-propen-1'-yl}-1-(δ-sulfonatobutyl)-3,3-dimethyl-(3H)-indolium-5-sulfonate Trifluoracetate (XIe)

The title compound was prepared according to the procedure of Example 11a from 300 mg (0.73 mmol) of 1-(δ-sulfonatobutyl)-2,3,3-trimethyl-(3H)-indolium-5-sulfonate and 409 mg (0.73 mmol) of 1-(δ-sulfonatobutyl)-5-($SO_2$NH—$CH_2$—$CH_2$—$CH_2$—$CH_2$—$NH_2$)-2,3,3-trimethyl-(3H)-indolium from example 9e (Yield: 30%).

EXAMPLE 11f

Preparation of 2-{3'-[1"-(δ-Sulfonatobutyl)-5"-($SO_2$NH—$CH_2$—$CH_2$—$CH_2$—$CH_2$—$CH_2$—$CH_2$—$NH_2$)-3",3"-dimethyl-(3"H)-indol-2"-ylidene]-1'-propen-1'-yl}-1-(δ-sulfonatobutyl)-3,3-dimethyl-(3H)-indolium-5-sulfonate trifluoroacetate (XIf)

The title compound was prepared according to the procedure of Example 11a from 300 mg (0.73 mmol) of 1-(δ-sulfonatobutyl)-2,3,3-trimethyl-(3H)-indolium-5-sulfonate and 429 mg (0.73 mmol) of 1-(δ-sulfonatobutyl)-5-($SO_2$NH—$CH_2$—$CH_2$—$CH_2$—$CH_2$—$CH_2$—$CH_2$—$NH_3^+$)-2,3,3-trimethyl-(3H)-indolium trifluoroacetate from example 9f (Yield: 35%).

EXAMPLE 11g

Preparation of 2-{3'-[1"-(δ-Sulfonatobutyl)-5"-($SO_2$NH—$CH_2$—$CH_2$—$CH_2$—$CH_2$—$CH_2$—$CH_2$—OH)-3",3"-dimethyl-(3"H)-indol-2"-ylidene]-1'-propen-1'-yl}-1-(δ-sulfonatobutyl)-3,3-dimethyl-(3H)-indolium-5-sulfonate (XIg)

The title compound was prepared according to the procedure of Example 11a from 300 mg (0.73 mmol) of 1-(δ-sulfonatobutyl)-2,3,3-trimethyl-(3H)-indolium-5-sulfonate and 346 mg (0.73 mmol) of 1-(δ-sulfonatobutyl)-5-($SO_2$NH—$CH_2$—$CH_2$—$CH_2$—$CH_2$—$CH_2$—$CH_2$—OH)-2,3,3-trimethyl-(3H)-indolium from example 9g (Yield: 70%).

EXAMPLE 12a

Preparation of 2-{5'-[1"-(δ-Sulfonatobutyl)-5"-($SO_2$NH—$CH_2$—COOH)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate (XIIa)

300 mg (0.73 mmol) of 1-(δ-sulfonatobutyl)-2,3,3-trimethyl-(3H)-indolium-5-sulfonate (from Mujumdar et al., Bioconjugate Chemistry, 1993, 4, 105–11) was dissolved in 1.8 mL of acetic acid in a 25 mL round bottom flask. 845 mg (6.4 mmol) of 1,3,3-trimethoxypropene was added under stirring. The reaction mixture was stirred at room temperature for 30 min. 10 mL of diethyl ether were added and the mixture was stirred for another 15 min and cooled in an ice bath. The supernatant was decanted and the residue was dissolved in a small amount of acetic acid/methanol (50/50) under argon. Cold ether was added and the solution was cooled in an ice bath until a yellow precipitate formed. This precipitate was collected by filtration and washed with a small amount of cold ether.

241 mg (0.50 mmol) of the precipitate was dissolved in 10 mL of methanol, after which 216 mg (0.50 mmol) of 1-(δ-sulfonatobutyl)-5-($SO_2$NH—$CH_2$—COOH)-2,3,3-trimethyl-(3H)-indolium prepared in example 9a (0.50 mmol) and 120 mg (1.22 mmol) of potassium acetate were added. A blue color formed at once. The mixture was stirred at room temperature overnight and diluted with ethyl ether. A dark blue solid separated. The precipitate was collected, dissolved in 1 M hydrochloric acid. The resulting solution was rotoevaporated to dryness. Traces of hydrochloric acid were removed by drying the residue in vacuo in the presence of solid KOH. Purification by Michel-Miller chromatography over Lichroprep RP18 (25–40 micron, Merck, with methanol/water 60:40 as the eluent) afforded 345 mg (77%, calculated for the dipotassium salt) of intermediate dye (XII-a-Cl). The chlorine atom in the cyclohexene ring was removed by overnight stirring of the product in a small volume of a solution of sodium ethanethiolate in N,N-dimethylformamide. The title compound isolated in essentially quantitative yield by ether precipitation.

EXAMPLE 12b

Preparation of 2-{5'-[1"-(δ-Sulfonatobutyl)-5"-($SO_2$NH—$CH_2$—$CH_2$—COOH)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate (XIIb)

The title compound was prepared according to the procedure of Example 12a from 300 mg (0.73 mmol) of 1-(δ-sulfonatobutyl)-2,3,3-trimethyl-(3H)-indolium-5-sulfonate and 223 mg (0.5 mmol) of 1-(δ-sulfonatobutyl)-5-($SO_2$NH—$CH_2$—$CH_2$—COOH)-2,3,3-trimethyl-(3H)-indolium from example 9b (Yield: 55%).

EXAMPLE 12c

Preparation of 2-{5'-[1"-(δ-Sulfonatobutyl)-5"-($SO_2$NH—$CH_2$—$CH_2$—$CH_2$—COOH)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate (XIIc)

The title compound was prepared according to the procedure of Example 12a from 300 mg (0.73 mmol) of 1-(δ-sulfonatobutyl)-2,3,3-trimethyl-(3H)-indolium-5-sulfonate and 230 mg (0.5 mmol) of 1-(δ-sulfonatobutyl)-5-($SO_2$NH—$CH_2$—$CH_2$—$CH_2$—COOH)-2,3,3-trimethyl-(3H)-indolium from example 9c (Yield: 67%).

EXAMPLE 12d

Preparation of 2-{5'-[1"-(δ-Sulfonatobutyl)-5"-($SO_2$NH—$CH_2$—$CH_2$—$CH_2$—$CH_2$—COOH)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate (XIId)

The title compound was prepared according to the procedure of Example 12a from 300 mg (0.73 mmol) of 1-(δ-sulfonatobutyl)-2,3,3-trimethyl-(3H)-indolium-5-sulfonate and 244 mg (0.5 mmol) of 1-(δ-sulfonatobutyl)-5-($SO_2$NH—$CH_2$—$CH_2$—$CH_2$—$CH_2$—COOH)-2,3,3-trimethyl-(3H)-indolium from example 9d (Yield: 80%).

EXAMPLE 12e

Preparation of 2-{5'-[1"-(δ-sulfonatobutyl)-5"-(SO$_2$NH—CH$_2$—CH$_2$—CH$_2$—CH$_2$—NH$_2$)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate Trifluoroacetate (XIIe)

The title compound was prepared according to the procedure of Example 12a from 300 mg (0.73 mmol) of 1-(δ-sulfonatobutyl)-2,3,3-trimethyl-(3H)-indolium-5-sulfonate and 280 mg (0.5 mmol) of 1-(δ-sulfonatobutyl)-5-(SO$_2$NH—CH$_2$—CH$_2$—CH$_2$—CH$_2$—NH$_2$)-2,3,3-trimethyl-(3H)-indolium trifluoroacetate from example 9e (Yield: 30%).

EXAMPLE 12f

Preparation of 2-{5'-[1"-(δ-Sulfonatobutyl)-5"-(SO$_2$NH—CH$_2$—CH$_2$—CH$_2$—CH$_2$—CH$_2$—CH$_2$—CH$_2$—NH$_2$)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate Trifluoroacetate (XIf)

The title compound was prepared according to the procedure of Example 12a from 300 mg (0.73 mmol) of 1-(δ-sulfonatobutyl)-2,3,3-trimethyl-(3H)-indolium-5-sulfonate and 282 mg (0.5 mmol) of 1-(δ-sulfonatobutyl-(SO$_2$NH—CH$_2$—CH$_2$—CH$_2$—CH$_2$—CH$_2$—CH$_2$—CH$_2$—NH$_2$)-2,3,3-trimethyl-(3H)-indolium trifluoroacetate from example 9f (Yield: 48%).

EXAMPLE 12g

Preparation of 2-{5'-[1"-(δ-Sulfonatobutyl)-5" (SO$_2$NH—CH$_2$CH$_2$—CH$_2$—CH$_2$—CH$_2$—CH$_2$—CH$_2$—OH)-3",3"-dimethyl-(3"H)-indol-2"-ylidene]-1',3'-pentadien-1'-yl}-1-(δ-sulfonatobutyl)-3,3-dimethyl-(3H)-indolium-5-sulfonate (IIg)

The title compound was prepared according to the procedure of Example 12a from 300 mg (0.73 mmol) of 1-(δsulfonatobutyl)-2,3,3-trimethyl-(3H)-indolium-5-sulfonate and 237 mg (0.5 mmol) of (δ-sulfonatobutyl-(SO$_2$—NH—CH$_2$—CH$_2$—CH$_2$—CH$_2$—CH$_2$—CH$_2$—CH$_2$—OH)-2,3,3-trimethyl-(3H)-indolium from example 9g (Yield: 80%).

EXAMPLE 13a

Preparation of 2-{7'-[1"-(δ-Sulfonatobutyl)-5"-(SO$_2$NH—CH$_2$—COOH)-3",3"-dimethyl-(3"H)-indol-2"-ylidene]-3',5'-(propane-1"',3"'-diyl)-1',3',5'-haptatrien-1'-yl}-1-(δ-sulfonatobutyl)-3,3-dimethyl-(3H)-indolium-5-sulfonate (XIIIa)

300 mg (0.73 mmol) of 1-(δ-sulfonatobutyl)-2,3,3-trimethyl-(3H)-indolium-5-sulfonate (from Mujumdar et al., Bioconjugate Chemistry, 1993, 4, 105–11) was dissolved in 1.8 mL of acetic acid in a 25 mL round bottom flask. 298 mg (0.83 mmol) of 5-phenylamino-2,4-trimethylene-2,4-pentadienylidene phenylammonium chloride was added under stirring. The reaction mixture was stirred at room temperature for 30 min. 10 mL of diethyl ether were added and the mixture was stirred for another 15 min and cooled in an ice bath. The supernatant was decanted and the residue was dissolved in a small amount of acetic acid/methanol (50/50) under argon. Cold ether was added and the solution was cooled in an ice bath until a brown precipitate formed. This precipitate was collected by filtration and washed with a small amount of cold ether.

322 mg (0.50 mmol) of the precipitate was dissolved in 10 mL of methanol, after which 216 mg (0.50 mmol) of 1-(δ-sulfonatobutyl)-5-(SO$_2$NH—CH$_2$—COOH)-2,3,3-trimethyl-(3H)-indolium prepared in example 9a (0.50 mmol) and 120 mg (1.22 mmol) of potassium acetate were added. A blue color formed at once. The mixture was stirred at room temperature overnight and diluted with ethyl ether. A dark blue solid separated. The precipitate was collected, dissolved in 1 M hydrochloric acid. The resulting solution was rotoevaporated to dryness. Traces of hydrochloric acid were removed by drying the residue in vacuo in the presence of solid KOH. Purification by Michel-Miller chromatography over Lichroprep RP18 (25–40 micron, Merck, with methanol/water 70:30 as the eluent) afforded a 30% yield of intermediate dye (XIII-a-Cl). The chlorine atom in the cyclohexene ring was removed by overnight stirring of the product in a small volume of a solution of sodium ethanethiolate in N,N-dimethylformamide. The title compound isolated in essentially quantitative yield by ether precipitation.

EXAMPLE 13b

Preparation of 2-{7'-[1"-(δ-Sulfonatobutyl)-5"-(SO$_2$NH—CH$_2$—CH$_2$—COOH)-3",3"-dimethyl-(3"H)-indol-2"-ylidene]-3',5'-(propane-1"',3"'-diyl)-1',3',5'-heptatrien-1'-yl}-1-(δ-sulfonatobutyl)-3,3-dimethyl-(3H)-indolium-5-sulfonate (XIIIb)

The title compound was prepared according to the procedure of Example 12a from 300 mg (0.73 mmol) of 1-(δ-sulfonatobutyl)-2,3,3-trimethyl-(3H)-indolium-5-sulfonate and 223 mg (0.5 mmol) of 1-(δ-sulfonatobutyl)-5-(SO$_2$NH—CH$_2$—CH$_2$—COOH)-2,3,3-trimethyl-(3H)-indolium from example 9b (Yield: 25%).

EXAMPLE 13c

Preparation of 2-{7'-[1"-(δ-Sulfonatobutyl)-5"-(SO$_2$NH—CH$_2$—CH$_2$—CH$_2$—COOH)-3",3"-dimethyl-(3"H)-indol-2"-ylidene]-3',5'-(propane-1"',3"'-diyl)-1',3',5'-heptatrien-1'-yl}-1-(δ-sulfonatobutyl)-3,3-dimethyl-(3H)-indolium-5-sulfonate (XIIIc)

The title compound was prepared according to the procedure of Example 12a from 300 mg (0.73 mmol) of 1-(δ-sulfonatobutyl)-2,3,3-trimethyl-(3H)-indolium-5-sulfonate and 230 mg (0.5 mmol) of 1-(δ-sulfonatobutyl)-5-(SO$_2$NH—CH$_2$—CH$_2$—CH$_2$—COOH)-2,3,3-trimethyl-(3H)-indolium from example 9c (Yield: 37%).

EXAMPLE 13d

Preparation of 2-{7'-[1"-(δ-Sulfonatobutyl)-5"-(SO$_2$NH—CH$_2$—CH$_2$—CH$_2$—CH$_2$—CH$_2$—COOH)-3",3"-dimethyl-(3"H)-indol-2"-ylidene]-3',5'-(propane-1"',3"'-diyl)-1',3',5'-heptatrien-1'-yl}-1-(δ-sulfonatobutyl)-3,3-dimethyl-(3H)-indolium-5-sulfonate The title compound was prepared according to the procedure of Example 12a from 300 mg (0.73 mmol) of 1-(δ-sulfonatobutyl)-2,3,3-trimethyl-(3H)-indolium-5-sulfonate and 244 mg (0.5 mmol) of 1-(δ-sulfonatobutyl)-5-(SO$_2$NH—CH$_2$—CH$_2$—CH$_2$—CH$_2$—CH$_2$—COOH)-2,3,3-trimethyl-(3H)-indolium from example 9d (Yield: 50%).

EXAMPLE 13e

Preparation of 2-{7'-[1"-(δ-Sulfonatobutyl)-5"-(SO$_2$NH—CH$_2$—CH$_2$—CH$_2$—CH$_2$—NH$_2$)-3",3"-dimethyl-(3"H)-indol-2"-ylidene]-3',5'-(propane-1"',3"'-diyl)-1',3',5'-heptatrien-1'-yl}-1-(δ-sulfonatobutyl)-3,3-dimethyl-(3H)-indolium-5-sulfonate (XIIIe)

The title compound was prepared according to the procedure of Example 12a from 300 mg (0.73 mmol) of 1-(δ-sulfonatobutyl)-2,3,3-trimethyl-(3H)-indolium-5-sulfonate and 280 mg (0.5 mmol) of 1-(δ-sulfonatobutyl)-5-(SO$_2$NH—CH$_2$—CH$_2$—CH$_2$—CH$_2$—NH$_2$)-2,3,3-trimethyl-(3H)-indolium from example 9e (Yield: 35%).

EXAMPLE 13f

Preparation of 2-{7'-[1"-(δ-Sulfonatobutyl)-5"-(SO$_2$NH—CH$_2$—CH$_2$—CH$_2$—CH$_2$—CH$_2$—CH$_2$—CH$_2$—NH$_2$)-3",3"-dimethyl-(3"H)-indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XIIIf)

The title compound was prepared according to the procedure of Example 12a from 300 mg (0.73 mmol) of 1-(δ-sulfonatobutyl)-2,3,3-trimethyl-(3H)-indolium-5-sulfonate and 282 mg (0.5 mmol) of 1-(δ-sulfonatobutyl-(SO$_2$NH—CH$_2$—CH$_2$—CH$_2$—CH$_2$—CH$_2$—CH$_2$—CH$_2$—NH$_2$)-2,3,3-trimethyl-(3H)-indolium from example 9f (Yield: 40%).

EXAMPLE 13g

Preparation of 2-{7'-[1"-(δ-Sulfonatobutyl)-5"-(SO$_2$NH—CH$_2$—CH$_2$—CH$_2$—CH$_2$CH$_2$—CH$_2$—CH$_2$—OH)-3",3"-dimethyl-(3"H)-indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XIIIg)

The title compound was prepared according to the procedure of Example 12a from 300 mg (0.73 mmol) of 1-(δ-sulfonatobutyl)-2,3,3-trimethyl-(3H)-indolium-5-sulfonate and 237 mg (0.5 mmol) of 1-(δ-sulfonatobutyl-(SO$_2$NH—CH$_2$—CH$_2$—CH$_2$—CH$_2$—CH$_2$—CH$_2$—CH$_2$—OH)-2,3,3-trimethyl-(3H)-indolium from example 9g (Yield: 65%).

EXAMPLE 14a

Preparation of 2-{3'-[3"-(δ-Sulfonatobutyl)-6"-(SO$_2$NH—CH$_2$—COOH)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVa)

In a round-bottom flask equipped with a reflux condenser, a mixture of 338 mg (0.73 mmol) of 3-(δ-sulfonatobutyl)-1,1,2-trimethyl-(1H)-benz[e]indolium-6-sulfonate (from WO 97/13810) and 163 mg (0.83 mmol) of N,N'-diphenylformamidine in 2 mL of acetic acid was heated to reflux for 3 h. Acetic acid was evaporated in vacuo and the product triturated with a mixture of ethyl acetate and water. The crude product was redissolved in acetic anhydride (2 mL) and pyridine (2 mL) mixture. 352 mg (0.73 mmol) of 3-(δ-sulfonatobutyl)-6-(SO$_2$NH—CH$_2$—COOH)-1,1,2-trimethyl-(1H)-benz[e]indolium prepared in example 10a was added and mixture was heated at 110° C. for 30 min. After cooling the dye was precipitated by addition of ethyl ether. The crude product was purified by Michel-Miller chromatography on Lichroprep RP18, particle size 25–40 micron, using a mixture of methanol/water (70/30) as eluent (Yield: 46%).

EXAMPLE 14b

Preparation of 2-{3'-[3"-(δ-sulfonatobutyl)-6"-(SO$_2$NH—CH$_2$—CH$_2$—COOH)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVb)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 362 mg (0.73 mmol) of 3-(δ-sulfonatobutyl)-6-(SO$_2$NH—CH$_2$—CH$_2$—COOH)-1,1,2-trimethyl-(1H)-benz[e]indolium from example 10b (Yield: 40%).

EXAMPLE 14c

Preparation of 2-{3'-[3"-(δ-Sulfonatobutyl)-6"-(SO$_2$NH—CH$_2$—CH$_2$—CH$_2$—COOH)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVc)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 373 mg (0.73 mmol) of 3-(δ-sulfonatobutyl)-6-(SO$_2$NH—CH$_2$—CH$_2$—CH$_2$—COOH)-1,1,2-trimethyl-(1H)-benz[e]indolium from example 10c (Yield: 49%).

EXAMPLE 14d

Preparation of 2-{3'-[3"-(δ-Sulfonatobutyl)-6"-(SO$_2$NH—CH$_2$—CH$_2$—CH$_2$—CH$_2$—CH$_2$—COOH)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVd)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 373 mg (0.73 mmol) of 3-(δ-sulfonatobutyl)-6-(SO$_2$NH—CH$_2$—CH$_2$—CH$_2$—CH$_2$—CH$_2$—COOH)-1,1,2-trimethyl-(1H)-benz[e]indolium from example 10d (Yield: 34%).

EXAMPLE 14e

Preparation of 2-{3'-[3"-(δ-Sulfonatobutyl)-6"-(SO$_2$NH—CH$_2$—CH$_2$—CH$_2$—CH$_2$—NH$_2$)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVe)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 445 mg (0.73 mmol) of 3-(δ-sulfonatobutyl)-6-(SO$_2$NH—CH$_2$—CH$_2$—CH$_2$—CH$_2$—NH$_2$)-1,1,2-trimethyl-(1H)-benz[e]indolium trifluoroacetate from example 10e (Yield: 30%).

EXAMPLE 14f

Preparation of 2-{3'-[3"-(δ-Sulfonatobutyl)-6"-(SO$_2$NH—CH$_2$—CH$_2$—CH$_2$—CH$_2$—CH$_2$—CH$_2$—NH$_2$)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVf)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 465 mg (0.73 mmol) of 3-(δ-sulfonatobutyl)-6-(SO$_2$NH—CH$_2$—CH$_2$—CH$_2$—CH$_2$—CH$_2$—CH$_2$—NH$_2$)-(1H)-benz[e]indolium from example 10f (Yield: 45%).

EXAMPLE 14g

Preparation of 2-{3'-[3"-(δ-Sulfonatobutyl)-6"-(SO$_2$NH—CH$_2$—CH$_2$—CH$_2$—CH$_2$—CH$_2$—CH$_2$—OH)-1",1"-dimethyl-(1"H)-benz[e]indol-2"-ylidene]-1'-propen-1'-yl}-3-(δ-sulfonatobutyl)-1,1-dimethyl-(1H)-benz[e]indolium-6-sulfonate (XIVg)

The title compound was prepared according to the procedure of Example 11a from 300 mg (0.73 mmol) of 1-(δ-sulfonatobutyl)-2,3,3-trimethyl-(3H)-indolium-5-sulfonate and 383 mg (0.73 mmol) of 3-(δ-sulfonatobutyl)-6-($SO_2NH$—$CH_2$—$CH_2$—$CH_2$—$CH_2$—$CH_2$—$CH_2$—OH)-1,1,2-trimethyl-(1H)-benz[e]indolium from example 10g (Yield: 47%).

EXAMPLE 15a

Preparation of 2-{5'-[3"-(δ-Sulfonatobutyl)-6"-($SO_2NH$—$CH_2$—COOH)-1",1"-dimethyl-(1"H)-benz[e]indol-2"-ylidene]-1',3'-pentadien-1'-yl }-3-(δ-sulfonatobutyl)-1,1-dimethyl-(1H)-indolium-5-sulfonate (XVa)

338 mg (0.73 mmol) of 3-(δ-sulfonatobutyl)-1,1,2-trimethyl-(1H)-benz[e]indolium-6-sulfonate (from WO 97/13810) was dissolved in 1.8 mL of acetic acid in a 25 mL round bottom flask. 845 mg (6.4 mmol) of 1,3,3-trimethoxypropene was added under stirring. The reaction mixture was stirred at room temperature for 30 min. 10 mL of diethyl ether were added and the mixture was stirred for another 15 min and cooled in an ice bath. The supernatant was decanted and the residue was dissolved in a small amount of acetic acid/methanol (50/50) under argon. Cold ether was added and the solution was cooled in an ice bath until a yellow precipitate formed. This precipitate was collected by filtration and washed with a small amount of cold ether.

266 mg (0.50 mmol) of the precipitate was dissolved in 10 mL of methanol, after which 241 mg (0.50 mmol) of 3-(δ-sulfonatobutyl)-6-($SO_2NH$—$CH_2$—COOH)-1,1,2-trimethyl-(1H)-benz[e]indolium prepared in example 10a and 120 mg (1.22 mmol) of potassium acetate were added. A blue color formed at once. The mixture was stirred at room temperature overnight and diluted with ethyl ether. A dark blue solid separated. The precipitate was collected, dissolved in 1 M hydrochloric acid. The resulting solution was rotoevaporated to dryness. Traces of hydrochloric acid were removed by drying the residue in vacuo in the presence of solid KOH. Purification by Michel-Miller chromatography over Lichroprep RP18 (25–40 micron, Merck, with methanol/water 60:40 as the eluent) afforded a 73% of the title compound.

EXAMPLE 15b

Preparation of 2-{5'-[3"-(δ-Sulfonatobutyl)-6"-($SO_2NH$—$CH_2$—$CH_2$—COOH)-1",1"-dimethyl-(1"H)-benz[e]indol-2"-ylidene]-1',3'-pentadien-1'-yl}-3-(δ-sulfonatobutyl)-1,1-dimethyl-(1H)-indolium-5-sulfonate (XVb)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 248 mg (0.5 mmol) of 3-(δ-sulfonatobutyl)-6-($SO_2NH$—$CH_2CH_2$—COOH)-1,1,2-trimethyl-(1H)-benz[e]indolium from example 10b (Yield: 67%).

EXAMPLE 15c

Preparation of 2-{5'-[3"-(δ-Sulfonatobutyl)-6"-($SO_2NH$—$CH_2$—$CH_2$—$CH_2$—COOH)-1",1"-dimethyl-(3"H)-benz[e]indol-2"-ylidene]-1',3'-pentadien-1'-yl}-3-(δ-sulfonatobutyl)-1,1-dimethyl-(1H)-indolium-5-sulfonate (XVc)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 255 mg (0.5 mmol) of 3-(δ-sulfonatobutyl)-6-($SO_2NH$—$CH_2$—$CH_2$—$CH_2$—COOH)-1,1,2-trimethyl-(1H)-benz[e]indolium from example 10c (Yield: 55%).

EXAMPLE 15d

Preparation of 2-{5'-[3"-(δ-Sulfonatobutyl)-6"-($SO_2NH$—$CH_2$—$CH_2$—$CH_2$—$CH_2$—$CH_2$—COOH)-1",1"-dimethyl-(1"H)-benz[e]indol-2"-ylidene]-1',3'-pentadien-1'-yl}-3-(δ-sulfonatobutyl)-1,1-dimethyl-(1H)-indolium-5-sulfonate (XVd)

The title compound was prepared according to the procedure of Example 12a from 338 mg (0.73 mmol) 3-(δ-sulfonatobutyl)-1,1,2-trimethyl-(1H)-benz[e]indolium-6-sulfonate and 269 mg (0.5 mmol) of 3-(δ-sulfonatobutyl)-6-($SO_2NH$—$CH_2$—$CH_2$—$CH_2$—$CH_2$—$CH_2$—COOH)-1,1,2-trimethyl-(1H)-benz[e]indolium from example 10d (Yield: 47%).

EXAMPLE 15e

Preparation of 2-{5'-[3"-(δ-Sulfonatobutyl)-6"-($SO_2NH$—$CH_2$—$CH_2$—$CH_2$—$CH_2$—$NH_2$)-1",1"-dimethyl-(1"H)-benz[e]indol-2"-ylidene]-1',3'-pentadien-1'-yl}-3-(δ-sulfonatobutyl)-1,1-dimethyl-(1H)-indolium-5-sulfonate (XVe)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 305 mg (0.5 mmol) of 3-(δ-sulfonatobutyl)-6-($SO_2NH$—$CH_2$—$CH_2$—$CH_2$—$CH_2$—$NH_2$)-1,1,2-trimethyl-(1H)-benz[e]indolium from example 10e (Yield: 60%).

EXAMPLE 15f

Preparation of 2-{5'-[3"-(δ-Sulfonatobutyl)-6"-($SO_2NH$—$CH_2$—$CH_2$—$CH_2$—$CH_2$—$CH_2$—$CH_2$—$NH_2$)-1",1"-dimethyl-(1"H)-benz[e]indol-2"-ylidene]-1',3'-pentadien-1'-yl}-3-(δ-sulfonatobutyl)-1,1-dimethyl-(1H)-indolium-5-sulfonate (XVf)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 319 mg (0.5 mmol) of 3-(5-sulfonatobutyl)-6-($SO_2NH$—$CH_2$—$CH_2$—$CH_2$—$CH_2$—$CH_2$—$CH_2$—$NH_2$)-1,1,2-trimethyl-(1H)-benz[e]indolium trifluoroacetate from example 10f (Yield: 79%).

EXAMPLE 15g

Preparation of 2-{5'-[3"-(δ-Sulfonatobutyl)-6"-($SO_2NH$—$CH_2$—$CH_2$—$CH_2$—$CH_2$—$CH_2$—$CH_2$—OH)-1",1"-dimethyl-( 1"H)-benz[e]indol-2"-ylidene]-1',3'-pentadien-1'-yl}-3-(δ-sulfonatobutyl)-1,1-dimethyl-(1H)-benz[e]indolium-6-sulfonate (XVg)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 262 mg (0.5 mmol) of 3-(δ-sulfonatobutyl)-6-($SO_2NH$—$CH_2$—$CH_2$—$CH_2$—$CH_2$—$CH_2$—$CH_2$—OH)-1,1,2-trimethyl-(1H)-benz[e]indolium trifluoroacetate from example 10g (Yield: 59%).

EXAMPLE 16a

Preparation of 2-{7'-[3"-(δ-Sulfonatobutyl)-5"-($SO_2NH$—$CH_2$—COOH)-1",1"-dimethyl-(1"H)-benz[e]indol-2"-ylidene]-3',5'-(propane-1'",3'"-diyl)-1',3',5'-heptatrien-1'-yl}-3-(δ-sulfonatobutyl)-1,1-dimethyl-(1H)-benz[e]indolium-6-sulfonate (XVIa)

338 mg (0.73 mmol) of 3-(δ-sulfonatobutyl)-1,1,2-trimethyl-(1H)-benz[e]indolium-6-sulfonate (from WO 97/13810) was dissolved in 1.8 mL of acetic acid in a 25 mL round bottom flask. 298 mg (0.83 mmol) of 5-phenylamino-2,4-trimethylene-2,4-pentadienylidene phenylammonium chloride was added under stirring. The reaction mixture was stirred at room temperature for 30 min. 10 mL of diethyl ether were added and the mixture was stirred for another 15 min and cooled in an ice bath. The supernatant was decanted and the residue was dissolved in a small amount of acetic acid/methanol (50/50) under argon. Cold ether was added and the solution was cooled in an ice bath until a brown precipitate formed. This precipitate was collected by filtration and washed with a small amount of cold ether.

322 mg (0.50 mmol) of the precipitate was dissolved in 10 mL of methanol, after which 241 mg (0.50 mmol) of 3-(δ-sulfonatobutyl)-6-($SO_2NH$—$CH_2$—COOH)-1,1,2-trimethyl-(1H)-benz[e]indolium prepared in example 10a and 120 mg (1.22 mmol) of potassium acetate were added. A blue color formed at once. The mixture was stirred at room temperature overnight and diluted with ethyl ether. A dark blue solid separated. The precipitate was collected, dissolved in 1 M hydrochloric acid. The resulting solution was rotoevaporated to dryness. Traces of hydrochloric acid were removed by drying the residue in vacuo in the presence of solid KOH. Purification by Michel-Miller chromatography over Lichroprep RP18 (25–40 micron, Merck, with methanol/water 70:30 as the eluent) afforded a 30% yield of of the title compound.

EXAMPLE 16b

Preparation of 2-{7'-[3"-(δ-Sulfonatobutyl)-6"-($SO_2NH$—$CH_2$—$CH_2$—COOH)-1",1"-dimethyl-(1'H)-benz[e]indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XVIb)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 248 mg (0.5 mmol) of 3-(δ-sulfonatobutyl)-6-($SO_2NH$—$CH_2$—$CH_2$—COOH)-1,1,2-trimethyl-(1H)-benz[e]indolium from example 10b (Yield: 36%).

EXAMPLE 16c

Preparation of 2-{7'-[3"-(δ-Sulfonatobutyl)-6"-($SO_2NH$—$CH_2$—$CH_2$—$CH_2$—COOH)-1",1"-dimethyl-(1"H)-benz[e]indol-2"-ylidene]-3',5'-(propane-1''',3'''-diyl)-1',3',5'-heptatrien-1'-yl}3-(δ-sulfonatobutyl)-1,1-dimethyl-(1H)-benz[e]indolium-6-sulfonate (XVIc)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 255 mg (0.5 mmol) of 3-(δ-sulfonatobutyl)-6-($SO_2NH$—$CH_2$—$CH_2$—$CH_2$—COOH)-1,1,2-trimethyl-(1H)-benz[e]indolium from example 10c (Yield: 89%).

EXAMPLE 16d

Preparation of 2-{7'-[3"-(δ-Sulfonatobutyl)-6"-($SO_2NH$—$CH_2$—$CH_2$—$CH_2$—$CH_2$—COOH)-1",1"-dimethyl-(1"H)-benz[e]indol-2"-ylidene]-3',5'-(propane-1''',3'''-diyl)-1',3',5'-heptatrien-1'-yl}3-(δ-sulfonatobutyl)-1,1-dimethyl-(1H)-benz[e]indolium-6-sulfonate (XVId)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 269 mg (0.5 mmol) of 3-(δ-sulfonatobutyl)-6-($SO_2NH$—$CH_2$—$CH_2$—$CH_2$—$CH_2$—$CH_2$—COOH)-1,1,2-trimethyl-(1H)-benz[e]indolium from example 10d (Yield: 41%).

EXAMPLE 16e

Preparation of 2-{7'-[3"-(δ-Sulfonatobutyl)-6"-($SO_2NH$—$CH_2$—$CH_2$—$CH_2$—$CH_2$—$NH_2$)-1",1"-dimethyl-(1"H)-benz[e]indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XVIe)

The title compound was prepared according to the procedure of Example 12a from 338 mg (0.73 mmol) of 3-(5-sulfonatobutyl)-1,1,2-trimethyl-(1H)-benz[e]indolium-6-sulfonate and 305 mg (0.5 mmol) of 3-(δ-sulfonatobutyl)-6-($SO_2NH$—$CH_2$—$CH_2$—$CH_2$—$CH_2$—$NH_2$)-1,1,2-trimethyl-(1H)-benz[e]indolium trifluoroacetate from example 10e (Yield: 30%).

EXAMPLE 16f

Preparation of 2-{7'-[3"-(δ-Sulfonatobutyl)-6"-($SO_2NH$—$CH_2$—$CH_2$—$CH_2$—$CH_2$—$CH_2$—$CH_2$—$NH_2$)-1",1"-dimethyl-(1"H)-benz[e]indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XVIf)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 319 mg (0.5 mmol) of 3-(δ-sulfonatobutyl)-6-($SO_2NH$—$CH_2$—$CH_2$—$CH_2$—$CH_2$—$CH_2$—$CH_2$—$NH_3^+$)-1,2,2-trimethyl-(1H)-benz[e]indolium trifluoroacetate from example 10f (Yield: 45%).

EXAMPLE 16g

Preparation of 2-{7'-[3"-(δ-Sulfonatobutyl)-6"-($SO_2NH$—$CH_2$—$CH_2$—$CH_2$—$CH_2$—$CH_2$—$CH_2$—OH)-1",1"-dimethyl-(1"H)-benz[e]indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XVIg)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 262 mg (0.5 mmol) of 3-(δ-sulfonatobutyl)-6-($SO_2NH$—$CH_2$—$CH_2$—$CH_2$—$CH_2$—$CH_2$—$CH_2$—OH)-1,1,2-trimethyl-(1H)-benz[e]indolium from example 10g (Yield: 70%).

EXAMPLE 17a

Preparation of 2-{3'-[3"-(δ-Sulfonatobutyl)-5"-($SO_2NH$—$CH_2$—COOH)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIa)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 316 mg (0.73 mmol) of 1-(δ-sulfonatobutyl)-5-($SO_2NH$—$CH_2$—COOH)-2,3,3-trimethyl-(3H)-indolium from example 9a (Yield: 40%).

EXAMPLE 17b

Preparation of 2-{3'-[1"-(δ-Sulfonatobutyl)-5"-(SO$_2$NH—CH$_2$—CH$_2$—COOH)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIb)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 326 mg (0.73 mmol) of 1-(δ-sulfonatobutyl)-5-(SO$_2$NH—CH$_2$—CH$_2$—COOH)-2,3,3-trimethyl-(3H)-indolium from example 9b (Yield: 55%).

EXAMPLE 17c

Preparation of 2-{3'-[1"-(δ-Sulfonatobutyl)-5"-(SO$_2$NH—CH$_2$—CH$_2$—CH$_2$—COOH)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIc)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 336 mg (0.73 mmol) of 1-(δ-sulfonatobutyl)-5-(SO$_2$NH—CH$_2$—CH$_2$—CH$_2$—COOH)-2,3,3-trimethyl-(3H)-indolium from example 9c (Yield: 37%).

EXAMPLE 17d

Preparation of 2-{3'-[1"-(δ-Sulfonatobutyl)-5"-(SO$_2$NH—CH$_2$—CH$_2$—CH$_2$—CH$_2$—CH$_2$—CH$_2$—COOH)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIId)

The title compound was prepared according to the procedure of Example 11a from 338 mg (0.73 mmol) of 3-(5-sulfonatobutyl)-1,1,2-trimethyl-(1H)-benz[e]indolium-6-sulfonate and 357 mg (0.73 mmol) of 1-(δ-sulfonatobutyl)-5-(SO$_2$—NH—CH$_2$—CH$_2$—CH$_2$—CH$_2$—CH$_2$—COOH)-2,3,3-trimethyl-(3H)-indolium from example 9d (Yield: 35%).

EXAMPLE 17e

Preparation of 2-{3'-[1"-(δ-Sulfonatobutyl)-5"-(SO$_2$NH—CH$_2$—CH$_2$—CH$_2$—CH$_2$—NH$_2$)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIe)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 409 mg (0.73 mmol) of 1-(δ-sulfonatobutyl)-5-(SO$_2$NH—CH$_2$—CH$_2$—CH$_2$—CH$_2$—NH$_2$)-2,3,3-trimethyl-(3H)-indolium from example 9e (Yield: 38%).

EXAMPLE 17f

Preparation of 2-{3'-[1"-(δ-Sulfonatobutyl)-5"-(SO$_2$NH—CH$_2$—CH$_2$—CH$_2$—CH$_2$—CH$_2$—CH$_2$—NH$_2$)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIf)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 429 mg (0.73 mmol) of 1-(δ-sulfonatobutyl)-5-(SO$_2$NH—CH$_2$—CH$_2$—CH$_2$—CH$_2$—CH$_2$—CH$_2$—NH$_2$)-2,3,3-trimethyl-(3H)-indolium trifluoroacetate from example 9f (Yield: 45%).

EXAMPLE 17g

Preparation of 2-{3'-[1"-(δ-Sulfonatobutyl)-5"-(SO$_2$NH—CH$_2$—CH$_2$—CH$_2$—CH$_2$—CH$_2$—OH)-3",3"-dimethyl-(3"H)-indol-2"-ylidene]-1'-propen-1'-yl}-3-(δ-sulfonatobutyl)-1,1-dimethyl-(1H)-benz[e]indolium-6-sulfonate (XVIIg)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 346 mg (0.73 mmol) of 1-(δ-sulfonatobutyl)-5-(SO$_2$NH—CH$_2$—CH$_2$—CH$_2$—CH$_2$—CH$_2$—CH$_2$—OH)-2,3,3-trimethyl-(3H)-indolium from example 9g (Yield: 78%).

EXAMPLE 18a

Preparation of 2-{5'-[1"-(δ-Sulfonatobutyl)-5"-(SO$_2$NH—CH$_2$—COOH)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIa)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 316 mg (0.73 mmol) of 1-(δ-sulfonatobutyl)-5-(SO$_2$NH—CH$_2$—COOH)-2,3,3-trimethyl-(3H)-indolium from example 9a (Yield: 45%).

EXAMPLE 18b

Preparation of 2-{5'-[1"-(δ-Sulfonatobutyl)-5"-(SO$_2$NH—CH$_2$—CH$_2$—COOH)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIb)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 326 mg (0.73 mmol) of 1-(δ-sulfonatobutyl)-5-(SO$_2$NH—CH$_2$—CH$_2$—COOH)-2,3,3-trimethyl-(3H)-indolium from example 9b (Yield: 53%).

EXAMPLE 18c

Preparation of 2-{5'-[1"-(δ-Sulfonatobutyl)-5"-(SO$_2$NH—CH$_2$—CH$_2$—CH$_2$—COOH)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIc)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 336 mg (0.73 mmol) of 1-(δ-sulfonatobutyl)-5-(SO$_2$NH—CH$_2$—CH$_2$—CH$_2$—COOH)-2,3,3-trimethyl-(3H)-indolium from example 9c (Yield: 47%).

EXAMPLE 18d

Preparation of 2-{5'-[1"-(δ-Sulfonatobutyl)-5"-(SO$_2$NH—CH$_2$—CH$_2$—CH$_2$—CH$_2$—CH$_2$—CH$_2$—COOH)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIId)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 357 mg (0.73 mmol) of 1-(δ-sulfonatobutyl)-5-(SO$_2$—NH—CH$_2$—CH$_2$—CH$_2$—CH$_2$—CH$_2$—COOH)-2,3,3-trimethyl-(3H)-indolium from example 9d (Yield: 44%).

EXAMPLE 18e

Preparation of 2-{5'-[1"-(δ-Sulfonatobutyl)-5"-(SO$_2$NH—CH$_2$—CH$_2$—CH$_2$—CH$_2$—NH$_2$)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIe)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 409 mg (0.73 mmol) of 1-(δ-sulfonatobutyl)-5-(SO$_2$NH—CH$_2$—CH$_2$—CH$_2$—CH$_2$—NH$_2$)-2,3,3-trimethyl-(3H)-indolium from example 9e (Yield: 42%).

EXAMPLE 18f

Preparation of 2-{5'-[1"-(δ-Sulfonatobutyl)-5"-(SO$_2$NH—CH$_2$—CH$_2$—CH$_2$—CH$_2$—CH$_2$—CH$_2$—NH$_2$)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIf)

The title compound was prepared according to the procedure of Example 11a from 338 mg (0.73 mmol) of 3-(δ-sulfonatobutyl)-1,1,2-trimethyl-(1H)-benz[e]indolium-6-sulfonate and 429 mg (0.73 mmol) of 1-(δ-sulfonatobutyl)-5-(SO$_2$NH—CH$_2$—CH$_2$—CH$_2$—CH$_2$—CH$_2$—CH$_2$—NH$_2$)-2,3,3-trimethyl-(3H)-indolium trifluoroacetate from example 9f (Yield: 34%).

EXAMPLE 18g

Preparation of 2-{5'-[1"-(δ-Sulfonatobutyl)-5"-(SO$_2$NH—CH$_2$—CH$_2$—CH$_2$—CH$_2$—CH$_2$—CH$_2$—OH)-3",3"-dimethyl-(3"H)-indol-2"-ylidene]-1',3'-pentadien-1'-yl}-3-(δ-sulfonatobutyl)-1,1-dimethyl-(1H)-benz[e]indolium-6-sulfonate (XVIIIg)

The title compound was prepared according to the procedure of Example 12a from 338 mg (0.73 mmol) of 3-(δ-sulfonatobutyl)-1,1,2-trimethyl-(1H)-benz[e]indolium-6-sulfonate and 346 mg (0.73 mmol) of 1-(δ-sulfonatobutyl)-5-(SO$_2$NH—CH$_2$—CH$_2$—CH$_2$—CH$_2$—CH$_2$—CH$_2$—OH)-2,3,3-trimethyl-indolium from example 9g (Yield: 67%).

EXAMPLE 19a

Preparation of 2-{7'-[1"-(δ-Sulfonatobutyl)-5"-(SO$_2$NH—CH$_2$—COOH)-3",3"-dimethyl-(3"H)-indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XIXa)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 316 mg (0.73 mmol) of 1-(δ-sulfonatobutyl)-5-(SO$_2$NH—CH$_2$—COOH)-2,3,3-trimethyl-(3H)-indolium from example 9a (Yield: 36%).

EXAMPLE 19b

Preparation of 2-{7'-[1"-(δ-Sulfonatobutyl)-5"-(SO$_2$NH—CH$_2$—CH$_2$—COOH)-3",3"-dimethyl-(3"H)-indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XIXb)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 326 mg (0.73 mmol) of 1-(δ-sulfonatobutyl)-5-(SO$_2$NH—CH$_2$—CH$_2$—COOH)-2,3,3-trimethyl-(3H)-indolium from example 9b (Yield: 33%).

EXAMPLE 19c

Preparation of 2-{7'-[1"-(δ-Sulfonatobutyl)-5"-(SO$_2$NH—CH$_2$—CH$_2$—CH$_2$—COOH)-3",3"-dimethyl-(3"H)-indol-2"-ylidene]-3',5'-(propane-1''', 3'''-diyl)-1',3',5'-heptatrien-1'-yl}-3-(δ-sulfonatobutyl)-1,1-dimethyl-(1H)-benz[e]indolium-6-sulfonate (XIXc)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 336 mg (0.73 mmol) of 1-(δ-sulfonatobutyl)-5-(SO$_2$NH—CH$_2$—CH$_2$—CH$_2$—COOH)-2,3,3-trimethyl-(3H)-indolium from example 9c (Yield: 41%).

EXAMPLE 19d

Preparation of 2-{7'-[1"-(δ-Sulfonatobutyl)-5"-(SO$_2$NH—CH$_2$—CH$_2$—CH$_2$—CH$_2$—CH$_2$—CH$_2$—COOH)-3",3"-dimethyl-(3"H)-indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XIXd)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 357 mg (0.73 mmol) of 1-(δ-sulfonatobutyl)-5-(SO$_2$—NH—CH$_2$—CH$_2$—CH$_2$—CH$_2$—CH$_2$—COOH)-2,3,3-trimethyl-indolium from example 9d (Yield: 22%).

EXAMPLE 19e

Preparation of 2-{7'-[1"-(δ-Sulfonatobutyl)-5"-(SO$_2$NH—CH$_2$—CH$_2$—CH$_2$—CH$_2$—NH$_2$)-3",3"-dimethyl-(3"H)-indol-2"-ylidene]-3',5'-(propane-1''', 3'''-diyl)-1',3',5'-heptatrien-1'-yl}-3-(δ-sulfonatobutyl)-1,1-dimethyl-(1H)-benz[e]indolium-6-sulfonate (XIXe)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 409 mg (0.73 mmol) of 1-(5-sulfonatobutyl)-5-(SO$_2$NH—CH$_2$—CH$_2$—CH$_2$—CH$_2$—NH$_2$)-2,3,3-trimethyl-(3H)-indolium from example 9e (Yield: 35%).

EXAMPLE 19f

Preparation of 2-{7'-[1"-(δ-Sulfonatobutyl)-5"-(SO$_2$NH—CH$_2$—CH$_2$—CH$_2$—CH$_2$—CH$_2$—CH$_2$—NH$_2$)-3",3"-dimethyl-(3"H)-indol-2"-ylidene]-3',5'-(propane-1''',3'''-diyl)-1',3',5'-heptatrien-1'-yl}-3-(δ-sulfonatobutyl)-1,1-dimethyl-(1H)-benz[e]indolium-6-sulfonate (XIXf)

The title compound was prepared according to the procedure of Example 13a from 338 mg (0.73 mmol) of 3-(5-sulfonatobutyl)-1,1,2-trimethyl-(1H)-benz[e]indolium-6-sulfonate and 429 mg (0.73 mmol) of 1-(δ-sulfonatobutyl)-5-(SO$_2$NH—CH$_2$—CH$_2$—CH$_2$—CH$_2$—

$CH_2$—$CH_2$—$NH_2$)-2,3,3-trimethyl-(3H)-indolium trifluoroacetate from example 9f (Yield: 32%).

EXAMPLE 19g

Preparation of 2-{7'-[1"-(δ-Sulfonatobutyl)-5"-($SO_2NH$—$CH_2$—$CH_2$—$CH_2$—$CH_2$—$CH_2$—$CH_2$—OH)-3",3"-dimethyl-(3"H)-indol-2"-ylidene]-3',5'-(propane-1"',3"'-diyl)-1',3',5'-heptatrien-1'-yl}-3-(δ-sulfonatobutyl)-1,1-dimethyl-(1H)-benz[e]indolium-6-sulfonate (XIXg)

The title compound was prepared according to the procedure of Example 13a from 338 mg (0.73 mmol) of 3-(δ-sulfonatobutyl)-1,1,2-trimethyl-(1H)-benz[e]indolium-6-sulfonate and 346 mg (0.73 mmol) of 1-(5-sulfonatobutyl)-5-($SO_2NH$—$CH_2$—$CH_2$—$CH_2$—$CH_2$—$CH_2$—$CH_2$—OH)-2,3,3-trimethyl-indolium from example 9g (Yield: 33%).

EXAMPLE 20a

Preparation of 2-{3'-[1"-(δ-Sulfonatobutyl)-6"-($SO_2NH$—$CH_2$—COOH)-1",1"-dimethyl-(1"H)-benz[e]indol-2"-ylidene]-1'-propen-1'-yl}-1-(δ-sulfonatobutyl)-3,3-dimethyl-(3H)-indolium-5-sulfonate (XXa)

The title compound was prepared according to the procedure of Example 11a from 300 mg (0.73 mmol) of 1-(5-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—COOH)-1,1,2-trimethyl-(1H)-benz[e]indolium prepared in example 10a (Yield: 30%).

EXAMPLE 20b

Preparation of 2-{3'-[1"-(δ-Sulfonatobutyl)-6"-($SO_2NH$—$CH_2$—$CH_2$—COOH)-1",1"-dimethyl-(1"H)-benz[e]indol-2"-ylidene]-1'-propen-1'-yl}-1-(δ-sulfonatobutyl)-3,3-dimethyl-(3H)-indolium-5-sulfonate (XXb)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—COOH)-1,1,2-trimethyl-(1H)-benz[e]indolium prepared in example 10b (Yield: 33%).

EXAMPLE 20c

Preparation of 2-{3'-[1"-(δ-Sulfonatobutyl)-6"-($SO_2NH$—$CH_2$—$CH_2$—$CH_2$—COOH)-1",1"-dimethyl-(1"H)-benz[e]indol-2"-ylidene]-1'-propen-1'-yl }-1-(δ-sulfonatobutyl)-3,3-dimethyl-(3H)-indolium-5-sulfonate (XXc)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—$CH_2$—COOH)-1,1,2-trimethyl-(1H)-benz[e]prepared in example 10c (Yield: 39%).

EXAMPLE 20d

Preparation of 2-{3'-[1"-(δ-Sulfonatobutyl)-6"-($SO_2$—NH—$CH_2$—$CH_2$—$CH_2$—$CH_2$—$CH_2$—COOH)-1",1"-dimethyl-(1"H)-benz[e]indol-2"-ylidene]-1'-propen-1'-yl}-1-(δ-sulfonatobutyl)-3,3-dimethyl-(3H)-indolium-5-sulfonate (XXd)

The title compound was prepared according to the procedure of Example 11a from 300 mg (0.73 mmol) of 1-(5-sulfonatobutyl)-2,3,3-trimethyl-(3H)-indolium-5-sulfonate and 352 mg (0.73 mmol) and 357 mg (0.73 mmol) of 3-(δ-sulfonatobutyl)-6-($SO_2$—NH—$CH_2$—$CH_2$—$CH_2$—$CH_2$—$CH_2$—COOH)-1,1,2-trimethyl-(1H)-benz[e]indolium from example 10d (Yield: 43%).

EXAMPLE 20e

Preparation of 2-{3'-[1"-(δ-Sulfonatobutyl)-6"-($SO_2NH$—$CH_2$—$CH_2$—$CH_2$—$CH_2$—$NH_2$)-1",1"-dimethyl-(1"H)-benz[e]indol-2"-ylidene]-1'-propen-1'-yl}-1-(δ-sulfonatobutyl)-3,3-dimethyl-(3H)-indolium-5-sulfonate (XXe)

The title compound was prepared according to the procedure of Example 11a from 300 mg (0.73 mmol) of 1-(δ-sulfonatobutyl)-2,3,3-trimethyl-(3H)-indolium-5-sulfonate and 409 mg (0.73 mmol) of 3-(δ-sulfonatobutyl)-6-($SO_2$—NH—$CH_2$—$CH_2$—$CH_2$—$CH_2$—$NH_2$)-1,1,2-trimethyl-(1H)-benz[e]indolium from example 10e (Yield: 33%).

EXAMPLE 20f

Preparation of 2-{3'-[1"-(δ-Sulfonatobutyl)-6"-($SO_2NH$—$CH_2$—$CH_2$—$CH_2$—$CH_2$—$CH_2$—$CH_2$—$NH_3^+$)-1",1"-dimethyl-(1"H)-benz[e]indol-2"-ylidene]-1'-propen-1'-yl}-3-(δ-sulfonatobutyl)-1,1-dimethyl-(1H)-indolium-6-sulfonate (XXf)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 429 mg (0.73 mmol) of 1-(δ-sulfonatobutyl)—-5-($SO_2NH$—$CH_2$—$CH_2$—$CH_2$—$CH_2$—$CH_2$—$CH_2$—$NH_3^+$)-2,3,3-trimethyl-(3H)-indolium trifluoroacetate from example 10f (Yield: 45%).

EXAMPLE 20g

Preparation of 2-{3'-[1"-(δ-Sulfonatobutyl)-6"-($SO_2NH$—$CH_2$—$CH_2$—$CH_2$—$CH_2$—$CH_2$—$CH_2$—OH)-1",1"-dimethyl-(1"H)-benz[e]indol-2"-ylidene]-1'-propen-1'-yl}-3-(δ-sulfonatobutyl)-1,1-dimethyl-(1H)-indolium-6-sulfonate (XXg)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 346 mg (0.73 mmol) of 1-(δ-sulfonatobutyl)-5-($SO_2NH$—$CH_2$—$CH_2$—$CH_2$—$CH_2$—$CH_2$—$CH_2$—OH)-2,3,3-trimethyl-(3H)-indolium from example 10g (Yield: 78%).

EXAMPLE 21a

Preparation of 2-{5'-[3"-(δ-Sulfonatobutyl)-6"-($SO_2NH$—$CH_2$—$CH_2$—COOH)-1",1"-dimethyl-(1"H)-benz[e]indol-2"-ylidene]-1',3'-pentadien-1'-yl}-1-(δ-sulfonatobutyl)-3,3-dimethyl-(3H)-indolium-5-sulfonate (XXIa)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—COOH)-1,1,2-trimethyl-(1H)-benz[e]indolium prepared in example 10a (Yield: 27%).

EXAMPLE 21b

Preparation of 2-{5'-[3"-(δ-Sulfonatobutyl)-6"-($SO_2NH$—$CH_2$—$CH_2$—COOH)-1",1"-dimethyl-(1"H)-benz[e]indol-2"-ylidene]-1',3'-pentadien-1'-yl}-1-(δ-sulfonatobutyl)-3,3-dimethyl-(3H)-indolium-5-sulfonate (XXIb)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—COOH)1,1,2-trimethyl-(1H)-benz[e]indolium prepared in example 10b (Yield: 36%).

EXAMPLE 21c

Preparation of 2-{5'-[3"-(δ-Sulfonatobutyl)-(6"-($SO_2NH$—$CH_2$—$CH_2$—$C_2$—COOH)-1",1"-dimethyl-(1'H)-benz[e]indol-2"-ylidene]-1,3'-pentadien-1'-yl}-1-(δ-sulfonatobutyl)-3,3-dimethyl-(3H)-indolium-5-sulfonate (XXIc)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—$CH_2$—COOH)-1,1,2-trimethyl-(1H)-benz[e]indolium prepared in example 10c (Yield: 39%).

EXAMPLE 21d

Preparation of 2-{5'-[3"-(δ-Sulfonatobutyl)-(6"-($SO_2$—NH—$CH_2$—$CH_2$—$CH_2$—$CH_2$—$CH_2$—COOH)-1",1"-dimethyl-(1"H)-benz[e]indol-2"-ylidene]-1',3'-pentadien-1'-yl}-1-(δ-sulfonatobutyl)-3,3-dimethyl-(3H)-indolium-5-sulfonate (XXId)

The title compound was prepared according to the procedure of Example 11a from 300 mg (0.73 mmol) of 1-(δ-sulfonatobutyl)-2,3,3-trimethyl-(3H)-indolium-5-sulfonate and 352 mg (0.73 mmol) and 357 mg (0.73 mmol) of 3-(δ-sulfonatobutyl)-6-($SO_2$—NH—$CH_2$—$CH_2$—$CH_2$—$CH_2$—$CH_2$—COOH)-1,1,2-trimethyl-(1H)-benz[e]indolium from example 10d (Yield: 48%).

EXAMPLE 21e

Preparation of 2-{5'-[1"-(δ-Sulfonatobutyl)-6"-($SO_2NH$—$CH_2$—$CH_2$—$CH_2$—$CH_2$—$NH_2$)-1",1"-dimethyl-(1"H)-benz[e]indol-2"-ylidene]-1',3'-pentadien-1'-yl}-1-(δ-sulfonatobutyl)-3,3-dimethyl-(3H)-indolium-5-sulfonate (XXIe)

The title compound was prepared according to the procedure of Example 11a from 300 mg (0.73 mmol) of 1-(δ-sulfonatobutyl)-2,3,3-trimethyl-(3H)-indolium-5-sulfonate and 409 mg (0.73 mmol) of 3-(δ-sulfonatobutyl)-6-($SO_2$—NH—$CH_2$—$CH_2$—$CH_2$—$CH_2$—$NH_2$)-1,1,2-trimethyl-(1H)-benz[e]indolium from example 10e (Yield: 30%).

EXAMPLE 21f

Preparation of 2-{5'-[1"-(δ-Sulfonatobutyl)-6"-($SO_2NH$—$CH_2$—$CH_2$—$CH_2$—$CH_2$—$CH_2$—$CH_2$—$NH_2$)-1",1"-dimethyl-(1"H)-benz[e]indol-2"-ylidene]-1',3'-pentadien-1'-yl}-3-(δ-sulfonatobutyl)-1,1-dimethyl-(1H)-indolium-6-sulfonate (XXIf)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 429 mg (0.73 mmol) of 1-(δ-sulfonatobutyl)-5-($SO_2NH$—$CH_2$—$CH_2$—$CH_2$—$CH_2$—$CH_2$—$CH_2$—$NH_2$)-2,3,3-trimethyl-(3H)-indolium trifluoroacetate from example 10f (Yield: 45%).

EXAMPLE 21g

Preparation of 2-{5'-[1"-(δ-Sulfonatobutyl)-6"-($SO_2NH$—$CH_2$—$CH_2$—$CH_2$—$CH_2$—$CH_2$—$CH_2$—OH)-1",1"-dimethyl-(1"H)-benz[e]indol-2"-ylidene]-1',3'-pentadien-1'-yl}-3-(δ-sulfonatobutyl)-1,1-dimethyl-(1H)-indolium-6-sulfonate (XXIg)

The title compound was prepared according to the procedure of Example 11a from 300 mg (0.73 mmol) of 3-(δ-sulfonatobutyl)-1,1,2-trimethyl-(1H)-benz[e]indolium-6-sulfonate and 346 mg (0.73 mmol) of 1-(δ-sulfonatobutyl)-5-($SO_2NH$—$CH_2$—$CH_2$—$CH_2$—$CH_2$—$CH_2$—$CH_2$—OH)-2,3,3-trimethyl-(3H)-indolium from example 10g (Yield: 56%).

EXAMPLE 22a

Preparation of 2-{7'-[3"-(δ-Sulfonatobutyl)-6"-($SO_2NH$—$CH_2$—COOH)-1",1"-dimethyl-(1"H)-benz[e]indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XXIIa)

The title compound was prepared according to the procedure of Example 13a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—COOH)-1,1,2-trimethyl-(1H)-benz[e]indolium prepared in example 10a (Yield: 14%).

EXAMPLE 22b

Preparation of 2-{7'-[3"-(δ-Sulfonatobutyl)-6"-($SO_2NH$—$CH_2$—$CH_2$—COOH)-1",1"-dimethyl-(1"H)-benz[e]indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XXIIb)

The title compound was prepared according to the procedure of Example 13a from 300 mg (0.73 mmol) of 1-(δsulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—COOH)-1,1,2-trimethyl-(1H)-benz[e]indolium prepared in example 10b (Yield: 25%).

EXAMPLE 22c

Preparation of 2-{7'-[3"-(δ-Sulfonatobutyl)-6"-($SO_2NH$—$CH_2$—$CH_2$—$CH_2$—COOH)-1",1"-dimethyl-(1"H)-benz[e]indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XXIIc)

The title compound was prepared according to the procedure of Example 13a from 300 mg (0.73 mmol) of 1-(δ-sulfonatobutyl)-2,3,3-trimethyl-(3H)-indolium-5-sulfonate and 352 mg (0.73 mmol) of 3-(δ-sulfonatobutyl)-6-($SO_2NH$—$CH_2$—$CH_2$—$CH_2$—COOH)-1,1,2-trimethyl-(1H)-benz[e]indolium prepared in example 10c (Yield: 23%).

EXAMPLE 22d

Preparation of 2-{7'-[3"-(δ-Sulfonatobutyl)-6"-($SO_2$—NH—$CH_2$—$CH_2$—$CH_2$—$CH_2$—$CH_2$—COOH)-1",1"-dimethyl-(1"H)-benz[e]indol-2"-ylidene]-3',5'-(propane-1''',3'''-diyl)-1',3',5'-heptatrien-1'-yl}-1-(δ-sulfonatobutyl)-3,3-dimethyl-(3H)-indolium-5-sulfonate (XXIId)

The title compound was prepared according to the procedure of Example 13a from 300 mg (0.73 mmol) of 1-(δ-sulfonatobutyl)-2,3,3-trimethyl-(3H)-indolium-5-sulfonate and 352 mg (0.73 mmol) and 357 mg (0.73 mmol) of 3-(δ-sulfonatobutyl)-6-($SO_2$—NH—$CH_2$—$CH_2$—$CH_2$—$CH_2$—$CH_2$—COOH)-1,1,2-trimethyl-(1H)-benz[e]indolium from example 10d (Yield: 28%).

EXAMPLE 22e

Preparation of 2-{7'-[1"-(δ-Sulfonatobutyl)-6"-(SO$_2$NH—CH$_2$—CH$_2$—CH$_2$—CH$_2$—NH$_2$)-1",1"-dimethyl-(1"H)-benz[e]indol-2"-ylidene]-3',5'-(propane-1'",3'"-diyl)-1',3',5'-heptatrien-1'-yl}-1-(δ-sulfonatobutyl)-3,3-dimethyl-(3H)-indolium-5-sulfonate (XXIIe)

The title compound was prepared according to the procedure of Example 13a from 300 mg (0.73 mmol) of 1-(δ-sulfonatobutyl)-2,3,3-trimethyl-(3H)-indolium-5-sulfonate and 409 mg (0.73 mmol) of 3-(5-sulfonatobutyl)-6-(SO$_2$—NH—CH$_2$—CH$_2$—CH$_2$—CH$_2$—NH$_2$)-1,1,2-trimethyl-(1,1,2-trimethyl-(1H)-benz[e]indolium from example 10e (Yield: 20%).

EXAMPLE 22f

Preparation of 2-{7'-[1"-(δ-Sulfonatobutyl)-6"-(SO$_2$NH—CH$_2$—CH$_2$—CH$_2$—CH$_2$—CH$_2$—NH$_2$)-1",1"-dimethyl-(1"H)-benz[e]indol-2"-ylidene]-3',5'-(propane-1'",3'"-diyl)-1',3',5'-heptatrien-1'-yl}-3-(δ-sulfonatobutyl)-1,1-dimethyl-(1H)-indolium-6-sulfonate (XXIIf)

The title compound was prepared according to the procedure of Example 13a from 300 mg (0.73 mmol) of 3-(δ-sulfonatobutyl)-1,1,2-trimethyl-(1H)-benz[e]indolium-6-sulfonate and 429 mg (0.73 mmol) of 1-(δ-sulfonatobutyl)-5-(SO$_2$NH—CH$_2$—CH$_2$—CH$_2$—CH$_2$—CH$_2$—CH$_2$—NH$_2$)-2,3,3-trimethyl-(3H)-indolium trifluoroacetate from example 10f (Yield: 65%).

EXAMPLE 22g

Preparation of 2-{7'-[1"-(δ-Sulfonatobutyl)-6"-(SO$_2$NH—CH$_2$—CH$_2$—CH$_2$—CH$_2$—CH$_2$—CH$_2$—OH)-1",1"-dimethyl-(1"H)-benz[e]indol-2"-ylidene]-3',5'-(propane-1'",3'"-diyl)-1',3',5'-heptatrien-1'-yl}-3-(δ-sulfonatobutyl)-1,1-dimethyl-(1H)-indolium-6-sulfonate (XXIIg)

The title compound was prepared according to the procedure of Example 13a from 300 mg (0.73 mmol) of 3-(δ-sulfonatobutyl)-1,1,2-trimethyl-(1H)-benz[e]indolium-6-sulfonate and 346 mg (0.73 mmol) of 1-(δ-sulfonatobutyl)-5-(SO$_2$NH—CH$_2$—CH$_2$—CH$_2$—CH$_2$—CH$_2$—CH$_2$—OH)-2,3,3-trimethyl-(3H)-indolium from example 10g (Yield: 53%).

EXAMPLE 23

General Procedure for the Preparation of Succinimidyl Esters of the Dyes with a —SO$_2$NH(CH)$_n$COOH Linker Arm The following procedure describes the preparation of succinimidyl esters of the dyes with a (N-carboxyalkyl) sulfamoyl linker arm —SO$_2$NH(CH)$_n$COOH.

0.5 mol of a cyanine dye bearing an —SO$_2$NH(CH)$_n$COOH linker arm, prepared as shown in Examples 11a–d–22a–d, 83.9 mg (1.5 mmol) of N-hydroxysuccinimide, and 100 mg (1.5 mmol) of dicyclohexylcarbodiimide (DCC) were dissolved in 10 mL of dry acetonitrile. After being stirred overnight, the reaction mixture was filtered to remove dicyclohexylurea. Acetonitrile was evaporated at room temperature. After trituration with 50 mL of ethyl acetate, the residue was dissolved in a minimal amount of dry acetonitrile and reprecipitated by the addition of diethyl ether.

EXAMPLE 24

General Procedure for the Preparation of Phosphoramidites of the Dyes with a —SO$_2$NH(CH$_2$)$_6$OH Linker Arm The following procedure describes the preparation of phosphoramidites of the dyes with a (N-hydroxyalkyl) sulfamoyl linker arm —SO$_2$NH(CH$_2$)$_6$OH.

A cyanine dye bearing an —SO$_2$NH(CH$_2$)$_6$OH linker arm (0.5 mmol, prepared as shown in Examples 11g–22g was dried by coevaporation with dry acetonitrile, followed by dissolution in 30 mL of dry acetonitrile. A few grains of tetrazole were added to the solution, followed by the phosphitylating agent, bis-(N,N-diisopropyl)-β-cyanoethyl phosphoramidite (232 mg, 0.77 mmol). The reaction was monitored by TLC. The solvent was evaporated and the flask was evacuated under high vacuum overnight. The resulting solid was triturated several times with dry diethyl ether and dried under high vacuum overnight and stored under argon at −20° C.

EXAMPLE 25

Labelling of anti-HCG Antibody with the Succinimidylesters Dyes of Example 23

The coupling of the succinimidyl esters dyes of Example 23 was carried out as follows.

Stock solutions were prepared for the coupling reactions:
(1) 5 mg/mL of succinimidyl ester dye of Example 23 in dry DMF.
(2) 1.0 mg/mL of anti-HGH from rabbit (DAKO) in 0.1 M, carbonate/bicarbonate buffer, pH 9.3.

50 μL of dye was added to 1 mL of anti-HCG stock solution. The mixture was thoroughly mixed on a vortex mixer and incubated overnight in the dark at room temperature in a shaker incubator. The reaction mixture was then chromatographed over Sephadex G-25 using a 150 mM NaCl, 10 mM phosphate buffer pH 7.0. Depending on the dye employed, a dye-to-antibody ratio of 5–7 was estimated, using the following formula: Dye/IgG=A$_{dye}$ε$_{IgG}$/(A$_{278}$—c%A$_{dye}$)ε$_{dye}$, where A$_{dye}$ is the conjugate absorbance at the maximum absorption of the dye, ε$_{IgG}$ is the extinction coefficient of the IgG antibody at 278 nm, ε$_{dye}$ is the extinction coefficient of dye at its maximum absorption, A$_{280}$ is the conjugate absorbance at 280 nm, and c% is the percentage of dye absorption at 278 nm with respect to its maximum absorption.

EXAMPLE 26

Performance of a Fluorescence Immunoassay with β-HCG Standards

For the quantitative determination of β-HCG standards, a sandwich test was carried out. To a set of siliconized test tubes, there was added 50 μL of β-HCG standard solution (0 mIU/mL; 10 mIU/mL; 25 mIU/mL; 50 mIU/ML; 100 mIU/mL; 200 mIU/mL). Then 50 μL of a solution containing 3.9×10$^{-8}$ M of anti-HCG labeled as described in Example 25 in dilution buffer pH 7.0 (0.1 M Tris Buffer, 20% foetal calf serum 0.05 Thimerosal and 0.02% Tween 20). An additional 150 μL of buffer solution (150 mM Na phosphate with 20g/L bovine serum albumine) is added to each test tube and finally a 6.5 mm polystyrene bead coated with capture anti-β-HCG IgG via a streptavidine-biotin layer is added to each test tube. The mixture is incubated overnight at 37° C. on a shaker incubator. The capture beads are then washed three times with distilled water and then transferred into test tubes containing 2 mL of 0.1 M sulfuric acid. After 30 min the sulfuric acid solution is pipetted into fluorescence cuvettes and the dye content is measured by fluorescence spectroscopy. A typical calibration curve is as follows: 0 mIU/mL—0.050 FI; 10 mIU/mL—1.56 FI; 25 mIU/mL 3.54 FI; 50 mIU/mL—5.01 FI; 100 mIU/mL 8.93 FI; 200 mIU/ML 15.99 FI, where FI is the relative fluorescence intensity in arbitrary units.

EXAMPLE 27

Labelling of anti-α-Fetoprotein Antibody With the Succinimidylesters Dyes of Example 23

The coupling of anti-α-fetoprotein with the succinimidyl esters dyes of Example 23 was carried out in the same way as that of the anti-β-HCG reported in Example 25.

Stock solutions were prepared for the coupling reactions:
(3) 4.0 mg/mL of succinimidyl ester dye of Example 23 in dry DMF.
(4) 2.0 mg/mL of anti-α-fetoprotein from rabbit (DAKO) in 0.1 M, carbonate/bicarbonate buffer, pH 9.3.

50 μL of dye was added to 1 mL of anti-α-fetoprotein stock solution. The mixture was thoroughly mixed on a vortex mixer and incubated overnight in the dark at room temperature in a shaker incubator. The reaction mixture was then chromatographed over Sephadex G-25 using a 150 mM NaCl, 10 mM phosphate buffer pH 7.0. Depending on the dye employed, a dye-to-antibody ratio of 3.5–4.5 was estimated, using the following formula: Dye/IgG=$A_{dye}\epsilon_{IgG}$/($A_{278}$—c%$A_{dye}$)$\epsilon_{dye}$, where $A_{dye}$ is the conjugate absorbance at the maximum absorption of the dye, $\epsilon_{IgG}$ is the extinction coefficient of the IgG antibody at 278 nm, $\epsilon_{dye}$ is the extinction coefficient of dye at its maximum absorption, $A_{280}$ is the conjugate absorbance at 280 nm, and c% is the percentage of dye absorption at 278 nm with respect to its maximum absorption.

EXAMPLE 28

Performance of a Fluorescence Immunoassay With α-Fetoprotein Standards

For the quantitative determination of α-fetoprotein standards, a sandwich test was carried out. To a set of siliconized test tubes, there was added 50 μL of α-fetoprotein standard solution (0 ng/mL; 5 ng/mL; 15 ng/mL; 50 mIU/ML; 100 mIU/mL; 250 ng/mL). Then 50 μL of a solution containing 5.8×10$^{-8}$ M of anti-α-fetoprotein labeled as described in Example 27 in dilution buffer pH 7.0 (0.1 M Tris Buffer, 20% foetal calf serum 0.05 Thimerosal and 0.02% Tween 20). An additional 150 μL of buffer solution (150 mM Na phosphate with 20 g/L bovine serum albumine) is added to each test tube and finally a 6.5 mm polystyrene bead coated with capture anti-α-fetoprotein IgG via a streptavidine-biotin layer is added to each test tube. The mixture is incubated overnight at 37° C. on a shaker incubator. The capture beads are then washed three times with distilled water and then transferred into test tubes containing 2 mL of 0.1 M sulfuric acid. After 30 min the sulfuric acid solution is pipetted into fluorescence cuvettes and the dye content is measured by fluorescence spectroscopy. A typical calibration curve is as follows: 0 ng/mL—0.71 FI; 5 ng/mL—0.92 FI; 15 ng/mL 1.25 FI; 50 ng/mL—1.97 FI; 100 mIU/mL 4.01 FI; 250 mIU/ML 7.56 FI, where FI is the relative fluorescence intensity in arbitrary units.

EXAMPLE 29

Method for Labelling Ribonucleotides, Deoxyribonucleotides and Dideoxyribonucleotides With the Succinimidylesters Dyes of Example 23

3-amino-1-propynyl ribonucleotides, deoxyribonucleotides and dideoxyribonucleotides (AP-3 nucleotides) were prepared as described in U.S. Pat. No. 5,151,507. In such compounds the 3-amino-1-propynyl linker is attached to the 5 position of pyrimidines or the 7 position of 7-deazapurines. The AP-3 nucleotides were dissolved to a final concentration of 10 mM.

Stock solutions containing 2 mg/100 μL of succinimidyl ester dyes of Example 23 in anhydrous dimethylsulfoxided ester dyes of Example 23 in anhydrous dimethylsulfoxided were prepared. To 0.1 μmol of AP-3 ribonucleotides, deoxyribonucleotides or dideoxyribonucleotides was added 30 μL of 0.25 M carbonate pH 9.0 buffer followed by the addition of 5 μL of succinimidyl ester dyes in dimethylsulfoxide. The mixture was rapidly mixed on a vortex mixer and then incubated overnight in the dark at room temperature in shaker incubator. Dye-labeled nucleotides were purified by gradient RP-HPLC (Buffer A: 100 mM triethylammonium acetate pH 7.0 in water; Buffer B: 100 mM triethylammonium acetate in 70% (v/V) acetonitrile; flow rate: 1.0 mL /min) evaporated to near dryness and diluted in 1 mM EDTA, 10 mM Tris-HCl pH 8.0 buffer.

EXAMPLE 30

Preparation of a Theophylline-cyanine Conjugate 515 mg (0.56 mmol) of 2-{5'-[1"-(δ-sulfonatobutyl)-5"-(SO$_2$NH—CH$_2$—CH$_2$—CH$_2$—CH$_2$—NH$_2$)-3",4"-dimethyl-(3"H)-indol-2"-ylidene]-1',3'-pentadien-1'-yl}-1-(5-sulfonatobutyl)-3,3-dimethyl-(3H)-indolium-5-sulfonate from Example 12e and 165 mg (0.56 mmol) of theophylline-8-(3',3'-dimethyl)butyric acid (8-(2',6'-dihydroxy-1',3'-dimethylpurin-8'-yl)-3,3-butyric acid; prepared by condensing 5,5-diamino-1,3-dimethyluracil hydrate with 3,3-dimethylglutaric anhydride in pyridine according to the Traube method) were dissolved at room temperature in 1 mL of dry pyridine. To the solution was added 116 mg (0.56 mmol) of dicyclohexylcarbodiimide and 64 mg (0.56 mmol) of N-hydroxysuccinimide. Stirring at room temperature was continued overnight. Precipitated dicyclourea was removed by filtration and the pyridine was evaporated in vacuo. The residue was dissolved in the minimum amount of a 50:50 water/methanol mixture and purified by RP-HPLC chromatography (eluent: water/methanol 50:50).

What is claimed is:
1. A fluorescent compound of the formula:

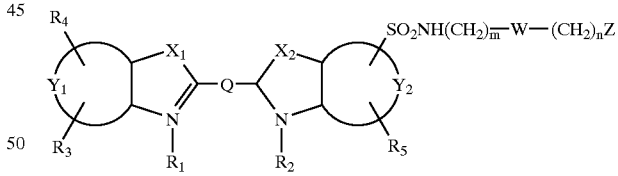

wherein:
X$_1$, X$_2$ are independently selected from the group consisting of —O—, —S—, —C(CH$_3$)$_2$ and —C═CH$_2$;
Y$_1$, Y$_2$ are nonmetal atoms required to form a benzo-condensed or naphtha-condensed ring;
Q is a conjugated moiety that increases the fluorescent quantum yield and the stability of the compound;
R$_1$ and R$_2$ are independently selected from the group consisting of H, C$_1$–C$_4$, alkyl, alkylensulfonic group and alkylensulfonate group wherein the alkylene group has from 1 to 4 carbon atoms;
R$_3$, R$_4$ and R$_5$ are independently selected from the group consisting of H, a sulfonic group, a sulfonate group, alkylensulfonic, alkylensulfonate and —SO$_2$NH(CH$_2$)

$_m$—W—$(CH_2)_n$Z, wherein alkylene has 1 to 4 carbon atoms, with the proviso that at least one of $R_1$ to $R_5$ contains a sulfonic or sulfonate group;

W is absent or is a group selected from the group consisting of —$SO_2NH$—, —O—, —COO—, and —CONH—; n=0–12 and m=0–12 with he provisos that m+n≦12 and at least one of m and n≠0 ;

and Z is, or contains a N, O or S nucleophile functionality or is, or contains a functionality capable of reacting with N, O or S nucleophiles.

2. A fluorescent compound according to claim 1 wherein Z is a nucleophile functionality selected from the group consisting of —$NH_2$, —OH, and —SH.

3. A fluorescent compound according to claim 1 wherein Z is a functionality capable of reacting with N, O, S nucleophiles selected from the group consisting of —COCl, —COOCOR, —$CONHNH_2$, N-hydroxysuccinimido esters, —NCS, —CHO, —$CHOCH_2I$, phosphoramidite and maleimido.

4. A fluorescent compound according to claim 1, wherein at least two of the groups $R_1$ to $R_5$ contain a sulfonic acid or a sulfonate group.

5. A fluorescent compound according to claim 1, wherein R3, R4, R5 are all a group of the formula —$SO_2NH(CH_2)$ $_m$—W—$(CH_2)_n$Z.

6. A fluorescent compound according to claim 1, wherein $X_1$ and $X_2$ are both —$C(CH_3)_2$.

7. A fluorescent compound according to claim 1, wherein Q is a polymethine chain having from 3 to 7 carbon atoms selected from the group consisting of:

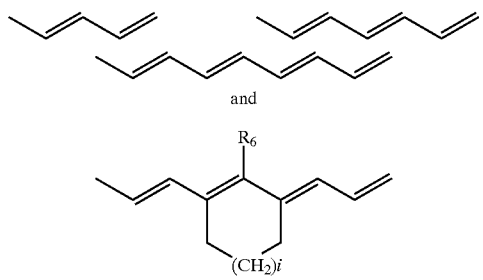

wherein $R_6$ is selected from the group consisting of H, a halogen atom and the group $SO_2NH(CH_2)_n$ and i is 0 or 1.

8. A fluorescent compound according to claim 1 having the formula 2a to 2n:

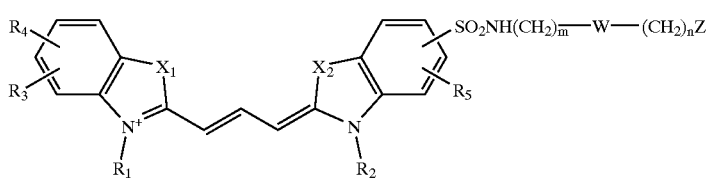

2a

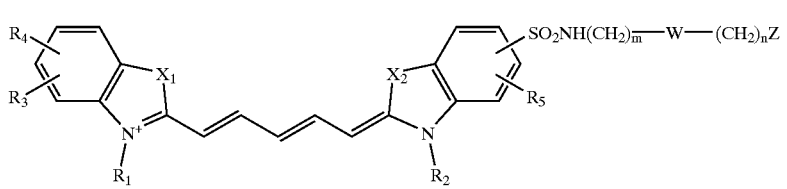

2b

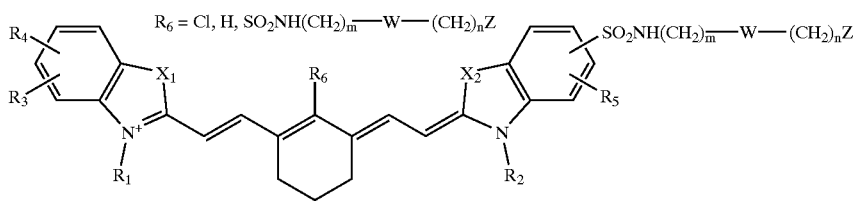

2c

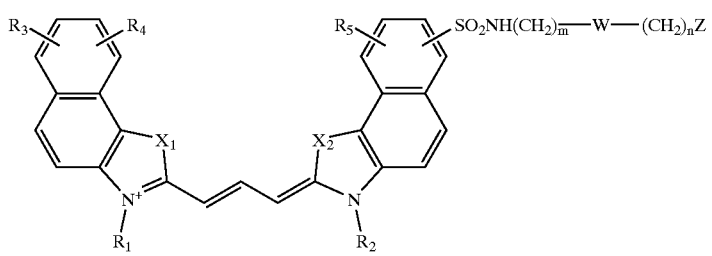

2d

-continued
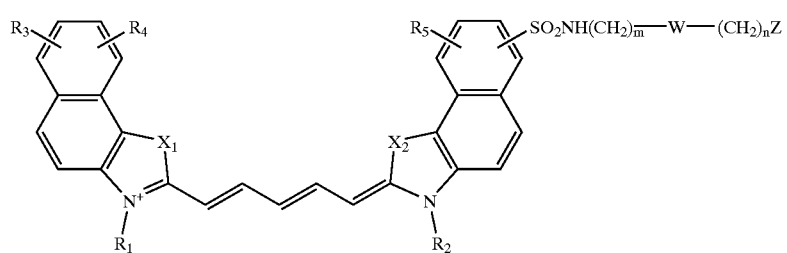
2e
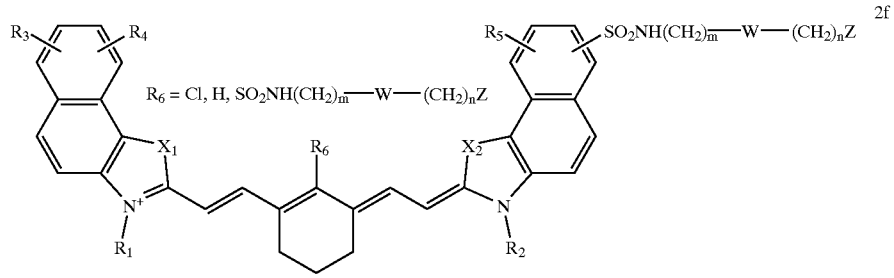
2f
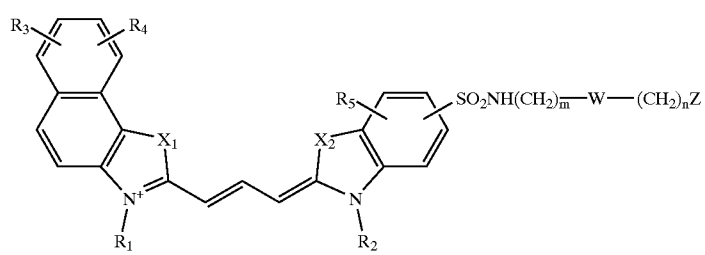
2g
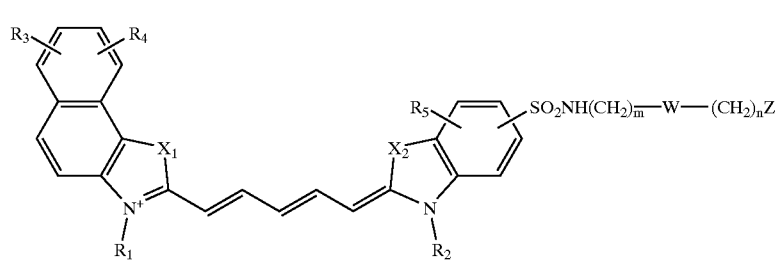
2h
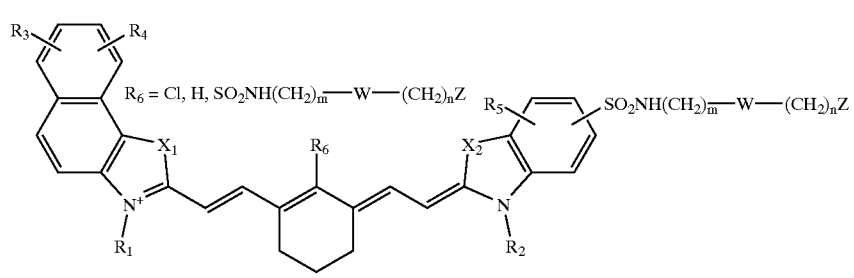
2i
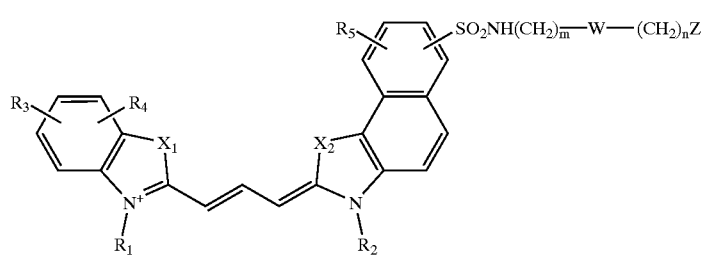
2l -continued

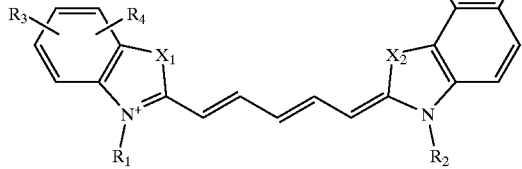

2m

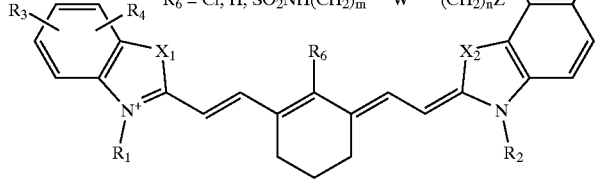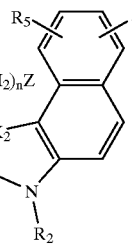

2n

9. A nucleic acid probe labelled with a fluorescent compound of claim 1.

10. An immunological binding reagent labelled with a fluorescent compound according to claim 1.

11. A nucleotide labelled with a fluorescent compound according to claim 1.

12. A nucleoside labelled with a fluorescent compound according to claim 1.

13. A method of assaying an analyte in a sample comprising contacting a nucleic acid probe or an immunologically binding reagent labelled with a fluorescent compound according to claim 1 under suitable conditions for binding with an analyte wherein the binding is representative of the presence or amount of the analyte in the sample and determining the extent of said binding by measuring the fluorescence of the bound nucleic acid probe or immunologically binding reagent labelled with said fluorescent compound.

14. A kit for an assay comprising a compound according to claim 1 and a nucleic acid probe or an immunological binding reagent.

* * * * *

UNITED STATES PATENT AND TRADEMARK OFFICE
CERTIFICATE OF CORRECTION

PATENT NO. : 6,448,008 B1
DATED : September 10, 2002
INVENTOR(S) : Giuseppe Caputo and Leopoldo Della Ciana It is certified that error appears in the above-identified patent and that said Letters Patent is hereby corrected as shown below:

<u>Column 38,</u>
Line 22, after "halogen atom and the group" delete "$SO_2NH(CH_2)_n$" and insert
-- $SO_2NH(CH_2)_m—W—(CH_2)_nZ$ --

Signed and Sealed this

Sixteenth Day of November, 2004

JON W. DUDAS
*Director of the United States Patent and Trademark Office*